(12) United States Patent
Rickard et al.

(10) Patent No.: US 10,933,068 B2
(45) Date of Patent: Mar. 2, 2021

(54) MODULATORS OF DUX4 FOR REGULATION OF MUSCLE FUNCTION

(71) Applicant: GENEA BIOCELLS USA (HOLDINGS), INC., San Diego, CA (US)

(72) Inventors: Amanda Rickard, San Diego, CA (US); Anabel De La Garza, San Diego, CA (US); Uli Schmidt, San Diego, CA (US); Alexander Kiselyov, San Diego, CA (US)

(73) Assignee: Sonic Master Limited, Tortola (VG)

( * ) Notice: Subject to any disclaimer, the term of this patent is extended or adjusted under 35 U.S.C. 154(b) by 108 days.

(21) Appl. No.: 16/302,805

(22) PCT Filed: May 26, 2017

(86) PCT No.: PCT/AU2017/050498
§ 371 (c)(1),
(2) Date: Nov. 19, 2018

(87) PCT Pub. No.: WO2017/201585
PCT Pub. Date: Nov. 30, 2017

(65) Prior Publication Data
US 2019/0298727 A1  Oct. 3, 2019

Related U.S. Application Data

(60) Provisional application No. 62/342,143, filed on May 26, 2016, provisional application No. 62/460,186, filed on Feb. 17, 2017.

(51) Int. Cl.
| | |
|---|---|
| *A61K 31/5377* | (2006.01) |
| *A61P 21/00* | (2006.01) |
| *A61K 31/4439* | (2006.01) |
| *A61K 31/4545* | (2006.01) |
| *A61K 31/496* | (2006.01) |
| *A61K 31/52* | (2006.01) |
| *A61K 31/551* | (2006.01) |
| *G01N 33/50* | (2006.01) |
| *A61K 31/5513* | (2006.01) |
| *A61K 45/06* | (2006.01) |
| *A61K 31/706* | (2006.01) |
| *A61K 31/4412* | (2006.01) |

(52) U.S. Cl.
CPC ...... *A61K 31/5377* (2013.01); *A61K 31/4412* (2013.01); *A61K 31/4439* (2013.01); *A61K 31/4545* (2013.01); *A61K 31/496* (2013.01); *A61K 31/52* (2013.01); *A61K 31/551* (2013.01); *A61K 31/5513* (2013.01); *A61K 31/706* (2013.01); *A61K 45/06* (2013.01); *A61P 21/00* (2018.01); *G01N 33/5023* (2013.01); *G01N 33/5061* (2013.01)

(58) Field of Classification Search
None
See application file for complete search history.

(56) References Cited

U.S. PATENT DOCUMENTS

| | | | | |
|---|---|---|---|---|
| 2005/0009840 A1* | 1/2005 | Cui | ............ | A61P 9/08 |
| | | | | 514/255.05 |
| 2007/0032529 A1* | 2/2007 | Takagi | ............ | A61K 31/415 |
| | | | | 514/341 |
| 2010/0056506 A1* | 3/2010 | Huang | ............ | A61P 1/04 |
| | | | | 514/228.2 |
| 2011/0183974 A1* | 7/2011 | Dessole | ............ | C07D 417/14 |
| | | | | 514/234.5 |
| 2013/0317026 A1* | 11/2013 | Kuntz | ............ | C07D 471/04 |
| | | | | 514/234.5 |
| 2015/0301067 A1* | 10/2015 | Miller | ............ | G01N 33/5061 |
| | | | | 514/21.92 |

OTHER PUBLICATIONS

Balog et al. "Increased DUX4 expression during muscle differentiation correlates with decreased SMCHD1 protein levels at D4Z4," Epigenetics 10:12, 1133-1142; Dec. 2015 (Year: 2015).*

* cited by examiner

*Primary Examiner* — Jeffrey S Lundgren
*Assistant Examiner* — Michael J Schmitt

(57) ABSTRACT

Disclosed herein are methods and compositions for the treatment of facioscapulohumeral muscular dystrophy and other muscle diseases or disorders. In some cases, the methods and compositions involve the use of methyltransferase inhibitors to inhibit or repress DUX4 expression in muscle cells. Further disclosed herein are methods and cell based assays for screening compounds for the treatment of facioscapulohumeral muscular dystrophy and other muscle diseases.

15 Claims, 23 Drawing Sheets

Dux4 transfection
(GEN49-Dux4/GFP)

Dux4 transfection
(GEN50-Dux4/GFP)

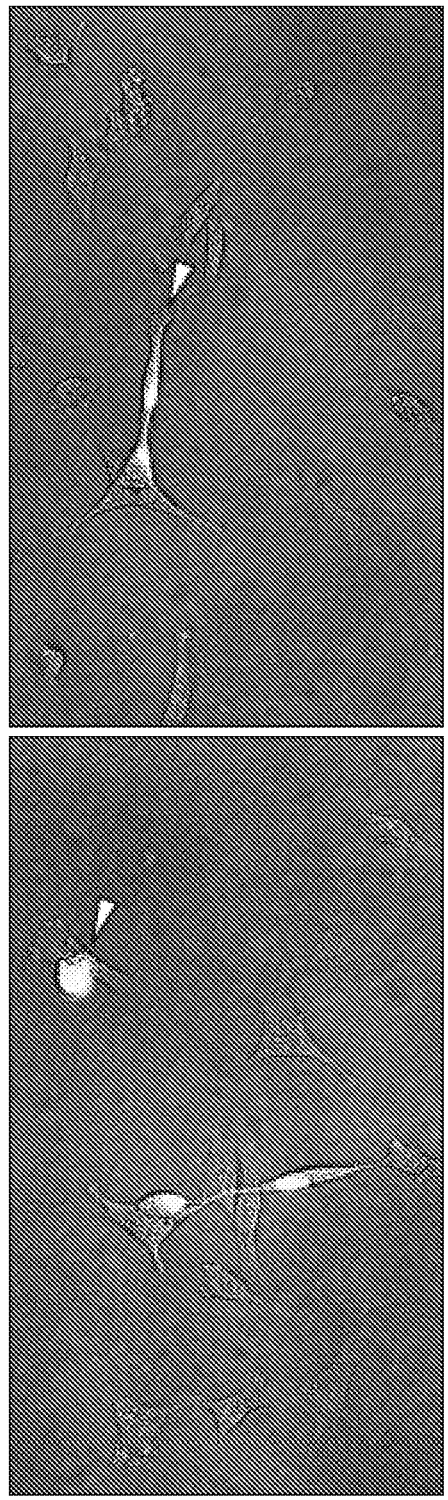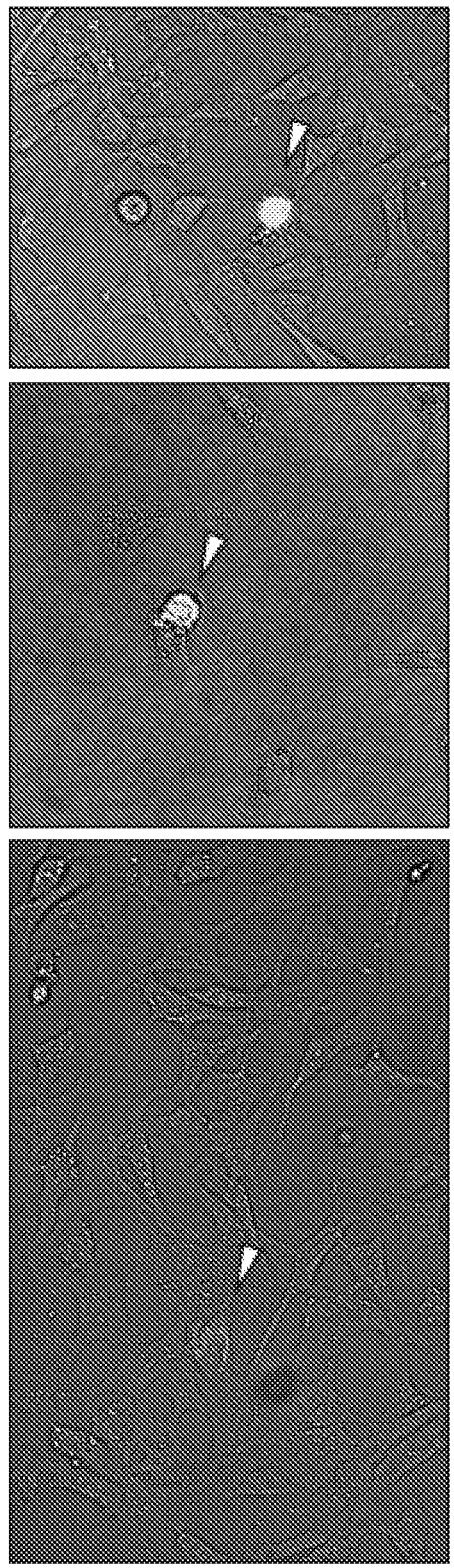
FIG. 7A  FIG. 7B  FIG. 7C  FIG. 7D  FIG. 7E

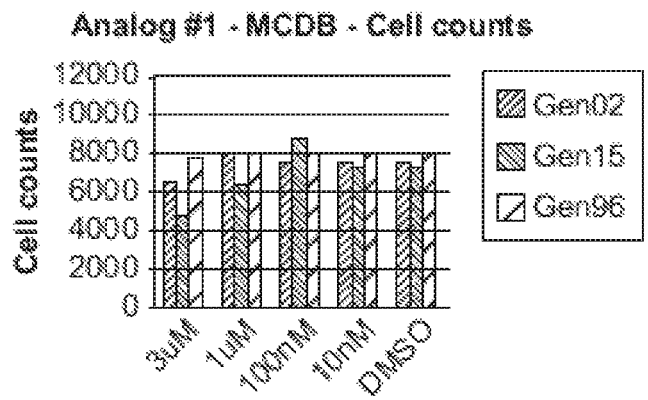
FIGURE 9A
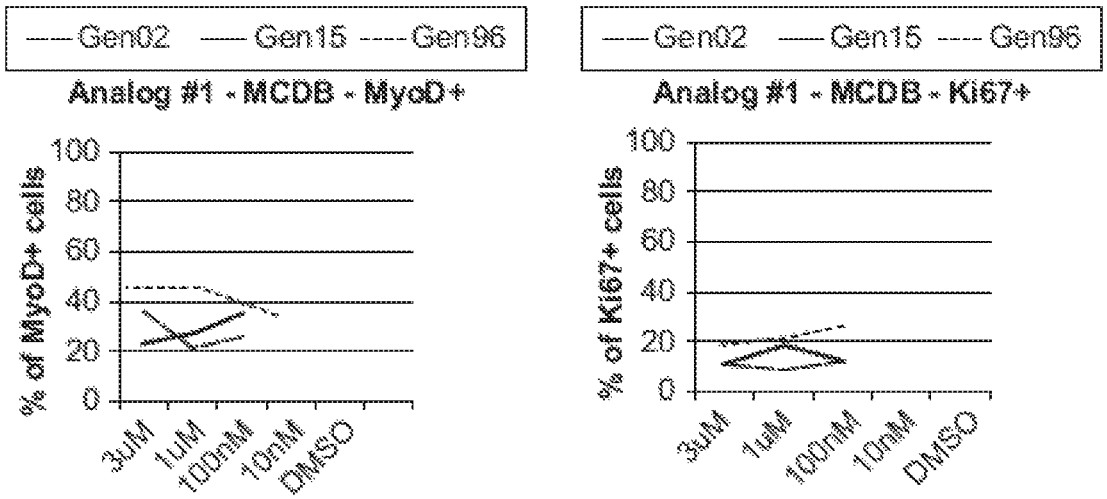
FIG. 9B
FIG. 9C
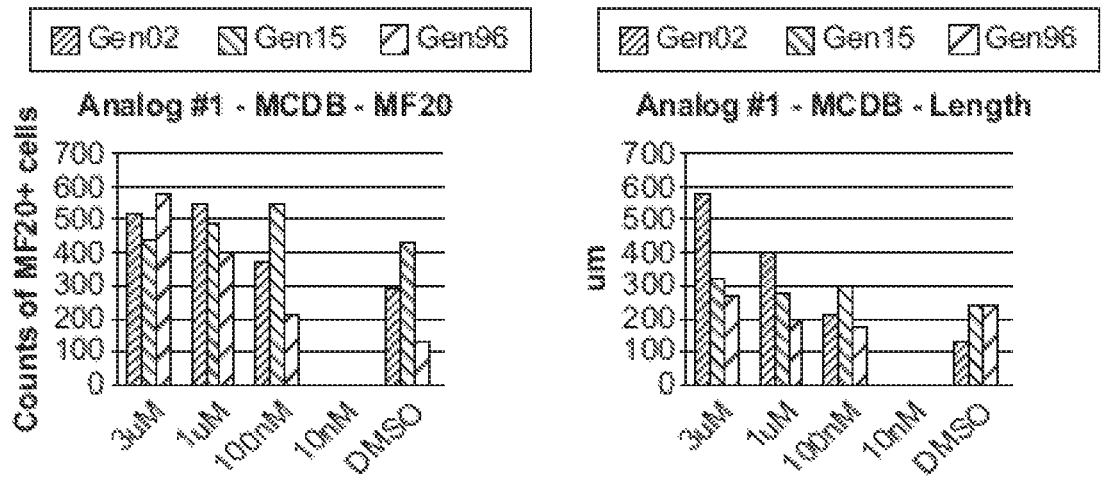
FIG. 9D
FIG. 9E

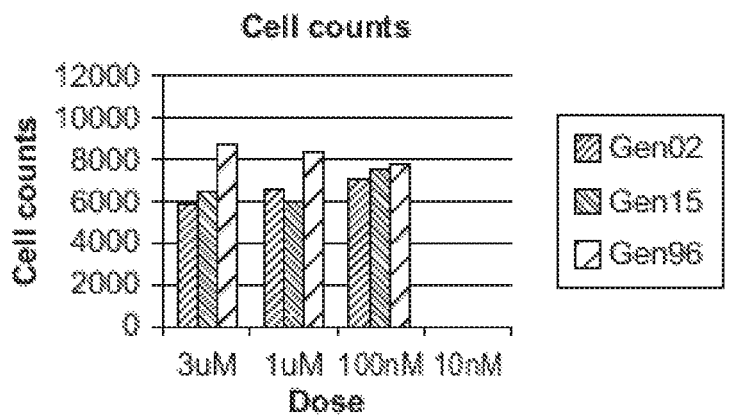
FIG. 10A
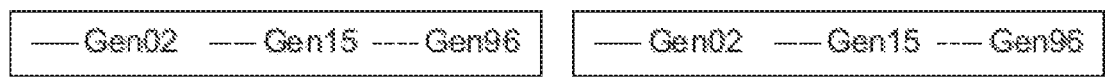
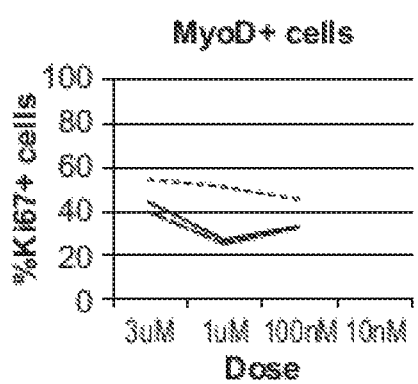
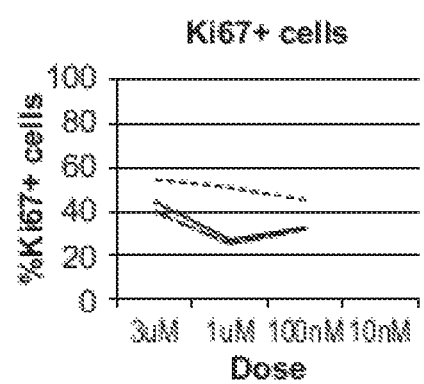
FIG. 10B      FIG. 10C
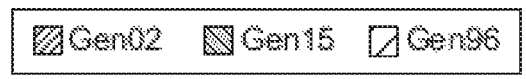
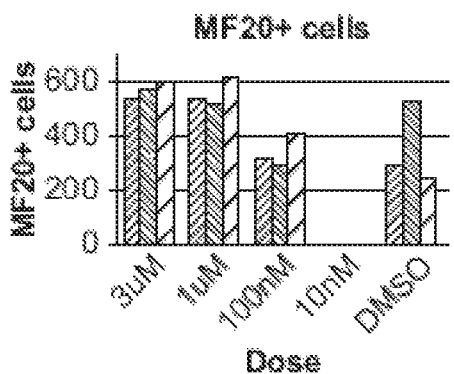
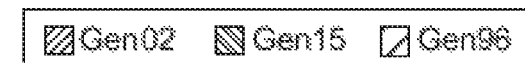
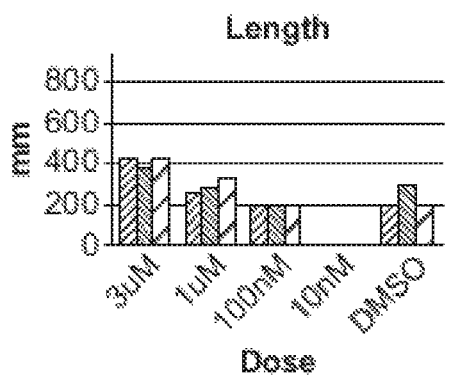
FIG. 10D      FIG. 10E

MODULATORS OF DUX4 FOR REGULATION OF MUSCLE FUNCTION

CROSS-REFERENCE

This application is a national stage entry of PCT Application No. PCT/AU2017/050498, filed May 26, 2017; which claims priority to U.S. Provisional Application No. 62/460,186, filed Feb. 17, 2017; and claims priority to U.S. Provisional Application No. 62/342,143, filed May 26, 2016; which are incorporated herein by reference in their entirety and to which applications priority is claimed under 35 USC § 120.

BACKGROUND

Facioscapulohumeral dystrophy (FSHD) is a neuromuscular disease with a prevalence that could reach 1 in 8,000. It is typically characterized by progressive asymmetric muscle weakness. Manifestation of the disease includes both typical and asymmetric patterns of muscle involvement and disease progression. Two forms of FSHD have been identified: FSHD1 and FSHD2. Although both forms may display identical clinical phenotypes, it is unclear whether their genetic and epigenetic origins overlap or are distinct. To date, the exact nature of pathophysiology of FSHD has not been established. As a result, target or pathway-biased treatment for this disease is not believed to be available. There is a need in the art for effective treatments for FSHD.

Chromatin is a complex of macromolecules (including DNA, protein, and RNA) with functions that include the packaging of DNA into smaller volumes to fit into a cell nucleus, and the control of gene expression. Histones are the major protein component of chromatin and bind DNA into protein-DNA complexes called nucleosomes. Epigenetic modifications (e.g., methylation, acetylation, ubiquitination, neddylation, phosphorylation) of histones, DNA and other macromolecules may regulate chromatin compaction by causing the loosening or condensing chromatin, thereby affecting the ability of regulatory factors to access DNA. Additionally, a number of non-coding RNAs, such as DBE-T, play a role as epigenetic modifiers. Epigenetic modifications are generally processed by a large number of "epigenetic modifiers" that are broadly classified by their functions as "writers," "readers," and "erasers" that, respectively, add, detect by binding, or remove various chemical modifications.

SUMMARY

The present disclosure provides methods and compositions for the treatment of facioscapulohumeral muscular dystrophy (FSHD). In some cases, the methods and compositions involve the use of methyltransferase inhibitors (e.g., histone methyltransferase inhibitors) to inhibit or repress DUX4 expression in muscle cells, particularly in subjects that have FSHD, a muscle disease or deficiency, or any disease or disorder associated with upregulated DUX4 expression. Further disclosed herein are methods and cell based assays for screening compounds for the treatment of facioscapulohumeral muscular dystrophy or other muscular disease or disorder.

An aspect of the disclosure provides a method of treating facioscapulohumeral muscular dystrophy (FSHD) or ataxia in a subject in need thereof, the method comprising: administering to the subject in need thereof a therapeutically effective amount of a compound of Formula (I):

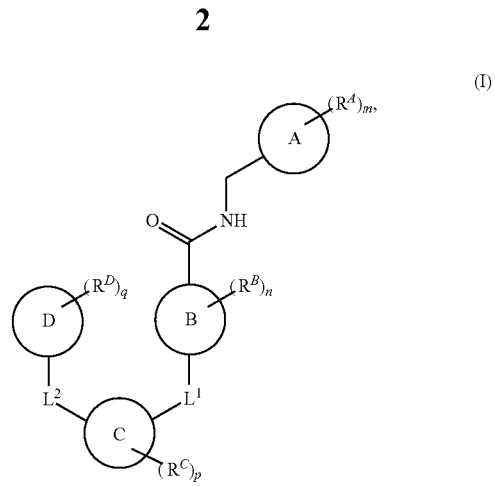

or a pharmaceutically acceptable salt thereof, wherein:
A is selected from $C_{5-12}$ carbocycle and 5- to 12-membered heterocycle;
B is selected from $C_{5-12}$ carbocycle and 5- to 12-membered heterocycle;
C is selected from bond, $C_{5-12}$ carbocycle, and 5- to 12-membered heterocycle;
D is selected from bond, $C_{5-12}$ carbocycle, and 5- to 12-membered heterocycle;
each of $L^1$ and $L^2$ is independently selected from bond, —O—, —S—, —N($R^{51}$)—, —N($R^{51}$)$CH_2$—, —C(O)—, —C(O)O—, —OC(O)—, —OC(O)O—, —C(O)N($R^{51}$)—, —C(O)N($R^{51}$)C(O)—, —C(O)N($R^{51}$)C(O)N($R^{51}$)—, —N($R^{51}$)C(O)—, —N($R^{51}$)C(O)N($R^{51}$)—, —N($R^{51}$)C(O)O—, —OC(O)N($R^{51}$)—, —C(N$R^{51}$)—, —N($R^{51}$)C(N$R^{51}$)—, —C(N$R^{51}$)N($R^5$)—, —N($R^{51}$)C(N$R^{51}$)N($R^5$)—, —S(O)$_2$—, —OS(O)—, —S(O)O—, —S(O)—, —OS(O)$_2$—, —S(O)$_2$O—, —N($R^{51}$)S(O)$_2$—, —S(O)$_2$N($R^{51}$)—, —N($R^{51}$)S(O)—, —S(O)N($R^{51}$)—, —N($R^{51}$)S(O)$_2$N($R^{51}$)—, and —N($R^{51}$)S(O)N($R^{51}$)— or from alkylene, alkenylene, alkynylene, heteroalkylene, heteroalkenylene, and heteroalkynylene, each of which is optionally substituted with one or more $R^{50}$;
$R^{50}$ is, at each occurrence, independently selected from: halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$—NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$);
$C_{1-10}$ alkyl, $C_{2-10}$ alkenyl, and $C_{2-10}$ alkynyl, each of which is independently optionally substituted at each occurrence with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)N(R$^{52}$)$_2$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$) (R$^{52}$), —NR$^{52}$P(O)(R$^{52}$), —P(O)(R$^{52}$)(OR$^{52}$), —P(O)(NR$^{52}$)$_2$, =O, =S, =N(R$^{52}$), C$_{3-12}$ carbocycle, and 3- to 12-membered heterocycle; and C$_{3-12}$ carbocycle and 3- to 12-membered heterocycle, wherein each C$_{3-12}$ carbocycle and 3- to 12-membered heterocycle in R$^{50}$ is independently optionally substituted with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$ NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O) NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$) (R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$), C$_{1-6}$ alkyl, C$_{1-6}$ haloalkyl, C$_{2-6}$ alkenyl, and C$_{2-6}$ alkynyl;

R$^{51}$ is independently selected at each occurrence from: hydrogen, —C(O)R$^{52}$, —C(O)OR$^{52}$, —C(O)N(R$^{52}$)$_2$, —C(O)NR$^{53}$R$^{54}$;

C$_{1-6}$ alkyl, C$_{2-6}$ alkenyl, and C$_{2-6}$ alkynyl, each of which is independently optionally substituted at each occurrence with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O) OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$) (R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$), C$_{3-12}$ carbocycle and 3- to 12-membered heterocycle; and C$_{3-12}$ carbocycle and 3- to 12-membered heterocycle, wherein each C$_{3-12}$ carbocycle and 3- to 12-membered heterocycle in R$^{51}$ is independently optionally substituted with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$ NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$) (R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$), C$_{1-6}$ alkyl, C$_{1-6}$ haloalkyl, C$_{2-6}$ alkenyl, and C$_{2-6}$ alkynyl;

R$^{52}$ is independently selected at each occurrence from hydrogen; and C$_{1-20}$ alkyl, C$_{2-20}$ alkenyl, C$_{2-20}$ alkynyl, 1- to 6-membered heteroalkyl, C$_{3-12}$ carbocycle, and 3- to 12-membered heterocycle, each of which is optionally substituted by halogen, —CN, —NO$_2$, —N$_3$, —NHCH$_3$, —NHCH$_2$CH$_3$, =O, —OH, —OCH$_3$, —OCH$_2$CH$_3$, C$_{3-12}$ carbocycle, or 3- to 6-membered heterocycle;

R$^{53}$ and R$^{54}$ are taken together with the nitrogen atom to which they are attached to form a heterocycle, optionally substituted with one or more R$^{50}$;

each of R$^A$, R$^B$, and R$^C$ is independently selected from R$^{50}$;

R$^D$ is, at each occurrence, independently selected from hydrogen or R$^{50}$; and each of m, n, p, and q is independently an integer from 0-12, thereby treating facioscapulohumeral muscular dystrophy (FSHD) or ataxia in the subject. In a preferred aspect this disclosure provides a method of treating FSHD in a subject in need thereof. In another preferred aspect, this disclosure provides a method of treating a disease or disorder associated with upregulated DUX4 expression in a subject in need thereof.

In some embodiments, A is 6-membered heterocycle. In some embodiments, A is pyridonyl. In some cases of the methods of any of the preceding, B is selected from 6- to 10-membered heteroaryl. In some embodiments, B is selected from indolyene, indazolylene, and phenylene. In some embodiments, C is selected from from pyridinylene, phenylene, tetrahydropyranylene, and piperidinylene. In some embodiments, D is selected from bond and 6-membered heterocycle. In some embodiments, D is selected from piperazinyl and morpholinyl.

In some embodiments, this disclosure provides methods of treating FSHD in a subject in need thereof, comprising administering to the subject in need thereof a compound of Formula (II)

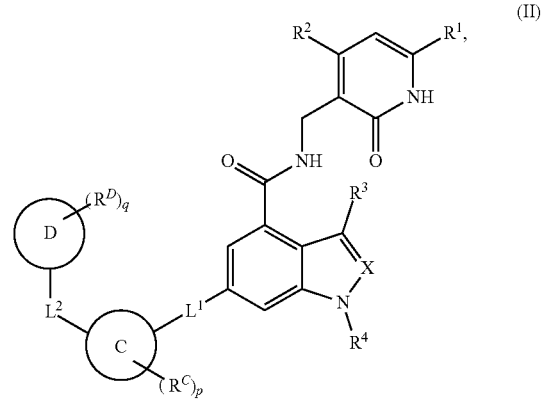

or a pharmaceutically acceptable salt thereof, wherein:
X is C—R$^5$ or N;
each of R$^1$ and R$^2$ is independently R$^{50}$;
R$^3$ is selected from hydrogen and R$^{50}$;
R$^4$ is R$^{52}$; and
R$^5$ is selected from hydrogen and R$^{50}$. In some embodiments, the R$^3$ is H or —CH$_3$. In some embodiments, R$^4$ is C$_{1-5}$ alkyl or C$_{1-5}$ carbocycle. In some embodiments, L$^1$ is a bond. In some embodiments, L$^2$ is a bond. In some embodiments, L$^2$ is C$_{1-3}$ alkylene. In some embodiments, C is a 6-membered aryl or 6-membered heteroaryl. In some embodiments, C is a pyridinylene or phenylene. In some embodiments, D is a 6-membered heterocycle. In some embodiments, D is piperazinyl or morpholinyl, thereby treating FSHD in the subject in need thereof.

In some embodiments, this disclosure provides methods of treating FSHD in a subject in need thereof, comprising administering to the subject in need thereof a compound of Formula (III):

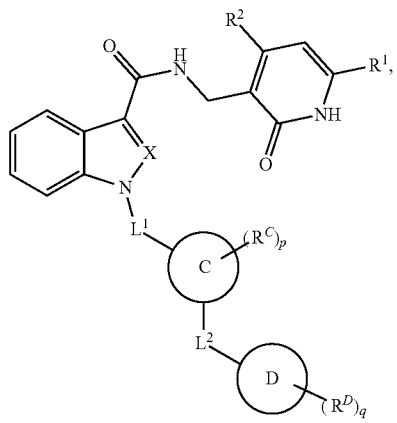

(III)

or a pharmaceutically acceptable salt thereof, wherein:
X is C—$R^5$ or N;
each of $R^1$ and $R^2$ is independently $R^{50}$; and
$R^5$ is selected from hydrogen and $R^{50}$. In some embodiments, $L_1$ is

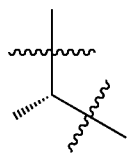

In some embodiments, C is piperidinylene or morpholinylene. In some embodiments, p is 0. In some embodiments, D is a bond. In some embodiments, X is C—H. In some embodiments, X is N. In some embodiments, $R^1$ is —$CH_3$. In some embodiments $R^2$ is $C_{1-3}$ alkyl or —$OR^{52}$. In some embodiments, $R^2$ is —$CH_3$, —$CH_2CH_2CH_3$, or —$OCH_3$. In some embodiments, $R^2$ is —$CH_3$, thereby treating FSHD in the subject in need thereof.

In some embodiments of the disclosure, B is a 6-membered aryl. In some embodiments, B is phenylene. In some embodiments, C is a 6-membered aryl. In some embodiments, C is phenylene. In some embodiments, D is 6-membered heterocycle. In some embodiments, D is morpholinyl. In some embodiments, the compound is selected from the group consisting of

EPZ005687 of

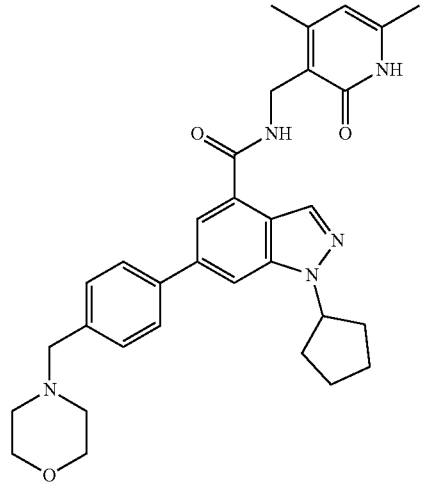

GSK343

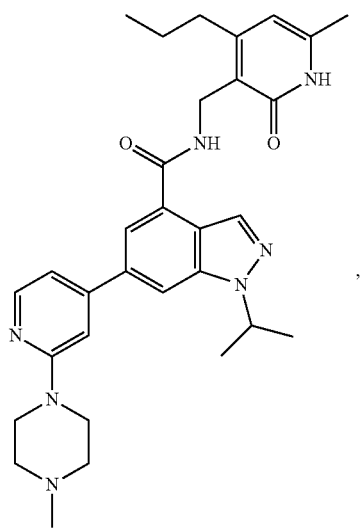

EI-1

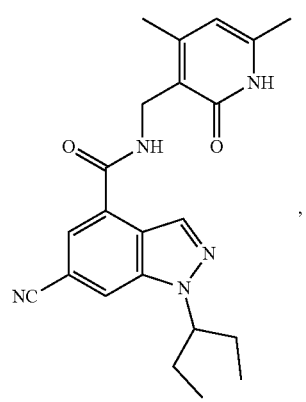

CPI-360

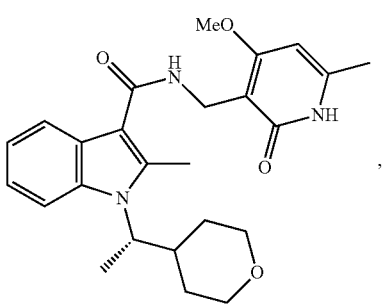

CPI-169

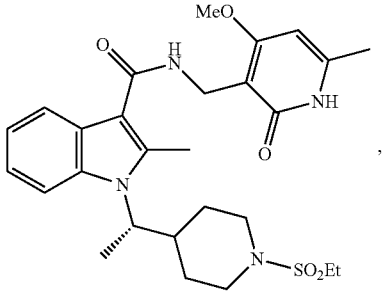

-continued

UNC1999

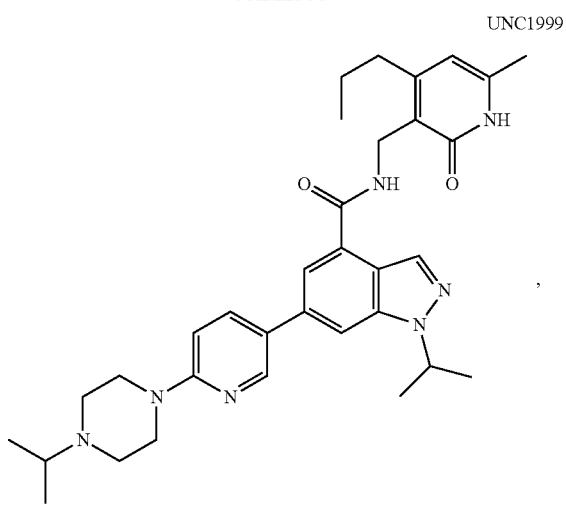

GSK126 (ASK19)

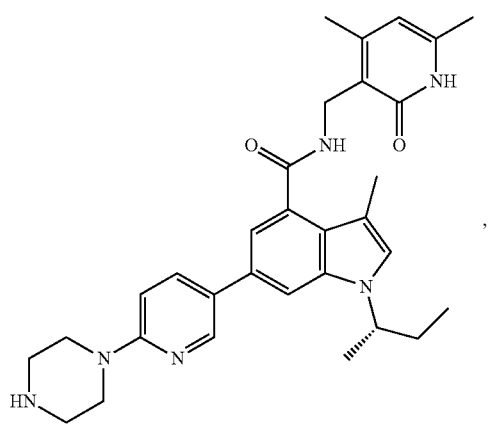

GSK503

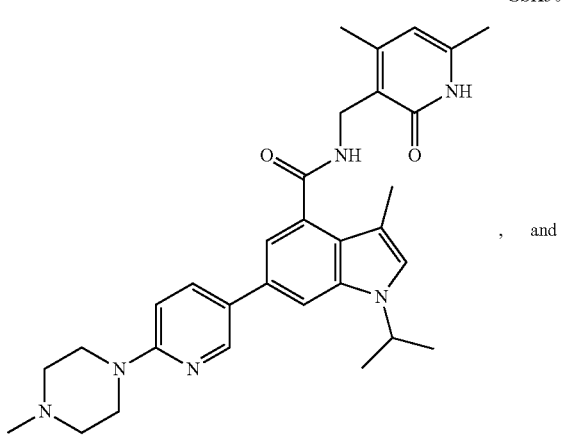

, and

-continued

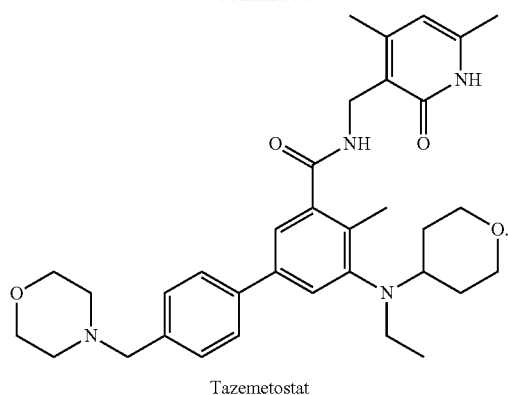

Tazemetostat

In another aspect, this disclosure provides methods of treating facioscapulohumeral muscular dystrophy (FSHD) in a subject in need thereof, the method comprising: administering to the subject a therapeutically effective amount of a compound selected from the group consisting of

EPZ5676

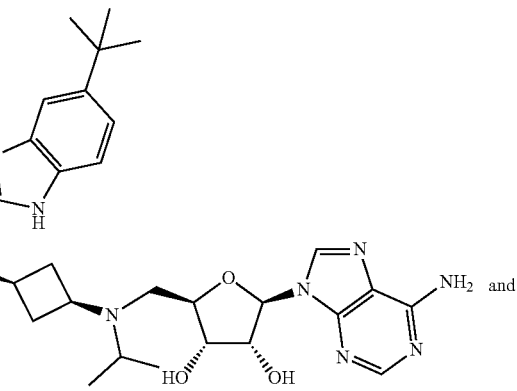 and

BIX01294

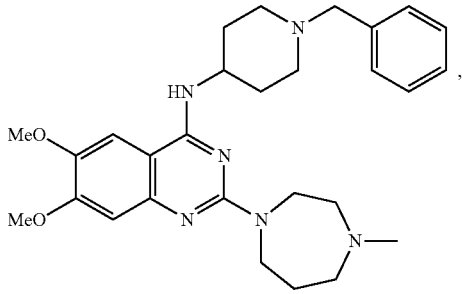

thereby treating facioscapulohumeral muscular dystrophy (FSHD) in the subject in need thereof. In another aspect, this disclosure provides methods of treating ataxia in a subject in need thereof, the method comprising: administering to the subject a therapeutically effective amount of a compound selected from the group consisting of

EPZ5676

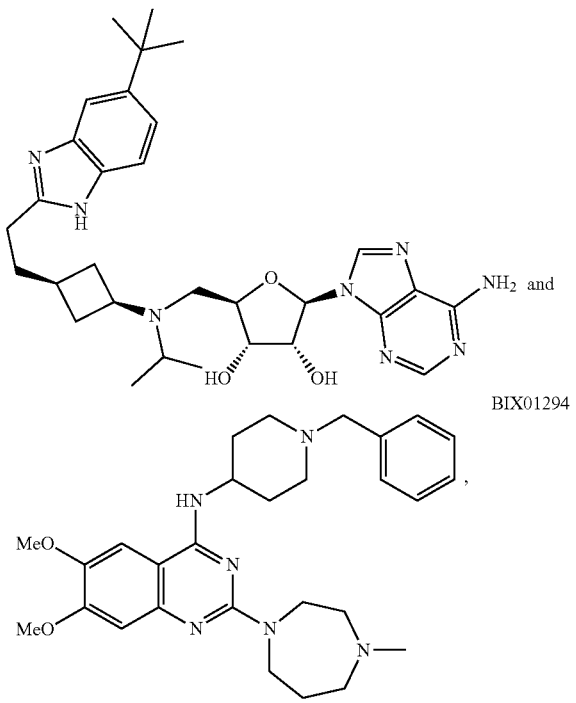

BIX01294 thereby treating ataxia in the subject in need thereof.

In some cases of the methods of any of the preceding, the method further comprises administering to the subject a second therapeutic agent. In some cases of the methods of any of the preceding, the method further comprises administering to the subject a cell therapy. In some cases of the methods of any of the preceding, the subject is human. In some embodiments of the methods of any of the preceding, the compound is of the formula:

GSK126 (ASK19)

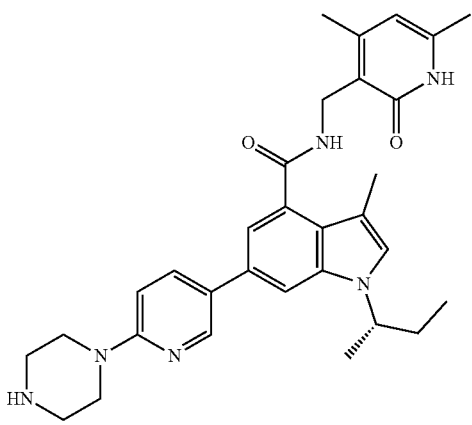

A further aspect of the disclosure provides a kit comprising a pharmaceutical composition comprising a compound of Formula (I) and packaging materials. In some embodiments, the kit includes instructions for using the composition to treat a subject suffering from facioscapulohumeral muscular dystrophy (FSHD). In some cases, the kit comprises a vial, tube, or plastic container comprising a compound of Formula (I) and a separate component containing a second material, such as another compound, a reagent, an injection device, or packaging materials.

An additional aspect of the disclosure provides a method of determining D4Z4 de-repression activity of a compound in a cell, comprising: administering a DNA methyltransferase inhibitor to the cell, thereby inducing DUX4 expression in the cell; administering a compound to the cell; and measuring DUX4 expression, thereby determining D4Z4 de-repression activity of the compound in the cell. In some embodiments, the DNA methyltransferase inhibitor is a nucleoside analogue. In some embodiments, the nucleoside analogue is a ribonucleoside analogue. In some embodiments, the nucleoside analogue is a deoxyribonucleoside analogue. In some embodiments, the nucleoside analogue is an adenosine or deoxyadenosine analogue. In some embodiments, the nucleoside analogue is a guanosine or deoxyguanosine analogue. In some embodiments, the nucleoside analogue is a uridine or thymidine analogue. In some embodiments, the nucleoside analogue is a cytidine or deoxycytidine analogue. In some embodiments, the nucleoside analogue is decitabine or azacitidine. In some embodiments, the nucleoside analogue is selected from Table 2.

In some embodiments, this disclosure provides methods of determining D4Z4 de-repression activity of a muscle lineage cell. In some embodiments, the muscle lineage cell is selected from the group consisting of skeletal muscle cell, muscle precursor cell, myotube, myoblast, and satellite cell.

Another aspect of the disclosure provides a method of treating facioscapulohumeral muscular dystrophy (FSHD) in a subject in need thereof, comprising: administering a therapeutically effective amount of a histone methyltransferase inhibitor to a subject with symptoms of FSHD, thereby reducing the symptoms of FSHD in the subject. In some embodiments, the subject has facioscapulohumeral muscular dystrophy (FSHD). In some embodiments, the subject is suspected of having facioscapulohumeral muscular dystrophy (FSHD). In some embodiments, the subject is human. In some cases of the methods of the preceding, the histone methyltransferase inhibitor is administered to the subject orally, intravenously, intramuscularly, subcutaneously, or transdermally, or combination thereof.

Another aspect of the disclosure provides a method of treating a muscle disease or disorder that is not Duchenne muscular dystrophy, muscular dystrophy, or myotonic dystrophy, comprising: administering a therapeutically effective amount of a compound of Formula (I) to a subject with a muscle disease that is not Duchenne muscular dystrophy, muscular dystrophy, or myotonic dystrophy, thereby treating the muscle disease of the subject, wherein the muscle disease is not Duchenne muscular dystrophy, muscular dystrophy, or myotonic dystrophy. In some cases of the method of the preceding the subject has symptoms of facioscapulohumeral muscular dystrophy (FSHD).

A further aspect of the disclosure provides a method of reducing DUX4 expression in a subject with symptoms of facioscapulohumeral muscular dystrophy (FSHD), comprising: administering a histone methyltransferase inhibitor to the subject with FSHD symptoms, thereby reducing expression of DUX4 in the subject with FSHD symptoms. In some embodiments, the reduction of expression of DUX4 occurs in skeletal muscle of the subject. In some embodiments, the subject has facioscapulohumeral muscular dystrophy (FSHD). In some embodiments, the subject is suspected of having facioscapulohumeral muscular dystrophy (FSHD). In some embodiments, the subject is human. In some embodiments, the histone methyltransferase inhibitor is administered to the subject orally, intravenously, intramuscularly, subcutaneously, transdermally, or any combination thereof.

In some embodiments of the methods of any of the preceding, the method further comprises monitoring the subject for reduction in symptoms of facioscapulohumeral muscular dystrophy (FSHD). In some cases, the method further comprises monitoring the subject for reduction in DUX4 expression.

INCORPORATION BY REFERENCE

All publications, patents, and patent applications mentioned in this specification are herein incorporated by reference in their entireties and to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 7A-E show the DUX4 reporter in FSHD-affected stem cell lines 8 days after myogenic induction; DUX4-positive nuclei were observed in a small portion of FSHD-affected satellite-like cell cultures from GENEA050 (7A, 7B) and GENEA096 (7C, 7D, and 7E); some examples of DUX4-expressing cells are marked with arrows;

FIGS. 9A-9E illustrate the effects of a DNA methyltransferase inhibitor (Compound #1A1, an analogue of Compound #1) on cell count 9A; MyoD expression 9B; Ki67 expression 9C; and MF20 expression 9D; as well as myotube length 9E in cells treated with Compound #1A1 for 24 hours at the beginning of the myoblast stage;

FIGS. 10A-10E illustrate the effects of a histone methyltransferase inhibitor, ASK19 (Compound #2) on cell count 10A; MyoD expression 10B; Ki67 expression 10C; MF20 expression 10D; and myotube length 10E in cells treated with Compound #2 for 24 hours at the beginning of the myoblast stage.

DETAILED DESCRIPTION

I. Overview

Figure 1:
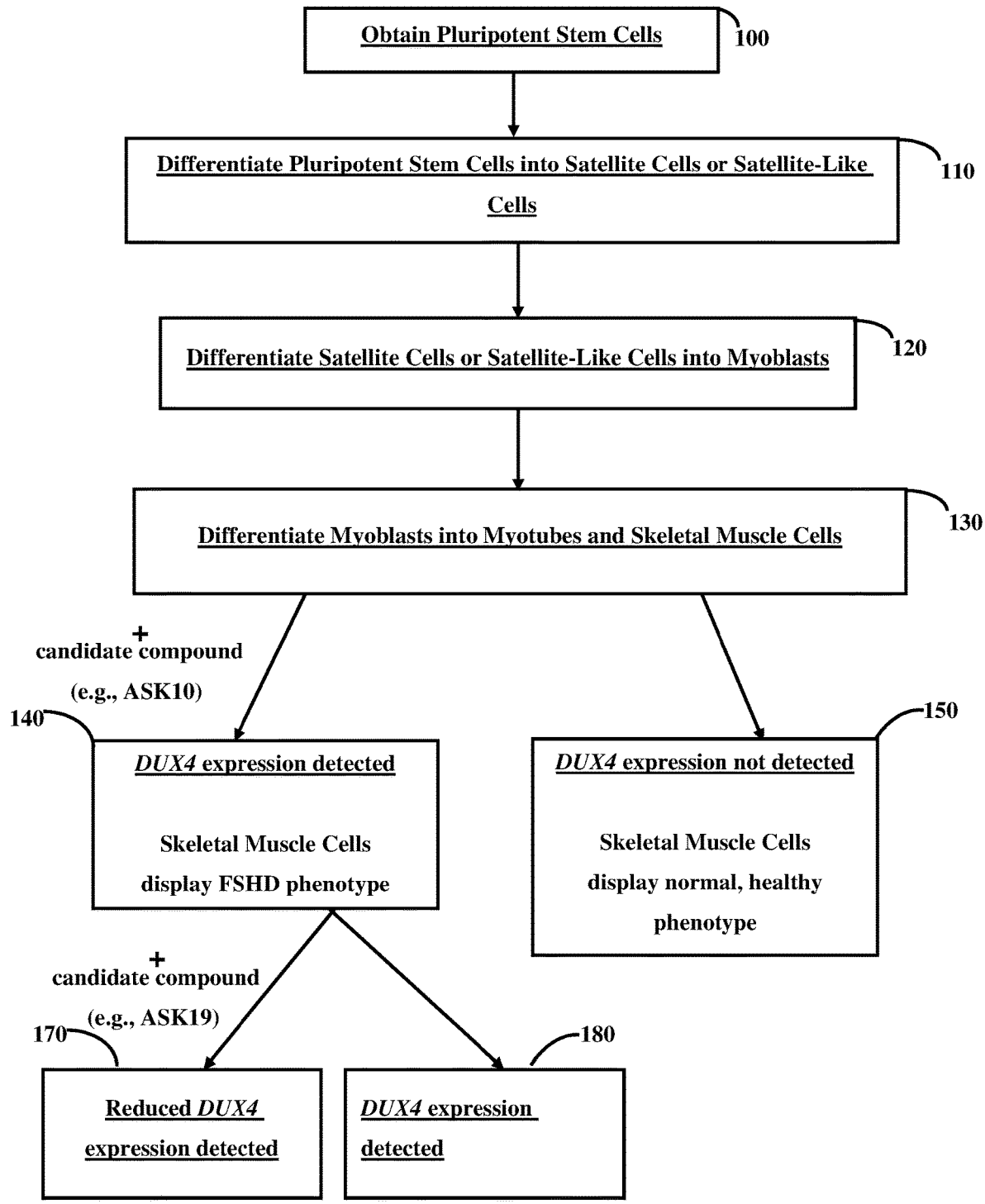
FIG. 1 is an overview depicting drug screening assays for compounds that upregulate DUX4 and for candidate therapeutic compounds that downregulate DUX4 expression.

The present disclosure describes the use of histone methyltransferase (HMT) inhibitors (e.g., GSK126, a compound of Table 1, or a compound of any one of Formulas (I), (II), or (III)) to treat subjects with muscular deficiencies such as facioscapulohumeral muscular dystrophy (FSHD) and/or to treat subjects with diseases or disorders associated with upregulated DUX4 expression. The HMT inhibitors may be administered alone or in combination with other compounds or therapies such as a cell therapy. The present disclosure also provides agents (e.g., DNA methyltransferase modulators, decitabine) that upregulate DUX4 in muscle cells in vitro, thereby simulating FSHD since—without wishing to be bound by theory—FSHD is associated with upregulation of DUX4 expression in muscle cells. This disclosure also provides cell-based assays to identify candidate compounds that upregulate DUX4 expression in muscle cells, as well as to identify candidate drugs that reduce or eliminate DUX4 expression.

Examples of methyltransferase inhibitors that may be used in the present methods and compositions include decitabine and analogues thereof, GSK126 and analogues thereof, a compound of Table 1, or a compound of any one of Formulas (I), (II), or (III). In some cases, the methods may include use of decitabine (or analogues thereof) to upregulate DUX4. In some cases, the methods may include use of GSK126, a compound of Table 1, or a compound of any one of Formulas (I), (II), or (III) to downregulate DUX4.

The compounds, methods and compositions disclosed herein may be used to treat subjects with muscular degenerative diseases or muscular disorders stemming from a variety of causes, including, but not limited to, genetic disorders, sporadic diseases, cachexia, muscle strain, muscle injury, muscle atrophy, as well as sarcopenia and the general aging process. The disclosed compounds may be administered to a subject by a variety of routes, including but not limited to, orally, intravenously, intramuscularly, subcutaneously, and transdermally. Without wishing to be bound by theory, the compounds may block de-repression or activation of DUX4 and/or interfere with the activity of DUX4 subsequent to de-repression. As a result of administration of compounds provided herein (e.g., GSK126, a compound of Table 1, or a compound of any one of Formulas (I), (II), or (III)), subjects may experience improvements in muscle strength, performance, stamina and reduced symptoms of muscle weakness, particularly subjects with a disease or disorder associated with upregulated DUX4 expression or FSHD.

Often, the cell-based assays provided herein use DUX4 expression as a read-out. In some instances, the candidate therapeutics may specifically modulate DUX4 expression. Often, the one or more candidate therapeutics may be epigenetic modulators or epigenetic signaling machinery molecules, including, but not limited to: epigenetic writers (e.g., DNA methyltransferases, histone acetyltransferases, histone methyltransferases, and serine/threonine kinases); epigenetic readers (e.g., MeCP2, MBD1, MBD2, MBD3, BRD2, BRD3, BRD4, Bdf, Brg), chromodomain proteins (e.g., HP-1 like, polycomb-like, CHD-like), Tudor domain proteins (e.g., SMN), PHD finger proteins (e.g., CBD, ING2, DNMT3L, PHF6), 14-3-3 proteins; epigenetic erasers (e.g., MBD, TET, HDAC Classes I-IV, lysine demethylases, protein phosphatases, PARP, HIF, Pim, Aurora kinases), or a combination thereof.

II. Subjects to be Treated

The subjects treated by the methods and compositions provided herein may have or may be suspected of having any of a number of muscular degenerative diseases and muscular disorders. The methods and compositions herein may thus include methods or compositions for treating a subject suffering or suspected to be suffering from FSHD or other muscular or neuromuscular dystrophy. In some cases, the muscular dystrophy is facioscapulohumeral muscular dystrophy-1 (FSHD1). In some cases, the muscular dystrophy is facioscapulohumeral muscular dystrophy-2 (FSHD2). In some cases the muscular or neuromuscular dystrophy is one of the following disorders: Becker muscular dystrophy, Duchenne muscular dystrophy, myotonic dystrophies types 1 and 2, nemaline myopathy or spinal muscular atrophy. In some cases the muscular disease is not Duchenne muscular dystrophy, muscular dystrophy, or myotonic dystrophy. In some cases, the subject has a disease or disorder associated with upregulated DUX4 expression, and the disease or disorder is treated by administering a compound provided herein to the subject.

The subjects are preferably human subjects or patients, but in some cases may be non-human subjects, (e.g., non-human mammals). Examples of non-human mammals include, but are not limited to, non-human primates (e.g., apes, monkeys, gorillas), rodents (e.g., mice, rats), cows, pigs, sheep, horses, dogs, cats, and rabbits.

Subjects who may benefit from the methods and compositions provided herein may be suffering or suspected to be suffering from FSHD or other muscular or neuromuscular dystrophy at any stage of disease. For example, such subjects may be suffering from FSHD at an early stage of pathogenesis and may even be unaware of disease symptoms. In some cases, a subject may have other symptoms that may appear early in the pathogenesis of FSHD, such as weakness around the eyes and/or the mouth, an inability to purse or pucker the lips, a difficulty with turning up the corners of the mouth when smiling, and an inability to close the eyes. Subjects who may benefit from treatment according to the methods and compositions provided herein may be suffering from FSHD at an intermediate stage of pathogenesis. Such subjects may experience muscle pain and aching, including, but not limited to aching in the area around the shoulders; a loss of stability around the shoulders, including, but not limited to a loss of stability that impedes the subject's ability to throw objects or lift the arms above the head; and/or unequal muscle weakening, including, but not limited to the biceps, triceps, deltoids, and lower arm muscles. In some cases, subjects who may benefit from treatment according to the methods and compositions provided herein may be suffering from FSHD at a late stage of pathogenesis. Such subjects may experience weakening of abdominal muscles and hip muscles, which may lead to an exaggerated curvature of the lower spine; and/or weakening of muscles throughout the body, including, but not limited to muscles of the foot, ankle, hips, and abdomen.

Subjects in need of treatment according to the methods and compositions provided herein may be male or female. Subjects may include adults, teenagers, adolescents, children, toddlers, infants, and neonates. Such subjects may be of a range of ages, which may include >10 minutes old, >1 hour old, >1 day old, >1 month old, >2 months old, >6 months old, >1 year old, >2 years old, >5 years old, >10 years old, >15 years old, >18 years old, >25 years old, >35 years old, >45 years old, >55 years old, >65 years old, >80 years old, <80 years old, <70 years old, <60 years old, <50 years old, <40 years old, <30 years old, <20 years old or <10 years old. The subject may be a neonatal infant. In some cases, the subject is a child or an adult. In some examples, the subject is a human of age 2, 5, 10 or 20 hours. In other examples, the subject is a human of age 1 month, 2 months, 3 months, 4 months, 5 months, 6 months, 9 months or 12 months. In some cases, the subject is a human of age 1 year, 2 years, 3 years, 4 years, 5 years, 18 years, 20 years, 21 years, 23 years, 24 years, 25 years, 28 years, 29 years, 31 years, 33 years, 34 years, 35 years, 37 years, 38 years, 40 years, 41 years, 42 years, 43 years, 44 years, 47 years, 51 years, 55 years, 61 years, 63 years, 65 years, 70 years, 77 years, or 85 years. Subjects may have differing genetic backgrounds, including different racial groups or genetically admixed populations.

III. Therapeutic Chemical Agents

The methods provided herein include administering a therapeutic agent (e.g., DNA methyltransferase inhibitors, histone methyltransferase inhibitors, GSK126 or analogue thereof, a compound of Table 1, or a compound of any one of Formulas (I), (II), or (III)) to a subject. Therapeutic agents administered to subjects in the present disclosure may include, but are not limited to, small molecules, organic compounds, peptides, peptoids, peptide nucleic acids, antisense oligonucleotides, RNAs and aptamers. Therapeutic agents administered to subjects may include one or more compounds that may target molecules in various signaling pathways and networks related to FSHD, including but not limited to DUX4 expression, epigenetic signaling machinery networks, Wnt/Fz/beta-catenin signaling pathways, telomere structure and telomerase activity pathways, kinome signaling networks, cytoskeleton structure and JAK/STAT signaling pathways, cell cycle signaling pathways, apoptosis signaling pathways, metabolic signaling pathways, and ubiquitin signaling pathways.

In some cases the therapeutic agent may include one or more compounds that activate or inhibit enzymes. In some cases the therapeutic agent may include one or more compounds that are pharmacologically-specific modulators, including, but not limited to agonists, partial agonists, antagonists, competitive modulators, and non-competitive modulators.

Epigenetic Modulators

In some cases, the therapeutic agent administered to the subject may include a compound or compounds that target epigenetic modifiers. In preferred embodiments, the therapeutic agent is a histone methyltransferase inhibitor (e.g., GSK126 and analogues thereof, a compound of Table 1, or a compound of any one of Formulas (I), (II), or (III)). The therapeutic agent may disrupt the mechanism of action of epigenetic modifiers, including, but not limited to DNA methyltransferases, histone acetyltransferases, histone methyltransferases, and histone deacetylases. In some cases, without wishing to be bound by theory, the therapeutic agent may disrupt the mechanism of action of epigenetic modifiers by inhibiting methyltransferase enzymes. In some cases, the therapeutic agent may disrupt the mechanism of action of epigenetic modifiers by activating methyltransferase enzymes. In some cases, the therapeutic agent may disrupt the mechanism of action of epigenetic modifiers by inhibiting acetyltransferase enzymes. In some cases, the therapeutic agent may disrupt the mechanism of action of epigenetic modifiers by activating acetyltransferase enzymes. In some cases, the therapeutic agent may disrupt the mechanism of action of epigenetic modifiers by inhibiting deacetylase enzymes. In some cases, the therapeutic agent may disrupt the mechanism of action of epigenetic modifiers by activating deacetylase enzymes. In some cases, the therapeutic agent may disrupt the mechanism of action of epigenetic modifiers by activating transcription of an epigenetic modifier. In some cases, the therapeutic agent may disrupt the mechanism of action of epigenetic modifiers by inhibiting transcription of an epigenetic modifier.

The therapeutic agent may include one or more compounds that target epigenetic modifiers that may be broadly classified by their functions as 'writers,' 'readers,' and 'erasers' of chemical modifications. The therapeutic agent may include one or more compounds that target epigenetic modifiers, including, but not limited to compounds that target epigenetic writers, epigenetic readers, and epigenetic erasers.

Epigenetic writers are generally enzymes that add chemical modifications to molecules. In some cases, epigenetic writers may covalently modify histone proteins. In some cases, epigenetic writers may covalently modify histone proteins by transferring at least one acetyl group to a histone protein. In some cases, epigenetic writers may covalently modify histone proteins by transferring at least one methyl group to a histone protein. In some cases, epigenetic writers may directly modify DNA molecules. In some cases, epigenetic writers may modify DNA molecules by transferring at least one methyl group to the DNA. Epigenetic writers may include, but are not limited to, DNA methyltransferases, histone acetyltransferases, histone methyltransferases, and kinases.

Inhibitors of epigenetic writers include compounds that inhibit the activity of methyltransferase enzymes. Inhibitors of epigenetic writers include, but are not limited to compounds that are DNA methyltransferase inhibitors and histone methyltransferase inhibitors. In some cases, histone methyltransferase inhibitors reversibly bind to histone methyltransferase enzymes. In some cases, histone methyltransferase inhibitors disrupt the binding site for a cofactor or cofactors in the histone methyltransferase enzyme.

Epigenetic readers are generally proteins that detect and bind chemical modifications. In some cases, epigenetic readers may detect and bind acetyl groups. In some cases, epigenetic readers may detect and bind methyl groups. In some cases, epigenetic readers may specifically detect and bind methylated DNA. In some cases, epigenetic readers may specifically detect and bind methylated histone proteins. In some cases, epigenetic readers may detect and bind histone proteins that have more than one chemical modification. Epigenetic readers may contain domains that recognize specific chemical modifications, including, but not limited to chromodomains, bromodomains, Tudor domains, PHD finger domains, and DNA methyl-binding domains. Examples of epigenetic readers include but are not limited to bromodomain and extraterminal (BET) proteins, chromodomain proteins, Tudor domain proteins, PHD finger proteins, and 14-3-3 proteins.

Epigenetic erasers are generally enzymes that remove chemical modifications from molecules. In some cases, epigenetic erasers may reverse covalent modifications on histone proteins. In some cases, epigenetic erasers may reverse covalent modifications by removing at least one acetyl group from a histone protein. In some cases, epigenetic erasers may reverse covalent modifications by removing at least one phosphate group from a histone protein. In some cases, epigenetic erasers may reverse covalent modifications by removing at least one ubiquitin molecule from a histone protein. In some cases, epigenetic erasers may reverse covalent modifications by removing at least one methyl group from a histone protein.

The therapeutic agent may include one or more compounds that target epigenetic writers, including, but not limited to: DNA methyltransferases (e.g., DNMT1, DNMT2, DNMT3, DNMT3L), histone acetyltransferases (e.g., GCNS/PCAF, GNAT related, Myst family, CBP/p300, TAF250 family, Src family), histone methyltransferases (e.g., KMT1A, KMT1B, KMT1C, KMT1D, KMT1E, KMT1F, MLL, DOT1, KMT3A, KMT3B, KMT3C, KMT5A, KMT5B, KMT6/EZH2, EZH1, KMT7/SET7&9, KMT8/RIZ1), serine/threonine kinases (e.g., MST, AMPK, Haspin, VRK, Aurora A, Aurora B, Aurora C, PLK 1, PLK 2, PLK 3, Chk1, Chk2, ATR, ATM, PKCa/b/d, MSK1/2, JNK1, JNK2, JNK3). The therapeutic agent may include one or more compounds that target epigenetic readers, including, but not limited to: MeCP2, MBD1, MBD2, MBD3, bromodomain and extraterminal (BET) proteins (e.g., BRD2, BRD3, BRD4, Bdf, Brg), chromodomain proteins (e.g., HP1-like, polycomb-like, CHD-like), Tudor domain proteins (e.g., SMN), PHD finger proteins (e.g., CBD, ING2, DNMT3L, PHF6), 14-3-3 proteins. The therapeutic agent may include one or more compounds that target epigenetic erasers, including, but not limited to: MBD2, TET, histone deacteylases (HDAC) Classes I-IV (e.g., HDAC1/2/3/8, HDAC4/5/7/9, HDAC6/10, Sirt1, Sirt2, Sirt3, Sirt4, Sirt5, Sirt6, Sirt7, HDAC11), lysine demethylases (e.g., LSD1/KDM1, JHMD/Jumonji (e.g., JHDM1A/B, JHMD2A/B, JHMD3A-D, JARID1A-D, UTX), protein phosphatases (e.g., PPP2CA, PPP2CB, PPP1C, PP1D, EYA1, EYA2, EYA3), poly (ADP-ribose) polymerase (PARP), hypoxia-inducible factor (HIF), Pim kinases, and Aurora kinases.

The methods provided herein may involve administering an inhibitor of a methyltransferase to the subject. Likewise, many of the compositions provided herein may comprise a methyltransferase inhibitor, either singly or co-formulated with another agent. In some cases, the methyltransferase inhibitor is a DNA methyltransferase inhibitor. Non-limiting examples of DNA methyltransferases may include DNA (cytosine-5)-methyltransferase 1 (DNMT1); DNA (cytosine-5)-methyltransferase 3A (DNMT3A); or DNA (cytosine-5)-methyltransferase 3B (DNMT3B). In some cases, the methyltransferase inhibitor is a histone methyltransferase inhibitor. Non-limiting examples of histone methyltransferases may include histone-lysine N-methyltransferase ASHL1 (ASHL1); Histone-lysine N-methyltransferase, H3 lysine-79 specific (DOT1L); Euchromatic histone-lysine N-methyltransferase 1 (ENMT1); Euchromatic histone-lysine N-methyltransferase 2 (ENMT2); Histone-lysine N-methyltransferase EZH1 (EZH1); Histone-lysine N-methyltransferase EZH2 (EZH2); Histone-lysine N-methyltransferase 2A (KMT2A); Histone-lysine N-methyltransferase 2D (KMT2D); Histone-lysine N-methyltransferase 2C (KMT2C); Histone-lysine N-methyltransferase 2B (KMT2B); Histone-lysine N-methyltransferase 2E (KMT2E); Histone-lysine N-methyltransferase, H3 lysine-36 and H4 lysine-20 specific (NSD1); PR domain zinc finger protein 2 (PRDM2); Protein SET (SET); SET-binding protein (SETBP1); SET domain-containing protein 1A (SETD1A); SET domain-containing protein 1B (SETD1B); SET domain-containing protein 2 (SETD2); SET domain-containing protein 3 (SETD3); SET domain-containing protein 4 (SETD4); SET domain-containing protein 5 (SETD5); SET domain-containing protein 6 (SETD6); SET domain-containing protein 7 (SETD7); SET domain-containing protein 8 (SETD8); SET domain-containing protein 9 (SETD9); SET domain bifurcated 1 (SETDB1); SET domain bifurcated 2 (SETDB2); Histone-lysine N-methyltransferase SETMAR (SETMAR); Histone-lysine N-methyltransferase SMYD1 (SMYD1); N-lysine methyltransferase SMYD2 (SMYD2); Histone-lysine N-methyltransferase SMYD3 (SMYD3); SET and MYND domain-containing protein 4 (SMYD4); SET and MYND domain-containing protein 5 (SMYD5); Histone-lysine N-methyltransferase SUV39H1 (SUV39H1); Histone-lysine N-methyltransferase SUV39H2 (SUV39H2); Histone-lysine N-methyltransferase KMT5B (KMT5B); and Histone-lysine N-methyltransferase KMT5C (KMT5C). In some cases, the methyltransferase inhibitor is an arginine methyltransferase inhibitor. Non-limiting examples of arginine methyltransferases include: Protein arginine N-methyltransferase 1 (PRMT1), Protein arginine N-methyltransferase 2 (PRMT2); Protein arginine N-methyltransferase 3 (PRMT3); Protein arginine N-methyltransferase 4 (PRMT4); and Protein arginine N-methyltransferase 5 (PRMT5). In some cases, the methyltransferase inhibitor is a broad spectrum methyltransferase inhibitor. In other cases, the methyltransferase inhibitor may selectively target one or more specific methyltransferases. In some cases, treatment with a methyltransferase inhibitor reduces or inhibits expression of DUX4 in one or more cells of the subject.

The epigenetic modulators provided herein (e.g., methyltransferase inhibitors), or identified by methods provided herein, may be very useful for treating, or reducing the risk of developing, a muscle disorder (e.g., muscular or neuromuscular dystrophy, FSHD). In some cases, administration of methyltransferase inhibitors (singly or in combination with other agents) may cure, reverse, or stabilize the muscle disorder (e.g., FSHD). In some cases, such administration may reduce the symptoms of the muscle disorder. Exemplary symptoms of FSHD that may be reduced by the compositions provided herein include muscle atrophy, particularly muscle atrophy of muscles associated with the eye, mouth, upper arm, lower leg, abdomen, and/or hip. The reduction may be a significant reduction of symptoms, such as a greater than 1-fold, 2-fold, 3-fold, 4-fold or higher reduction in symptoms. In some cases, the methyl transferase inhibitors provided herein cause little to no side effects, or reduced side effects particularly when compared with broad-spectrum methyltransferases.

Agents that Reduce DUX4 Expression

This disclosure provides compounds or agents that reduce DUX4 expression in muscle lineage cells (e.g., skeletal muscle cells, myotubes, myoblasts, satellite cells). Compounds or agents that reduce DUX4 expression may include histone methyltransferase inhibitors. Particular examples of such compounds include, but are not limited to: GSK126, EPZ4676, EPZ005687, GSK343, EI-1, CPI-360, CPI-169, UNC1999, GSK503, tazemetostat, BIX01294 (Table 1), a compound of Table 1, and a compound of any one of Formulas (I), (II), or (III).

TABLE 1
Representative compounds that reduce DUX4 expression
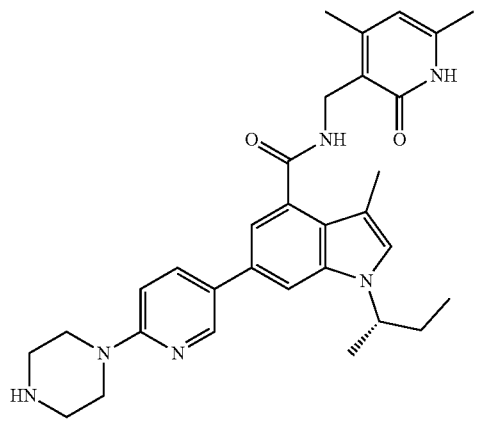
GSK126 (ASK19)
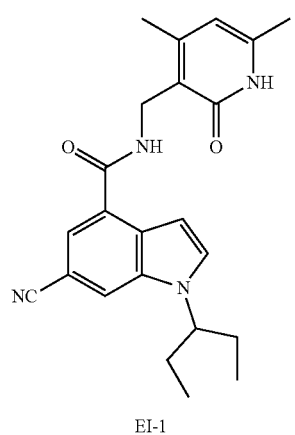 [SMILES: CCC(CC)n1ccc2c(C(=O)NCc3c(C)cc(C)[nH]c3=O)cc(C#N)cc21]
EI-1
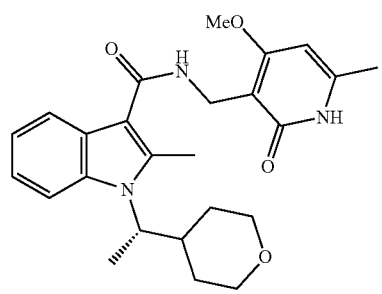
CPI-360
TABLE 1-continued
Representative compounds that reduce DUX4 expression
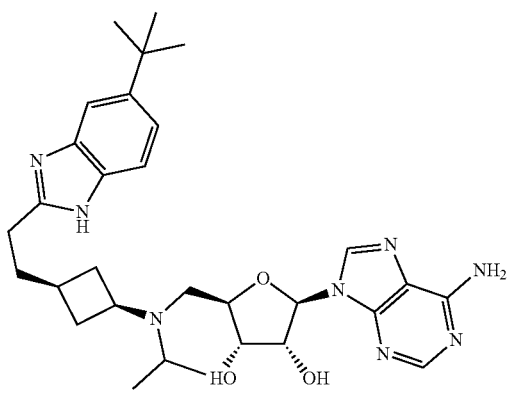
EPZ5676
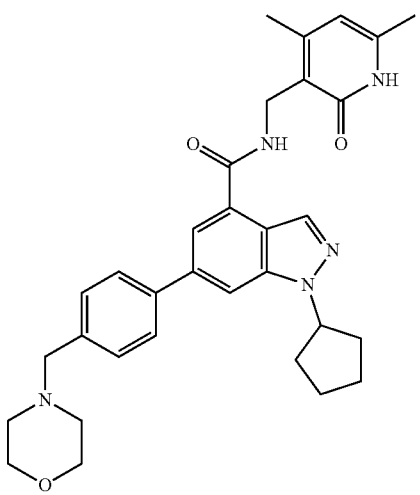
EPZ005687
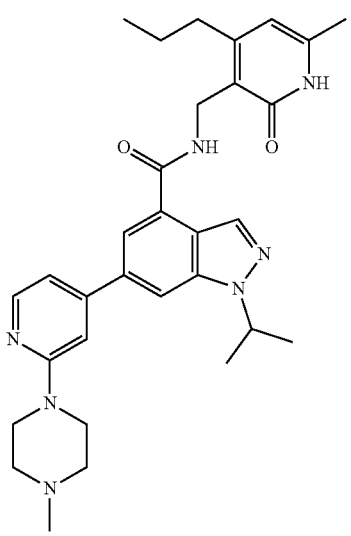
GSK343

TABLE 1-continued

Representative compounds that reduce DUX4 expression

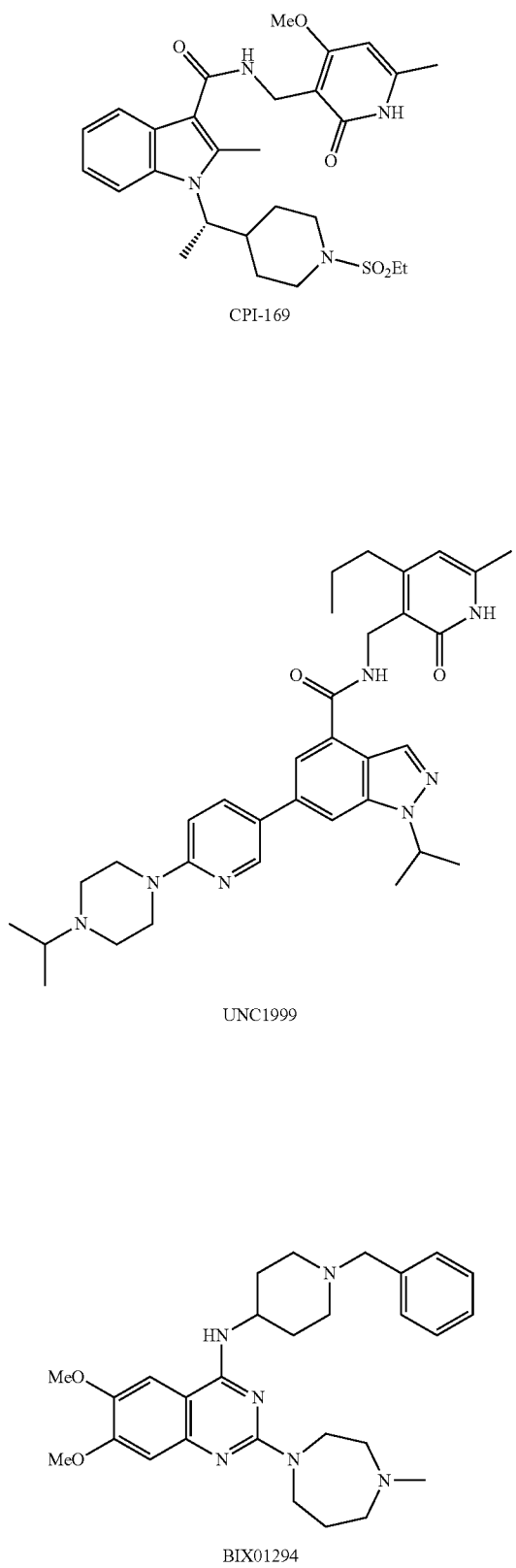

CPI-169

UNC1999

BIX01294

TABLE 1-continued

Representative compounds that reduce DUX4 expression

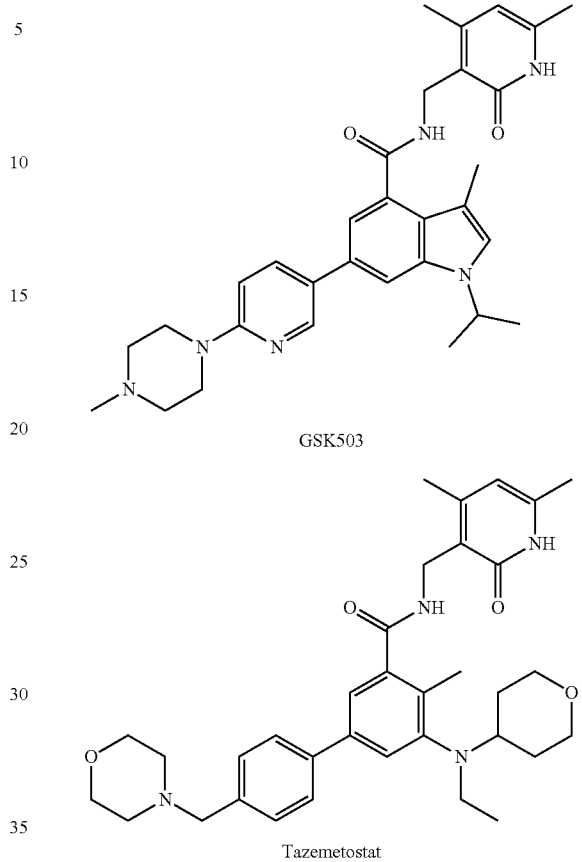

GSK503

Tazemetostat

The reduction in DUX4 expression generated by the compounds or agents provided herein may induce an FSHD-affected skeletal muscle cell to express DUX4 at levels similar to that in normal, healthy muscle cells. In some cases, the level of DUX4 expression may be reduced by at least 20%, at least 30%, at least 40%, at least 50%, at least 60%, at least 70%, at least 80%, at least 90%, at least 95%, at least 98%, or 100%.

According to the methods provided herein, the compounds or agents may have a half maximal effective concentration ($EC_{50}$) of less than 5 μM. In some examples, the compound or compounds may have an $EC_{50}$ of less than about 5 μM, less than about 4 μM, less than about 3 μM, less than about 2 μM, less than about 1 μM, less than about 500 nM, or less than about 100 nM. In a preferred embodiment, the compound or compounds have an $EC_{50}$ of less than about 5 μM.

The compounds or agents provided herein may not be toxic to FSHD-affected skeletal muscle cells. In some cases, the compounds or agents provided herein may not have significant toxicity with respect to FSHD-affected skeletal muscle cells. There may not be any increase, or any significant increase, in cell death in FSHD-affected skeletal muscle cells contacted with a compound or agent provided herein compared to FSHD-affected skeletal muscle cells not contacted by a compound or agent provided herein.

In some cases, a compound according to Formula (I) may be administered to a subject in order to reduce or eliminate the symptoms of FSHD. In some cases, a compound according to Formula (I) may be administered to a subject to treat FSHD or ataxia.

A compound of Formula (I) can have the following structure:

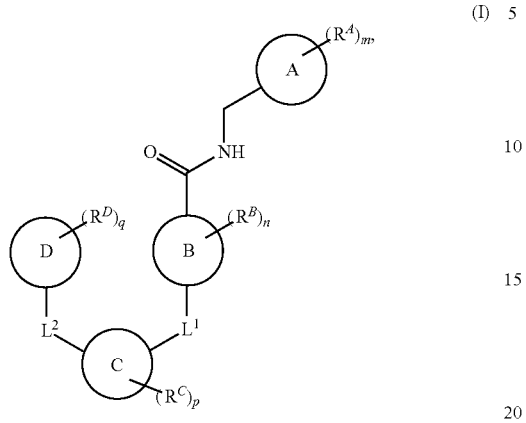

(I)

or a pharmaceutically acceptable salt thereof, wherein:

A is selected from $C_{5-12}$ carbocycle and 5- to 12-membered heterocycle;

B is selected from $C_{5-12}$ carbocycle and 5- to 12-membered heterocycle;

C is selected from bond, $C_{5-12}$ carbocycle, and 5- to 12-membered heterocycle;

D is selected from bond, $C_{5-12}$ carbocycle, and 5- to 12-membered heterocycle;

each of $L^1$ and $L^2$ is independently selected from bond, —O—, —S—, —N($R^{51}$)—, —N($R^{51}$)$CH_2$—, —C(O)—, —C(O)O—, —OC(O)—, —OC(O)O—, —C(O)N($R^{51}$)—, —C(O)N($R^{51}$)C(O)—, —C(O)N($R^{51}$)C(O)N($R^{51}$)—, —N($R^{51}$)C(O)—, —N($R^{51}$)C(O)N($R^{51}$)—, —N($R^{51}$)C(O)O—, —OC(O)N($R^{51}$)—, —C(N$R^{51}$)—, —N($R^{51}$)C(N$R^{51}$)—, —C(N$R^{51}$)N($R^{51}$)—, —N($R^{51}$)C(N$R^{51}$)N($R^{51}$)—, —S(O)$_2$—, —OS(O)—, —S(O)O—, —S(O)—, —OS(O)$_2$—, —S(O)$_2$O—, —N($R^{51}$)S(O)$_2$—, —S(O)$_2$N($R^{51}$)—, —N($R^{51}$)S(O)—, —S(O)N($R^{51}$)—, —N($R^{51}$)S(O)$_2$N($R^{51}$)—, and —N($R^{51}$)S(O)N($R^{51}$)— or from alkylene, alkenylene, alkynylene, heteroalkylene, heteroalkenylene, and heteroalkynylene, each of which is optionally substituted with one or more $R^{50}$;

$R^{50}$ is, at each occurrence, independently selected from: halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$);

$C_{1-10}$ alkyl, $C_{2-10}$ alkenyl, and $C_{2-10}$ alkynyl, each of which is independently optionally substituted at each occurrence with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{52}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$—, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$), $C_{3-12}$ carbocycle, and 3- to 12-membered heterocycle; and $C_{3-12}$ carbocycle and 3- to 12-membered heterocycle, wherein each $C_{3-12}$ carbocycle and 3- to 12-membered heterocycle in $R^{50}$ is independently optionally substituted with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{52}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)N$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$), $C_{1-6}$ alkyl, $C_{1-6}$ haloalkyl, $C_{2-6}$ alkenyl, and $C_{2-6}$ alkynyl;

$R^{51}$ is independently selected at each occurrence from: hydrogen, —C(O)R$^{52}$, —C(O)OR$^{52}$, —C(O)N(R$^{52}$)$_2$, —C(O)NR$^{53}$R$^{54}$;

$C_{1-6}$ alkyl, $C_{2-6}$ alkenyl, and $C_{2-6}$ alkynyl, each of which is independently optionally substituted at each occurrence with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$), $C_{3-12}$ carbocycle and 3- to 12-membered heterocycle; and $C_{3-12}$ carbocycle and 3- to 12-membered heterocycle, wherein each $C_{3-12}$ carbocycle and 3- to 12-membered heterocycle in $R^{51}$ is independently optionally substituted with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(R$^{52}$)(OR$^{52}$), —P(O)(NR$^{52}$)$_2$, =O, =S, =N(R$^{52}$), $C_{1-6}$ alkyl, $C_{1-6}$ haloalkyl, $C_{2-6}$ alkenyl, and $C_{2-6}$ alkynyl;

$R^{52}$ is independently selected at each occurrence from hydrogen; and $C_{1-20}$ alkyl, $C_{2-20}$ alkenyl, $C_{2-20}$ alkynyl, 1- to 6-membered heteroalkyl, $C_{3-12}$ carbocycle, and 3- to 12-membered heterocycle, each of which is optionally substituted by halogen, —CN, —NO$_2$, —NH$_2$, —NHCH$_3$, —NHCH$_2$CH$_3$, =O, —OH, —OCH$_3$, —OCH$_2$CH$_3$, $C_{3-12}$ carbocycle, or 3- to 6-membered heterocycle;

$R^{53}$ and $R^{54}$ are taken together with the nitrogen atom to which they are attached to form a heterocycle, optionally substituted with one or more $R^{50}$;

each of $R^A$, $R^B$, and $R^C$ is independently selected from $R^{50}$;

$R^D$ is, at each occurrence, independently selected from hydrogen or $R^{50}$; and each of m, n, p, and q is independently an integer from 0-12.

In some cases, for a compound of Formula (I), A is 6-membered heterocycle. In some cases, for a compound of Formula (I), A is pyridonyl. In some cases, for a compound of Formula (I), B is selected from 6- to 10-membered aryl and 6- to 10-membered heteroaryl. In some cases, for a compound of Formula (I), B is selected from indolyene, indazolylene, and phenylene. In some cases, for a compound of Formula (I), C is selected from bond, 6-membered aryl, and 6-membered heterocycle. In some cases, for a compound of Formula (I), C is selected from pyridinylene, phenylene, tetrahydropyranylene, and piperidinylene. In some cases, for a compound of Formula (I), D is selected from bond and 6-membered heterocycle. In some cases, for a compound of Formula (I), D is selected from piperazinyl and morpholinyl.

In some cases, for a compound of Formula (I), the compound is of Formula (II):

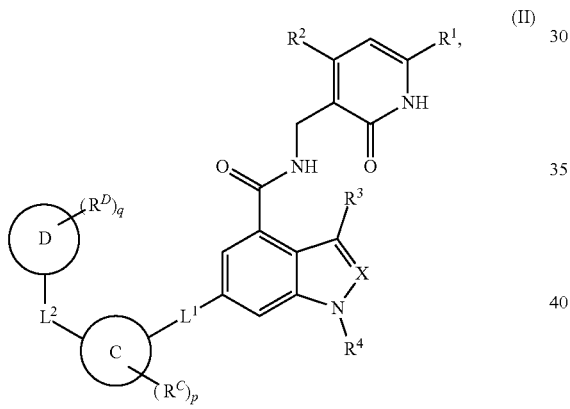

or a pharmaceutically acceptable salt thereof, wherein:
X is C—$R^5$ or N;
each of $R^1$ and $R^2$ is independently $R^{50}$;
$R^3$ is selected from hydrogen and $R^{50}$;
$R^4$ is $R^{52}$; and
$R^5$ is selected from hydrogen and $R^{50}$.

In some cases, for a compound of Formula (II), $R^3$ is H or —$CH_3$. In some cases, for a compound of Formula (II), $R^4$ is $C_{1-5}$ alkyl or $C_{1-5}$ carbocycle. In some cases, for a compound of Formula (I) or Formula (II), $L^1$ is a bond. In some cases, for a compound of Formula (I) or Formula (II), $L^2$ is a bond. In some cases, for a compound of Formula (I) or Formula (II), $L^2$ is $C_{1-3}$ alkylene. In some cases, for a compound of Formula (I) or Formula (II), C is a 6-membered aryl or 6-membered heteroaryl. In some cases, for a compound of Formula (I) or Formula (II), C is a pyridinylene or phenylene. In some cases, for a compound of Formula (I) or Formula (II), D is a 6-membered heterocycle. In some cases, for a compound of Formula (I) or Formula (II), D is piperazinyl or morpholinyl.

In some cases, for a compound of Formula (I), the compound is of Formula (III):

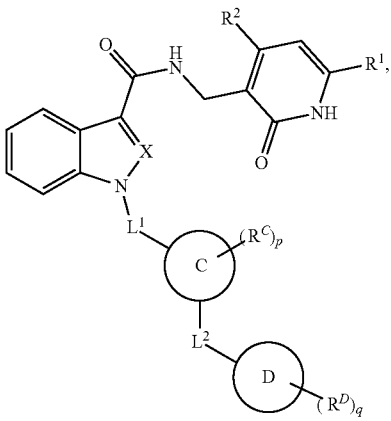

or a pharmaceutically acceptable salt thereof, wherein:
X is C—$R^5$ or N;
each of $R^1$ and $R^2$ is independently $R^{50}$; and
$R^5$ is selected from hydrogen and $R^{50}$.

In some cases, for a compound of Formula (I), Formula (II), or Formula (III), $L_1$ is

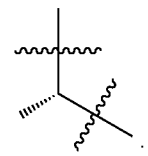

In some cases, for a compound of Formula (I), Formula (II), or Formula (III), C is piperidinylene or morpholinylene. In some cases, for a compound of Formula (I), Formula (II), or Formula (III), p is 0. In some cases, for a compound of Formula (I), Formula (II), or Formula (III), D is a bond.

In some cases, for a compound of Formula (II) or Formula (III), X is C—H. In some cases, for a compound of Formula (II) or Formula (III), X is N. In some cases, for a compound of Formula (II) or Formula (III), $R^1$ is —$CH_3$. In some cases, for a compound of Formula (II) or Formula (III), $R^2$ is $C_{1-3}$ alkyl or —$OR^{52}$. In some cases, for a compound of Formula (II) or Formula (III), $R^2$ is —$CH_3$, —$CH_2CH_2CH_3$, or —$OCH_3$. In some cases, for a compound of Formula (II) or Formula (III), $R^2$ is —$CH_3$.

In some cases, for a compound of Formula (I), Formula (II), or Formula (III), B is a 6-membered aryl. In some cases, for a compound of Formula (I), Formula (II), or Formula (III), B is phenylene. In some cases, for a compound of Formula (I), Formula (II), or Formula (III), C is a 6-membered aryl. In some cases, for a compound of Formula (I), Formula (II), or Formula (III), C is phenylene. In some cases, for a compound of Formula (I), Formula (II), or Formula (III), D is 6-membered heterocycle. In some cases, for a compound of Formula (I), Formula (II), or Formula (III), D is morpholinyl.

In some cases, for a compound of Formula (I), the compound is selected from the group consisting of EPZ005687
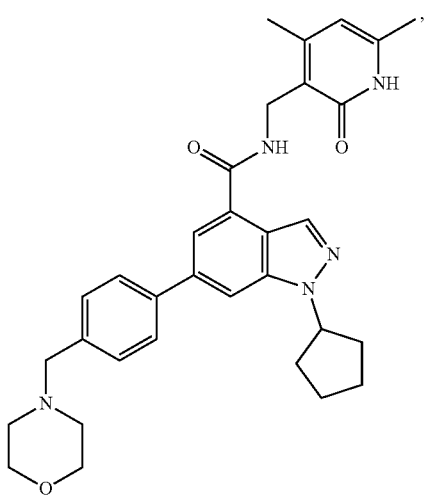
CPI-360
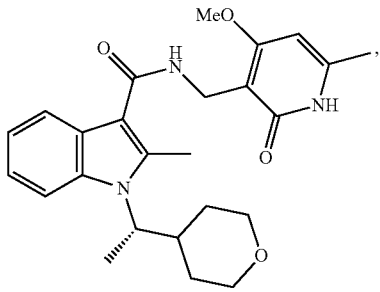
CPI-169
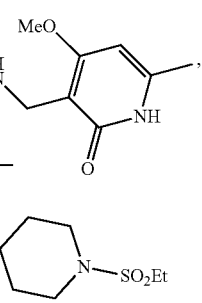
GSK343
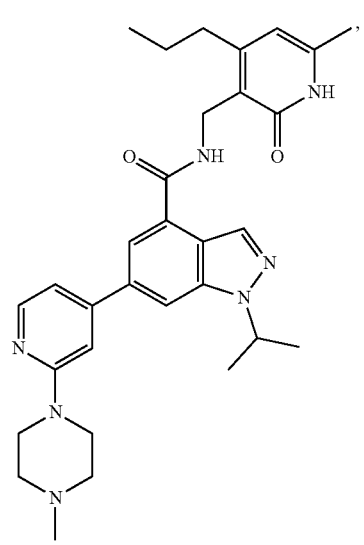
UNC1999
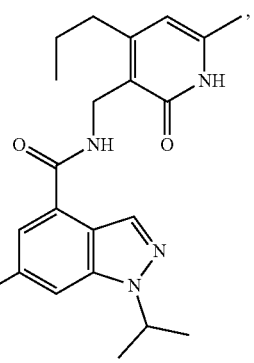
EI-1
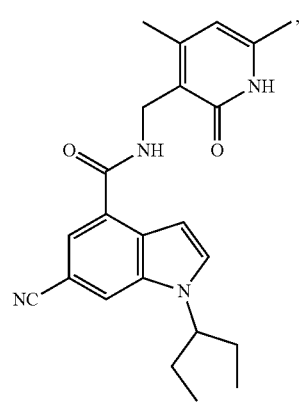
GSK126 (ASK19)
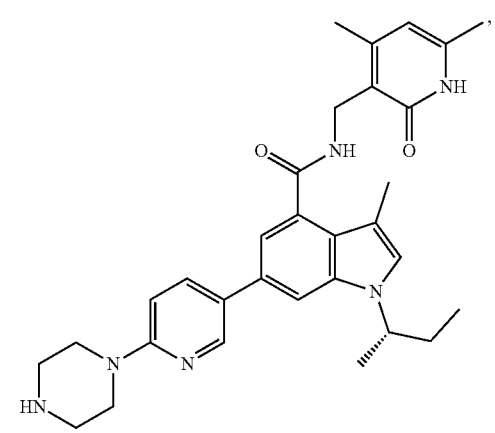

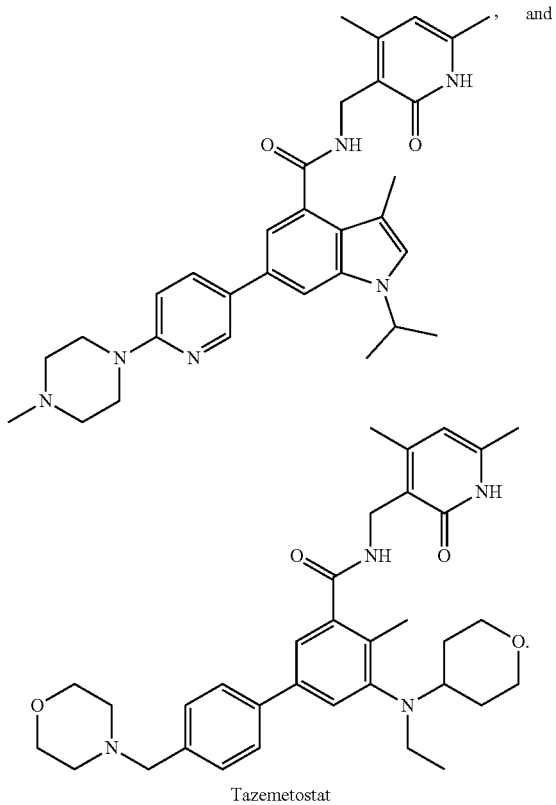

GSK503, and

Tazemetostat

The term "$C_{x-y}$" or "$C_x$-$C_y$" when used in conjunction with a chemical moiety, such as alkyl, alkenyl, or alkynyl is meant to include groups that contain from x to y carbons in the chain. For example, the term "$C_{x-y}$ alkyl" refers to substituted or unsubstituted saturated hydrocarbon groups, including straight-chain alkyl and branched-chain alkyl groups that contain from x to y carbons in the chain. The terms "$C_{x-y}$ alkenyl" and "$C_{x-y}$ alkynyl" refer to substituted or unsubstituted straight-chain or branched-chain unsaturated hydrocarbon groups that contain at least one double or triple bond respectively. Unless stated otherwise specifically in the specification, a $C_{x-y}$ alkyl, $C_{x-y}$ alkenyl, or $C_{x-y}$ alkynyl is optionally substituted by one or more substituents such as those substituents described herein.

"Carbocycle" refers to a saturated, unsaturated or aromatic ring in which each atom of the ring is a carbon atom. Carbocycle may include 3- to 10-membered monocyclic rings, 6- to 12-membered bicyclic rings, and 6- to 12-membered bridged rings. Each ring of a bicyclic carbocycle may be selected from saturated, unsaturated, and aromatic rings. In some embodiments, the carbocycle is an aryl. In some embodiments, the carbocycle is a cycloalkyl. In some embodiments, the carbocycle is a cycloalkenyl. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, are included in the definition of carbocyclic. Exemplary carbocycles include cyclopentyl, cyclohexyl, cyclohexenyl, adamantyl, phenyl, indanyl, and naphthyl. Unless stated otherwise specifically in the specification, a carbocycle is optionally substituted by one or more substituents such as those substituents described herein.

"Aryl" refers to a hydrocarbon ring system moiety comprising 6 to 18 carbon atoms and at least one aromatic ring. For purposes of this disclosure, the aryl moiety is a monocyclic, bicyclic, tricyclic, or tetracyclic ring system, which may include fused or bridged ring systems. Aryl moieties include, but are not limited to, aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" is meant to include aryl groups that are optionally substituted.

"Heterocycle" refers to a saturated, unsaturated or aromatic ring comprising one or more heteroatoms. Exemplary heteroatoms include N, O, Si, P, B, and S atoms. Heterocycles include 3- to 10-membered monocyclic rings, 6- to 12-membered bicyclic rings, and 6- to 12-membered bridged rings. Each ring of a bicyclic heterocycle may be selected from saturated, unsaturated, and aromatic rings. The heterocycle may be attached to the rest of the molecule through any atom of the heterocycle, valence permitting, such as a carbon or nitrogen atom of the heterocycle. In some embodiments, the heterocycle is a heteroaryl. In some embodiments, the heterocycle is a heterocycloalkyl. In an exemplary embodiment, a heterocycle, e.g., pyridyl, may be fused to a saturated or unsaturated ring, e.g., cyclohexane, cyclopentane, or cyclohexene.

"Heteroaryl" refers to a 3- to 12-membered aromatic ring that comprises at least one heteroatom wherein each heteroatom may be independently selected from N, O, and S. As used herein, the heteroaryl ring may be selected from monocyclic or bicyclic and fused or bridged ring systems rings wherein at least one of the rings in the ring system is aromatic, i.e., it contains a cyclic, delocalized (4n+2)π-electron system in accordance with the Hitckel theory. The heteroatom(s) in the heteroaryl may be optionally oxidized. One or more nitrogen atoms, if present, are optionally quaternized. The heteroaryl may be attached to the rest of the molecule through any atom of the heteroaryl, valence permitting, such as a carbon or nitrogen atom of the heteroaryl. Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]

pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term "heteroaryl" is meant to include heteroaryls as defined above which are optionally substituted by one or more substituents such as those substituents described herein.

Compounds of the present disclosure also include crystalline and amorphous forms of those compounds, pharmaceutically acceptable salts, and active metabolites of these compounds having the same type of activity, including, for example, polymorphs, pseudopolymorphs, solvates, hydrates, unsolvated polymorphs (including anhydrates), conformational polymorphs, and amorphous forms of the compounds, as well as mixtures thereof.

The compounds described herein may exhibit their natural isotopic abundance, or one or more of the atoms may be artificially enriched in a particular isotope having the same atomic number, but an atomic mass or mass number different from the atomic mass or mass number predominantly found in nature. All isotopic variations of the compounds of the present disclosure, whether radioactive or not, are encompassed within the scope of the present disclosure. For example, hydrogen has three naturally occurring isotopes, denoted $^1$H (protium), $^2$H (deuterium), and $^3$H (tritium). Protium is the most abundant isotope of hydrogen in nature. Enriching for deuterium may afford certain therapeutic advantages, such as increased in vivo half-life and/or exposure, or may provide a compound useful for investigating in vivo routes of drug elimination and metabolism. Isotopically-enriched compounds may be prepared by conventional techniques well known to those skilled in the art.

Chemical entities having carbon-carbon double bonds or carbon-nitrogen double bonds may exist in Z- or E-form (or cis- or trans-form). Furthermore, some chemical entities may exist in various tautomeric forms. Unless otherwise specified, chemical entities described herein are intended to include all Z-, E- and tautomeric forms as well.

The term "substituted" refers to moieties having substituents replacing a hydrogen on one or more carbons or heteroatoms of the structure. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, a carbocycle, a heterocycle, a cycloalkyl, a heterocycloalkyl, an aromatic and heteroaromatic moiety. In some embodiments, substituents may include any substituents described herein, for example: halogen, hydroxy, oxo (=O), thioxo (=S), cyano (—CN), nitro (—NO$_2$), imino (=N—H), oximo (=N—OH), hydrazino (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2), and —R$^b$—S(O)$_t$N(R$^a$)$_2$ (where t is 1 or 2); and alkyl, alkenyl, alkynyl, aryl, aralkyl, aralkenyl, aralkynyl, cycloalkyl, cycloalkylalkyl, heterocycloalkyl, heterocycloalkylalkyl, heteroaryl, and heteroarylalkyl any of which may be optionally substituted by alkyl, alkenyl, alkynyl, halogen, hydroxy, haloalkyl, haloalkenyl, haloalkynyl, oxo (=O), thioxo (=S), cyano (—CN), nitro (—NO$_2$), imino (=N—H), oximo (=N—OH), hydrazine (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2); wherein each R$^a$ is independently selected from hydrogen, alkyl, cycloalkyl, cycloalkylalkyl, aryl, aralkyl, heterocycloalkyl, heterocycloalkylalkyl, heteroaryl, or heteroarylalkyl, wherein each R$^a$, valence permitting, may be optionally substituted with alkyl, alkenyl, alkynyl, halogen, haloalkyl, haloalkenyl, haloalkynyl, oxo (=O), thioxo (=S), cyano (—CN), nitro (—NO$_2$), imino (=N—H), oximo (=N—OH), hydrazine (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2); and wherein each R$^b$ is independently selected from a direct bond or a straight or branched alkylene, alkenylene, or alkynylene chain, and each R$^c$ is a straight or branched alkylene, alkenylene or alkynylene chain.

It will be understood by those skilled in the art that substituents can themselves be substituted, if appropriate. Unless specifically stated as "unsubstituted," references to chemical moieties herein are understood to include substituted variants. For example, reference to a "heteroaryl" group or moiety implicitly includes both substituted and unsubstituted variants.

Where substituent groups are specified by their conventional chemical formulae, written from left to right, they equally encompass the chemically identical substituents that would result from writing the structure from right to left, e.g., —CH$_2$O— is equivalent to —OCH$_2$—.

"Prodrug" is meant to indicate a compound that may be converted under physiological conditions or by solvolysis to a biologically active compound described herein (e.g., a compound of Table 1 or compound of Formula (I), (II), or (III)). Thus, the term "prodrug" refers to a precursor of a biologically active compound that is pharmaceutically acceptable. In some aspects, a prodrug is inactive when administered to a subject but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam); Higuchi, T., et al., "Pro-drugs as Novel Delivery Systems," (1987) A.C.S. Symposium Series, Vol. 14; and Bioreversible Carriers in Drug Design, ed. Edward B. Roche, American Pharmaceutical Association and Pergamon Press) each of which is incorporated in full by reference herein. The term "prodrug" is also meant to include any covalently bonded carriers, which release the active compound in vivo when such prodrug is administered to a mammalian subject. Prodrugs of an active compound, as described herein, are typically prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of a hydroxy functional group, or acetamide, formamide and benzamide derivatives of an amine functional group in the active compound and the like.

"Optional" or "optionally" means that the subsequently described event of circumstances may or may not occur, and that the description includes instances where the event or circumstance occurs and instances in which it does not. For example, "optionally substituted aryl" means that the aryl group may or may not be substituted and that the description includes both substituted aryl groups and aryl groups having no substitution.

The compounds of the current disclosure, or their pharmaceutically acceptable salts may contain one or more asymmetric centers and may thus give rise to enantiomers, diastereomers, and other stereoisomeric forms that are defined, in terms of absolute stereochemistry, as (R)- or (S)- or, as (D)- or (L)-for amino acids. The present invention is meant to include all such possible isomers, as well as their racemic and optically pure forms. A "stereoisomer" refers to a compound made up of the same atoms bonded by the same bonds but having different three-dimensional structures, which are not interchangeable. The present disclosure contemplates various stereoisomers and mixtures thereof and includes "enantiomers," which refers to two stereoisomers whose molecules are nonsuperimposeable mirror images of one another. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers.

When desired, the (R)- and (S)-isomers of the compounds of the present disclosure, if present, may be resolved by methods known to those skilled in the art, for example by formation of diastereoisomeric salts or complexes which may be separated, for example, by crystallization; via formation of diastereoisomeric derivatives which may be separated, for example, by crystallization, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. Alternatively, a specific enantiomer may be synthesized by asymmetric synthesis using optically active reagents, substrates, catalysts or solvents, or by converting one enantiomer to the other by asymmetric transformation.

Compounds may be dosed in their enantiomerically pure form. In some examples, the compound has an enantiomeric excess greater than about 50%, 60%, 70%, 80%, 90%, 95%, 96%, 97%, 98%, or 99%. Compounds may be dosed in their diasteriomerically pure form. In some examples, the compound has a diasteriomeric excess greater than about 50%, 60%, 70%, 80%, 90%, 95%, 96%, 97%, 98%, or 99%.

Stereocenters may be defined using the Cahn-Ingold-Prelog priority rules. Compounds may have stereocenters in the R-configuration. Compounds may have stereocenters in the S-configuration.

Therapeutic Agent Formulations

In some cases, a pharmaceutical composition (e.g., for oral administration or for injection, infusion, buccal delivery, subcutaneous delivery, intramuscular delivery, intraperitoneal delivery, sublingual delivery, or other method) may be in the form of a liquid. A liquid pharmaceutical composition may include, for example, one or more of the following: a sterile diluent such as water, saline solution, preferably physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers and agents for the adjustment of tonicity such as sodium chloride or dextrose. A parenteral composition may be enclosed in ampoules, disposable syringes or multiple dose vials made of glass or plastic. The use of physiological saline is preferred, and an injectable pharmaceutical composition is preferably sterile. In another embodiment, for treatment of an ophthalmological condition or disease, a liquid pharmaceutical composition may be applied to the eye in the form of eye drops. A liquid pharmaceutical composition may be delivered orally.

For oral formulations, at least one of the compounds or agents described herein may be used alone or in combination with appropriate additives to make tablets, powders, granules or capsules, and if desired, with diluents, buffering agents, moistening agents, preservatives, coloring agents, and flavoring agents. The compounds or agents may be formulated with a buffering agent to provide for protection of the compound from low pH of the gastric environment and/or an enteric coating. A compound included in a pharmaceutical composition may be formulated for oral delivery with a flavoring agent, (e.g., in a liquid, solid or semi-solid formulation and/or with an enteric coating). In some cases, the compounds of this disclosure may be solubilized and encapsulated (e.g., in a liposome or a biodegradable polymer), or used in the form of microcrystals coated with an appropriate nontoxic lipid.

A pharmaceutical composition comprising any one of the compounds or agents described herein may be formulated for sustained or slow release (also called timed release or controlled release). Such compositions may generally be prepared using well known technology and administered by, for example, oral, rectal, intradermal, or subcutaneous implantation, or by implantation at the desired target site. Sustained-release formulations may contain the compound dispersed in a carrier matrix and/or contained within a reservoir surrounded by a rate controlling membrane. Excipients for use within such formulations are biocompatible, and may also be biodegradable; preferably the formulation provides a relatively constant level of active component release. Non-limiting examples of excipients include water, alcohol, glycerol, chitosan, alginate, chondroitin, Vitamin E, mineral oil, and dimethyl sulfoxide (DMSO). The amount of compound contained within a sustained release formulation depends upon the site of implantation, the rate and expected duration of release, and the nature of the condition, disease or disorder to be treated or prevented.

Some compounds may exhibit polymorphism. It is to be understood that the present disclosure encompasses any racemic, optically-active, polymorphic, or stereoisomeric form, or mixtures thereof, of a compound of the disclosure, which possesses the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase).

The present disclosure further provides salts of any compound described herein. The term "salt" or "pharmaceutically acceptable salt" refers to salts derived from a variety of organic and inorganic counter ions well known in the art. Salts include, for example, acid-addition salts and base-addition salts. The acid that is added to a compound to form an acid-addition salt can be an organic acid or an inorganic acid. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p toluenesulfonic acid, salicylic acid, and the like. A base that is added to a compound to form a base-addition salt can be an organic base or an inorganic base. In some cases, a salt can be a metal salt. In some cases, a salt can be an ammonium salt. Inorganic bases from which salts can be derived include, for example, sodium, potassium, lithium, ammonium, calcium, magnesium, iron, zinc, copper, manganese, aluminum, and the like. Organic bases from which salts can be derived include, for example, primary, secondary, and tertiary amines, substituted amines including naturally occurring substituted amines, cyclic amines, basic ion exchange resins, and the like.

Acid addition salts can arise from the addition of an acid to a compound described herein. In some cases, the acid can be organic. In some cases, the acid can be inorganic. Non-limiting examples of suitable acids include hydrochloric acid, hydrobromic acid, hydroiodic acid, nitric acid, nitrous acid, sulfuric acid, sulfurous acid, a phosphoric acid, nicotinic acid, isonicotinic acid, lactic acid, salicylic acid, 4-aminosalicylic acid, tartaric acid, ascorbic acid, gentisinic acid, gluconic acid, glucaronic acid, saccaric acid, formic acid, benzoic acid, glutamic acid, pantothenic acid, acetic acid, propionic acid, butyric acid, fumaric acid, succinic acid, citric acid, oxalic acid, maleic acid, hydroxymaleic acid, methylmaleic acid, glycolic acid, malic acid, cinnamic acid, mandelic acid, 2-phenoxybenzoic acid, 2-acetoxybenzoic acid, embonic acid, phenylacetic acid, N-cyclohexylsulfamic acid, methanesulfonic acid, ethanesulfonic acid, benzenesulfonic acid, p-toluenesulfonic acid, 2-hydroxyethanesulfonic acid, ethane-1,2-disulfonic acid, 4-methylbenzenesulfonic acid, naphthalene-2-sulfonic acid, naphthalene-1,5-disulfonic acid, 2-phosphoglyceric acid, 3-phosphoglyceric acid, glucose-6-phosphoric acid, and an amino acid.

Non-limiting examples of suitable acid addition salts include a hydrochloride salt, a hydrobromide salt, a hydroiodide salt, a nitrate salt, a nitrite salt, a sulfate salt, a sulfite salt, a phosphate salt, a hydrogen phosphate salt, a dihydrogen phosphate salt, a carbonate salt, a bicarbonate salt, a nicotinate salt, an isonicotinate salt, a lactate salt, a salicylate salt, a 4-aminosalicylate salt, a tartrate salt, an ascorbate salt, a gentisinate salt, a gluconate salt, a glucaronate salt, a saccarate salt, a formate salt, a benzoate salt, a glutamate salt, a pantothenate salt, an acetate salt, a propionate salt, a butyrate salt, a fumarate salt, a succinate salt, a citrate salt, an oxalate salt, a maleate salt, a hydroxymaleate salt, a methylmaleate salt, a glycolate salt, a malate salt, a cinnamate salt, a mandelate salt, a 2-phenoxybenzoate salt, a 2-acetoxybenzoate salt, an embonate salt, a phenylacetate salt, an N-cyclohexylsulfamate salt, a methanesulfonate salt, an ethanesulfonate salt, a benzenesulfonate salt, a p-toluenesulfonate salt, a 2-hydroxyethanesulfonate salt, an ethane-1,2-disulfonate salt, a 4-methylbenzenesulfonate salt, a naphthalene-2-sulfonate salt, a naphthalene-1,5-disulfonate salt, a 2-phosphoglycerate salt, a 3-phosphoglycerate salt, a glucose-6-phosphate salt, and an amino acid salt.

Metal salts can arise from the addition of an inorganic base to a compound described herein. The inorganic base consists of a metal cation paired with a basic counterion, such as, for example, hydroxide, carbonate, bicarbonate, or phosphate. The metal can be an alkali metal, alkaline earth metal, transition metal, or main group metal. Non-limiting examples of suitable metals include lithium, sodium, potassium, caesium, cerium, magnesium, manganese, iron, calcium, strontium, cobalt, titanium, aluminium, copper, cadmium, and zinc.

Non-limiting examples of suitable metal salts include a lithium salt, a sodium salt, a potassium salt, a caesium salt, a cerium salt, a magnesium salt, a manganese salt, an iron salt, a calcium salt, a strontium salt, a cobalt salt, a titanium salt, an aluminium salt, a copper salt, a cadmium salt, and a zinc salt.

Ammonium salts can arise from the addition of ammonia or an organic amine to a compound described herein. Non-limiting examples of suitable organic amines include triethyl amine, diisopropyl amine, ethanol amine, diethanol amine, triethanol amine, morpholine, N-methylmorpholine, piperidine, N-methylpiperidine, N-ethylpiperidine, dibenzyl amine, piperazine, pyridine, pyrrazole, pipyrrazole, imidazole, pyrazine, pipyrazine, ethylenediamine, N,N'-dibenzylethylene diamine, procaine, chloroprocaine, choline, dicyclohexyl amine, and N-methylglucamine.

Non-limiting examples of suitable ammonium salts can be a triethyl amine salt, a diisopropyl amine salt, an ethanol amine salt, a diethanol amine salt, a triethanol amine salt, a morpholine salt, an N-methylmorpholine salt, a piperidine salt, an N-methylpiperidine salt, an N-ethylpiperidine salt, a dibenzyl amine salt, a piperazine salt, a pyridine salt, a pyrrazole salt, a pipyrrazole salt, an imidazole salt, a pyrazine salt, a pipyrazine salt, an ethylene diamine salt, an N,N'-dibenzylethylene diamine salt, a procaine salt, a chloroprocaine salt, a choline salt, a dicyclohexyl amine salt, and a N-methylglucamine salt.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions of the disclosure is contemplated. Supplementary active ingredients can also be incorporated into the compositions.

The term "pharmaceutically acceptable excipient" is intended to include vehicles and carriers capable of being co-administered with a compound to facilitate the performance of its intended function. The use of such media for pharmaceutically active substances is well known in the art. Examples of such vehicles and carriers include solutions, solvents, dispersion media, delay agents, emulsions and the like. Any other conventional carrier suitable for use with the multi-binding compounds also falls within the scope of the present disclosure.

In making the compositions of this disclosure, the active ingredient can be diluted by an excipient. Some examples of suitable excipients include lactose, dextrose, sucrose, sorbitol, mannitol, starches, gum acacia, calcium phosphate, alginates, tragacanth, gelatin, calcium silicate, microcrystalline cellulose, PEG, polyvinylpyrrolidone, cellulose, water, sterile saline, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the disclosure can be formulated so as to provide quick, sustained or delayed release of the active ingredient after administration to the patient by employing procedures known in the art.

In some cases, the pharmaceutical compositions described herein may comprise an excipient that can provide long term preservation, bulk up a formulation that contains potent active ingredients, facilitate drug absorption, reduce viscosity, add flavoring, or enhance the solubility of the pharmaceutical composition. Non-limiting examples of excipients can include anti-adherents, binders (e.g., sucrose, lactose, starches, cellulose, gelatin, or polyethylene glycol), coatings (e.g., hydroxypropyl methylcellulose or gelatin), disintegrants, dyes, flavors (e.g., mint, peach, raspberry, or vanilla), glidants, lubricants, preservatives (e.g., acids, esters, phenols, mercurial compounds, or ammonium compounds), sorbents, or vehicles (e.g., petroleum or mineral oil).

The pharmaceutical compositions disclosed herein may be any type of formulation including solid formulations. In some cases the solid formulation (or other type of formulation) comprises at least 0.01 mg, 0.1 mg, 1 mg, 2 mg, 3 mg, 4 mg, 5 mg, 6 mg, 7 mg, 8 mg, 9 mg, 10 mg, 20 mg, 30 mg, 40 mg, 50 mg, 60 mg, 70 mg, 80 mg, 90 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, or 1000 mg of GSK126, a compound of Table 1, or a compound of any one of Formulas (I), (II), or (III). As used herein, the terms GSK126 and ASK19 are used interchangeably.

In some cases, the liquid formulation may comprise a concentration of GSK126, a compound of Table 1, or a compound of any one of Formulas (I), (II), or (III) of at least 0.1 mg/ml, 1 mg/ml, 2 mg/ml, 3 mg/ml, 4 mg/ml, 5 mg/ml, 6 mg/ml, 7 mg/ml, 8 mg/ml, 9 mg/ml, 10 mg/ml, 20 mg/ml, 30 mg/ml, 40 mg/ml, 50 mg/ml, 60 mg/ml, 70 mg/ml, 80 mg/ml, 90 mg/ml, 100 mg/ml, 150 mg/ml, 200 mg/ml, 250 mg/ml, 300 mg/ml, 350 mg/ml, 400 mg/ml, 450 mg/ml, 500 mg/ml, 550 mg/ml, 600 mg/ml, 650 mg/ml, 700 mg/ml, 750 mg/ml, 800 mg/ml, 850 mg/ml, 900 mg/ml, 950 mg/ml, or 1000 mg/ml.

In some cases, a pharmaceutical composition or formulation described herein may comprise a combination of different agents. In some cases, a pharmaceutical composition described herein may comprise at least 2 agents, at least 3 agents, at least 4 agents, at least 5 agents, or more agents.

Kits

In some cases, the pharmaceutical compositions disclosed herein may be assembled into kits. In some cases, the kit may comprise one or more compounds provided herein. In some cases, the kit may also comprise instructions for use. The kit may also comprise vials, tubes, needles, packaging, or other material. Generally, a kit provided herein has at least two components; a first component (e.g., tube, vial, blister tray) may contain one or more compounds provided herein, while a second, separate component may contain packaging material, a second compound (either the same or different from the compound in the first component), a tube, vial, blister tray, a buffer, a reagent and/or other material.

Kits with unit doses of one or more of the compounds described herein, usually in oral or injectable doses, are provided. Such kits may include a container containing the unit dose, an informational package insert describing the use and attendant benefits of the drugs in treating the disease, and optionally an appliance or device for delivery of the composition.

The kit may further comprise any device suitable for administration of the composition. For example, a kit comprising an injectable formulation of pharmaceutical compositions may comprise a needle suitable for subcutaneous administration and an alcohol wipe for sterilization of the injection site.

In some cases, kits may be provided with instructions. The instructions may be provided in the kit (e.g., as paper instructions) or they may be accessed electronically (e.g., on the World Wide Web). The instructions may provide information on how to use the compositions of the present disclosure. The instructions may further provide information on how to use the devices of the present disclosure. The instructions may provide information on how to perform the methods of the disclosure. In some cases, the instructions may provide dosing information. The instructions may provide drug information such as the mechanism of action, the formulation of the drug, adverse risks, contraindications, and the like. In some cases, the kit is purchased by a physician or health care provider for administration at a clinic or hospital. In some cases, the kit is purchased by a laboratory and used for screening candidate compounds.

Therapeutic Agent Administration

The compounds of the current disclosure may be administered to a subject with a muscle disease or deficiency in order to treat the muscle disease or deficiency. In some cases the compounds may be methyltransferase inhibitors, including, but not limited to histone methyltransferase inhibitors. In some cases, the compound may be GSK126, a compound of Table 1, or a compound of any one of Formulas (I), (II), or (III).

The compounds of the current disclosure may be administered by any of the accepted modes of administration of agents having similar utilities, for example, by cutaneous, oral, topical, intradermal, intrathecal, intravenous, subcutaneous, intramuscular, intra-articular, intraspinal or spinal, nasal, epidural, rectal, vaginal, or transdermal/transmucosal routes. The most suitable route will depend on the nature and severity of the condition being treated. Subcutaneous, intradermal and percutaneous injections can be routes for the compounds of this disclosure. Sublingual administration may be a route of administration for compounds of this disclosure. Intravenous administration may be a route of administration for compounds of this disclosure. In a particular example, the pharmaceutical composition provided herein may be administered to a patient orally.

In some aspects, the methods provided herein involve administering a compound or agent for a period of time to a subject, followed by withdrawal of the compound or agent. For example, the compound or agent may be administered for 24 hours or less, followed by withdrawal of the compound or agent. In some cases, DUX4 expression remains inhibited after withdrawal of the compound or agent. For example, DUX4 expression may remain inhibited for at least 1 day, at least 2 days, at least 3 days, at least 4 days, at least 5 days, at least 6 days, at least 7 days, at least 8 days, at least 9 days, at least 10 days or greater than 10 days after withdrawal of the compound or agent. In some cases, the compound or agent is administered one or more additional times after withdrawal.

In some cases, the compound or agent is administered as a stand-alone agent. In other cases, the compound or agent is co-administered with one or more additional therapies (e.g., drug). In some cases, the compound or agent is co-administered (or co-formulated) with a cell-based therapy for the treatment of a muscular or neuromuscular dystrophy (e.g., FSHD).

The compounds of the present disclosure, or their pharmaceutically acceptable salts, are generally administered in a therapeutically effective amount. The term "therapeutically effective amount" may generally refer to the amount (or dose) of a compound or other therapy that is minimally sufficient to prevent, reduce, treat or eliminate a condition, or risk thereof, when administered to a subject in need of such compound or other therapy. In some instances the term "therapeutically effective amount" may refer to that amount of compound or other therapy that is sufficient to have a prophylactic effect when administered to a subject. The therapeutically effective amount may vary; for example, it may vary depending upon the subject's condition, the weight and age of the subject, the severity of the disease condition, the manner of administration and the like, all of which may be determined by one of ordinary skill in the art. The amount of the compound actually administered may be determined by a physician or caregiver, in the light of the relevant circumstances, including the condition to be treated, the chosen route of administration, the compound administered and its relative activity, the age, weight, the response of the individual patient, the severity of the patient's symptoms, and the like.

In some cases, administering a compound herein to a patient may comprise administering a daily dose of greater than 0 mg/m$^2$, 1 mg/m$^2$, 2 mg/m$^2$, 3 mg/m$^2$, 4 mg/m$^2$, 5 mg/m$^2$, 6 mg/m$^2$, 7 mg/m$^2$, 8 mg/m$^2$, 9 mg/m$^2$, 10 mg/m$^2$, 11 mg/m$^2$, 12 mg/m$^2$, 13 mg/m$^2$, 14 mg/m$^2$, 15 mg/m$^2$, 16 mg/m$^2$, 17 mg/m$^2$, 18 mg/m$^2$, 19 mg/m$^2$, 20 mg/m$^2$, 21 mg/m$^2$, 22 mg/m$^2$, 23 mg/m$^2$, 24 mg/m$^2$, 25 mg/m$^2$, 26 mg/m$^2$, 27 mg/m$^2$, 28 mg/m$^2$, 29 mg/m$^2$, 30 mg/m$^2$, 31 mg/m$^2$, 32 mg/m$^2$, 33 mg/m$^2$, 34 mg/m$^2$, 35 mg/m$^2$, 36 mg/m$^2$, 37 mg/m$^2$, 38 mg/m$^2$, 39 mg/m$^2$, 40 mg/m$^2$, 41 mg/m$^2$, 42 mg/m$^2$, 43 mg/m$^2$, 44 mg/m$^2$, 45 mg/m$^2$, 46 mg/m$^2$, 47 mg/m$^2$, 48 mg/m$^2$, 49 mg/m$^2$, 50 mg/m$^2$, 100 mg/m$^2$, 150 mg/m$^2$, 200 mg/m$^2$, 300 mg/m$^2$, 350 mg/m$^2$, 400 mg/m$^2$, 450 mg/m$^2$, 500 mg/m$^2$, 750 mg/m$^2$, 1000 mg/m$^2$, 1250 mg/m$^2$, 1500 mg/m$^2$, 1750 mg/m$^2$, or 2000 mg/m$^2$ of a compound to a subject.

In some cases, administering a compound herein to a patient may comprise administering a daily dose of 0.1 mg/m$^2$, 0.2 mg/m$^2$, 0.3 mg/m$^2$, 0.4 mg/m$^2$, 0.5 mg/m$^2$, 0.6 mg/m$^2$, 0.7 mg/m$^2$, 0.8 mg/m$^2$, 0.9 mg/m$^2$, 1 mg/m$^2$, 1.1 mg/m$^2$, 1.2 mg/m$^2$, 1.3 mg/m$^2$, 1.4 mg/m$^2$, 1.5 mg/m$^2$, 1.6 mg/m$^2$, 1.7 mg/m$^2$, 1.8 mg/m$^2$, 1.9 mg/m$^2$, 2 mg/m$^2$, 2.1 mg/m$^2$, 2.2 mg/m$^2$, 2.3 mg/m$^2$, 2.4 mg/m$^2$, 2.5 mg/m$^2$, 2.6 mg/m$^2$, 2.7 mg/m$^2$, 2.8 mg/m$^2$, 2.9 mg/m$^2$, 3 mg/m$^2$, 3.1 mg/m$^2$, 3.2 mg/m$^2$, 3.3 mg/m$^2$, 3.4 mg/m$^2$, 3.5 mg/m$^2$, 3.6 mg/m$^2$, 3.7 mg/m$^2$, 3.8 mg/m$^2$, 3.9 mg/m$^2$, 4 mg/m$^2$, 4.1 mg/m$^2$, 4.2 mg/m$^2$, 4.3 mg/m$^2$, 4.4 mg/m$^2$, 4.5 mg/m$^2$, 4.6 mg/m$^2$, 4.7 mg/m$^2$, 4.8 mg/m$^2$, 4.9 mg/m$^2$, 5 mg/m$^2$, 5.1 mg/m$^2$, 5.2 mg/m$^2$, 5.3 mg/m$^2$, 5.4 mg/m$^2$, 5.5 mg/m$^2$, 5.6 mg/m$^2$, 5.7 mg/m$^2$, 5.8 mg/m$^2$, 5.9 mg/m$^2$, 6 mg/m$^2$, 6.1 mg/m$^2$, 6.2 mg/m$^2$, 6.3 mg/m$^2$, 6.4 mg/m$^2$, 6.5 mg/m$^2$, 6.6 mg/m$^2$, 6.7 mg/m$^2$, 6.8 mg/m$^2$, 6.9 mg/m$^2$, 7 mg/m$^2$, 7.1 mg/m$^2$, 7.2 mg/m$^2$, 7.3 mg/m$^2$, 7.4 mg/m$^2$, 7.5 mg/m$^2$, 7.6 mg/m$^2$, 7.7 mg/m$^2$, 7.8 mg/m$^2$, 7.9 mg/m$^2$, 8 mg/m$^2$, 8.1 mg/m$^2$, 8.2 mg/m$^2$, 8.3 mg/m$^2$, 8.4 mg/m$^2$, 8.5 mg/m$^2$, 8.6 mg/m$^2$, 8.7 mg/m$^2$, 8.8 mg/m$^2$, 8.9 mg/m$^2$, 9 mg/m$^2$, 9.1 mg/m$^2$, 9.2 mg/m$^2$, 9.3 mg/m$^2$, 9.4 mg/m$^2$, 9.5 mg/m$^2$, 9.6 mg/m$^2$, 9.7 mg/m$^2$, 9.8 mg/m$^2$, 9.9 mg/m$^2$, 10 mg/m$^2$, 11 mg/m$^2$, 12 mg/m$^2$, 13 mg/m$^2$, 14 mg/m$^2$, 15 mg/m$^2$, 16 mg/m$^2$, 17 mg/m$^2$, 18 mg/m$^2$, 19 mg/m$^2$, 20 mg/m$^2$, 21 mg/m$^2$, 22 mg/m$^2$, 23 mg/m$^2$, 24 mg/m$^2$, 25 mg/m$^2$, 26 mg/m$^2$, 27 mg/m$^2$, 28 mg/m$^2$, 29 mg/m$^2$, 30 mg/m$^2$, 31 mg/m$^2$, 32 mg/m$^2$, 33 mg/m$^2$, 34 mg/m$^2$, 35 mg/m$^2$, 36 mg/m$^2$, 37 mg/m$^2$, 38 mg/m$^2$, 39 mg/m$^2$, 40 mg/m$^2$, 41 mg/m$^2$, 42 mg/m$^2$, 43 mg/m$^2$, 44 mg/m$^2$, 45 mg/m$^2$, 46 mg/m$^2$, 47 mg/m$^2$, 48 mg/m$^2$, 49 mg/m$^2$, 50 mg/m$^2$, 51 mg/m$^2$, 52 mg/m$^2$, 53 mg/m$^2$, 54 mg/m$^2$, 55 mg/m$^2$, 56 mg/m$^2$, 57 mg/m$^2$, 58 mg/m$^2$, 59 mg/m$^2$, 60 mg/m$^2$, 61 mg/m$^2$, 62 mg/m$^2$, 63 mg/m$^2$, 64 mg/m$^2$, 65 mg/m$^2$, 66 mg/m$^2$, 67 mg/m$^2$, 68 mg/m$^2$, 69 mg/m$^2$, 70 mg/m$^2$, 71 mg/m$^2$, 72 mg/m$^2$, 73 mg/m$^2$, 74 mg/m$^2$, 75 mg/m$^2$, 76 mg/m$^2$, 77 mg/m$^2$, 78 mg/m$^2$, 79 mg/m$^2$, 80 mg/m$^2$, 81 mg/m$^2$, 82 mg/m$^2$, 83 mg/m$^2$, 84 mg/m$^2$, 85 mg/m$^2$, 86 mg/m$^2$, 87 mg/m$^2$, 88 mg/m$^2$, 89 mg/m$^2$, 90 mg/m$^2$, 91 mg/m$^2$, 92 mg/m$^2$, 93 mg/m$^2$, 94 mg/m$^2$, 95 mg/m$^2$, 96 mg/m$^2$, 97 mg/m$^2$, 98 mg/m$^2$, 99 mg/m$^2$, or 100 mg/m$^2$ of the compound.

The daily dose of the compound may be greater than 0 mg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 100 mg, 150 mg, 200 mg, 300 mg, 350 mg, 400 mg, 450 mg, 500 mg, 750 mg, 1g, 5 g, 10 g, or higher.

In some cases, the daily dose of the compound may be administered in a single dose. In some cases, the daily dose may be divided into 1, 2, 3, 4, 5, 6, 7, 8, 9, or 10 doses per day. For example, the daily dose can be divided into 3 doses per day. In some cases, the daily dose of the chemotherapeutic drug may be divided into at least 1, 2, 3, 4, 5, 6, 7, 8, 9, 10, 15, 20, 25, 30, 35, 40, 45, 50, 55, or 60 infusions per hour. In some cases, each infusion of a composition comprising a chemotherapeutic drug may last for at least 5 minutes, 10 minutes, 15 minutes, 20 minutes, 25 minutes, 30 minutes, 35 minutes, 40 minutes, 45 minutes, 50 minutes, 55 minutes, 1 hour, 1.5 hours, 2 hours, 2.5 hours, 3 hours, 3.5 hours, 4 hours, 4.5 hours, 5 hours, 5.5 hours, or 6 hours.

The compounds described herein may be administered to a patient one or more times per day. In some cases, the compounds may be administered to a patient one time per day. In some cases, the compounds may be administered to a patient at least 2 times, 3 times, 4 times 5 times, 6 times, 7 times, 8 times, 9 times, 10 times, 11 times, 12 times, 13 times, 14 times, 15 times, 16 times, 17 times, 18 times, 19 times, 20 times, 21 times, 22 times, 23 times, or 24 times per day. For example, a compound may be administered to a patient 3 times per day.

The compound described herein may be administered to a patient for one or more days. In some cases, the compound may be administered to a patient for one day. In some cases, the pharmaceutical composition may be administered to the patient for at least 2 days, 3 days, 4 days, 5 days, 6 days, 1 week, 2 weeks, 3 weeks, 1 month, 2 months, 3 months, 4 months, 5 months, 6 months, 7 months, 8 months, 9 months, 10 months, 11 months, 1 year, 2 years, 3 years, 4 years, 5 years, 6 years, 7 years, 8 years, 9 years, 10 years, 20 years, 30 years, 40 years, or 50 years.

The compounds described herein may be effective over time. In some cases, the compounds may be effective for one or more days. In some cases, the duration of efficacy of the compounds is over a long period of time. In some cases, the efficacy of the compound may be greater than 2 days, 3 days, 4 days, 5 days, 6 days, 1 week, 2 weeks, 3 weeks, or 1 month.

In certain particular embodiments, more than one compound of the current disclosure may be administered at a time to a subject. In some embodiments, two compounds of the current disclosure in combination make act synergistically or additively, and either compound may be used in a lesser amount than if administered alone.

Any of the compounds or agents provided herein may be administered to a subject in combination with a cell therapy. The effects of the combination may be additive; in some cases, the effects of the combination are synergistic. The compounds may be administered before, during or after the administration of the cell therapy. In some cases, the compounds or agents are administered separately from the cell therapy. In some cases, the cell therapy is mixed with one or more of the compounds. In some examples, the cell therapy may involve introducing skeletal muscle cells into a subject and a compound provided herein is also administered into the subject in order to repress DUX4 expression in vivo in skeletal muscle cells.

IV. Cell Therapies

Healthy skeletal muscle cells or myogenic precursor cells (e.g., myotubes, myoblasts, satellite cells) may be used as a therapy to treat a subject with a disease or disorder (e.g., a genetic defect), particularly a disease or disorder affecting muscle function, (e.g., FSHD). The cell therapy may be directed to treating the cause of the disease and/or to treating the effects of the disease or condition. The cell therapy may include introducing cells into a subject at a site where the subject experiences muscle weakness. For example, the cells may be enclosed in a material, such as a microcapsule, designed to shuttle the cells to a site of interest. In some examples, the introduced cells may advantageously replace the damaged, diseased, or injured cells and allow improvement in the overall condition of the subject.

In some cases, healthy skeletal muscle cells or myogenic precursor cells used as cell therapy may be generated by contacting FSHD-affected skeletal muscle cells or FSHD-affected myogenic precursor cells with a compound or compounds according to the methods herein (e.g., a compound of Formula (I)), thereby reducing expression of DUX4. In some cases, the cells may be genetically modified to remove the FSHD-causing mutation. Healthy skeletal muscle cells may be generated from FSHD-affected skeletal muscle cells and FSHD-affected myogenic precursor cells obtained from a variety of sources, including, but not limited to primary cells from a subject with FSHD, induced pluripotent stem cells, and embryonic stem cells.

Induced pluripotent stem cells may be derived from a variety of cell types obtained from a subject, including but not limited to: fibroblasts, bone-marrow derived mononuclear cells, skeletal muscle cells, adipose cells, peripheral blood mononuclear cells, blood cells, peripheral blood lymphocytes, macrophages, keratinocytes, oral keratinocytes, hair follicle dermal cells, gastric epithelial cells, lung epithelial cells, synovial cells, kidney cells, skin epithelial cells, or osteoblasts.

Induced pluripotent stem cells may be derived from cells obtained from subjects with a variety of disease statuses, including any of the subjects described herein. Induced pluripotent stem cells may be derived from cells obtained from a subject who is free of an adverse health condition. In some cases, induced pluripotent stem cells may be derived from cells obtained from a subject who has or is at risk of having a disease or disorder. In some cases, induced pluripotent stem cells may be derived from cells obtained from a subject who has, or is at risk of having, a muscular degenerative disease or disorder such as a muscular deficiency disease described herein (e.g., FSHD). In some cases, cells may be obtained from a subject who has, or is at risk of having, a genetic disease or disorder; in such cases, the methods provided herein may be used to treat or ameliorate the disease or disorder. The subject may also have other diseases or disorders, including, but not limited to, cardiovascular disease, eye disease (e.g., macular degeneration), auditory disease, (e.g., deafness), diabetes, cognitive impairment, schizophrenia, depression, bipolar disorder, dementia, neurodegenerative disease, Alzheimer's Disease, Parkinson's Disease, multiple sclerosis, osteoporosis, liver disease, kidney disease, autoimmune disease, arthritis, or a proliferative disorder (e.g., a cancer).

Production of induced pluripotent stem cells may be achieved by forcing the expression of polypeptides, particularly proteins that play a role in maintaining or regulating self-renewal and/or pluripotency of embryonic stem cells. Examples of such proteins are Oct3/4, Sox2, Klf4, L-Myc, N-myc and c-Myc transcription factors, all of which are highly expressed in embryonic stem cells. Additionally, in some examples iPSC cells are prepared without using c-Myc, N-myc, or L-myc or a protein that will cause cancer. Forced expression may include introducing expression vectors encoding polypeptides of interest into cells, transduction of cells with recombinant viruses, introducing exogenous purified polypeptides of interest into cells, introducing messenger RNAs encoding polypeptides of interest into the cells, contacting cells with a non-naturally occurring reagent that induces expression of an endogenous gene encoding a polypeptide of interest (e.g., Oct3/4, Sox2, Klf4, or c-Myc), or any other biological, chemical, or physical means to induce expression of a gene encoding a polypeptide of interest (e.g., an endogenous gene Oct3/4, Sox2, Klf4, or c-Myc). In additional examples, induced pluripotent stem cells may be produced using microRNA (miRNA) methods or gene knockdown methods that induce pluripotency. Production of induced pluripotent stem cells may also be achieved by other methods that result in the expression of markers of pluripotency and the capacity to form differentiated cells.

Embryonic stem cells (ESCs) may be isolated from the inner cell mass of a blastocyst about four-to-five days post-fertilization and are characterized by both pluripotency and self-renewal. As such, ESCs can be propagated indefinitely in an undifferentiated state. ESCs can also be obtained from previously isolated cells that have been propagated in culture for an indefinite period of time. ESCs can be obtained from blastocysts that are genotypically male or female. ESCs may be obtained from unfertilized eggs using parthenogenesis. In further examples, ESCs may be obtained through the use of somatic cell nucleus transfer (SCNT) or may be descended from a cell that underwent SCNT.

The ESCs may be collected from subjects with a variety of disease statuses. The cells can be collected from an embryo that is free of an adverse health condition. In other cases, the embryo may be identified by preimplantation genetic diagnosis (PGD) to have an elevated risk of developing a disease or disorder, e.g., a muscular degenerative disease such as muscular dystrophy, Huntington's disease, Merosin deficiency 1A, nemaline myopathy, and Spinal Muscular Atrophy (SMA). Examples of muscular dystrophy include Becker, congenital, facioscapulohumeral (FSH), myotonic (type I and II), oculopharyngeal, distal, myotonic muscular dystrophy, Duchenne muscular dystrophy, Limb-girdle muscular dystrophy, and Emery-Dreifuss muscular dystrophy. Duchenne and Becker muscular dystrophies are caused by a mutation of a gene located on the X chromosome and predominantly affect males, although females can sometimes have severe symptoms as well. Additionally, most types of muscular dystrophy are multi-system disorders with manifestations in body systems including the heart, gastrointestinal system, nervous system, endocrine glands, eyes and brain.

Pluripotent stem cells (e.g., induced pluripotent stem cells, embryonic stem cells) may be differentiated into skeletal muscle cells by contacting the pluripotent stem cells with one or more differentiation media. The methods provided herein include one-step methods of differentiating a pluripotent stem cell wherein a single agent, or single combination of agents provided at the same time, triggers the differentiation pathway. In some cases, the method may comprise introducing a nucleic acid into a pluripotent stem cell (e.g., via transfection, transduction, viral transduction, eletroporation, etc.) such that the pluripotent stem cell expresses the nucleic acid. In some cases, the method does not comprise introducing a nucleic acid into a pluripotent stem cell, or does not comprise transfecting a nucleic acid into a pluripotent stem cell, or does not comprise electroporating a nucleic acid into a pluripotent stem cell, or does not comprise transducing a nucleic acid (e.g., via viral vector) into a pluripotent stem cell, such that the nucleic acid is expressed by the cell and causes, or contributes to the differentiation of the pluripotent stem cell into a satellite cell or satellite-like cell. In some cases, the method comprises introducing a myogenic protein to the pluripotent stem cells. In some cases, the method does not comprise introducing a myogenic protein to the pluripotent stem cells.

In some examples, pluripotent stem cells may be plated and cultured by plating as single cells in appropriate culture medium, or by any method known in the art. In some cases, the pluripotent stem cells are contacted with the differentiation medium in a single step, thereby causing differentiation of the pluripotent stem cells into skeletal muscle precursor cells (e.g. satellite cells or satellite-like cells).

In general, the single-step contacting may comprise contacting the pluripotent stem cells with a single differentiation medium that is provided to the cells at once, or serially over time (e.g., via media changes). In some cases, the single-step contacting may comprise contacting the pluripotent stem cells with a single differentiation medium that is provided to the cells at different concentrations over time (e.g., media changes involving altering the concentrations of differentiation media). In some embodiments, the components present in the single differentiation medium are sufficient to cause the pluripotent stem cells to differentiate into satellite cells or satellite-like cells (e.g., cells with functional, structural, morphological, or expression marker characteristics resembling those of a naturally-occurring satellite cell). In some embodiments, the component(s) present in the single differentiation medium are sufficient to cause satellite cells or satellite-like cells to be generated from the pluripotent stem cells. In some cases, the components present in the single differentiation medium are sufficient to cause the pluripotent stem cells to differentiate into satellite cells or satellite-like cells when the cells are serially exposed to the components (e.g., via one or more media changes). In some cases, contacting the pluripotent stem cells with the single differentiation medium comprises continuously contacting the cells with the differentiation medium. In other cases, contacting the pluripotent stem cells with the single differentiation medium comprises sporadically or serially contacting the cells with the differentiation medium.

In some cases, the contacting comprises contacting the pluripotent stem cells with two or more different differentiation media. The two or more different differentiation media may comprise different compounds. In some cases, the two or more different differentiation media are 2 or more, 3 or more, 4 or more, 5 or more, 6 or more, 7 or more, 8 or more, 9 or more, or 10 or more different differentiation media.

The one or more pluripotent stem cells may be concurrently contacted by compounds of the differentiation medium, e.g., two or more compounds are administered to the pluripotent stem cells during an overlapping time-frame. For example, the pluripotent stem cells may be contacted with one compound on days 1-3 and with a second compound from days 2-5. In some cases, the one or more pluripotent stem cells may be simultaneously contacted by compounds of the differentiation medium. For example, the pluripotent stem cells may be contacted with two compounds during the same timeframe (e.g., contacted with two compounds for days 1-3). In some cases, the pluripotent stem cells are serially or sequentially contacted with two or more compounds of the differentiation media. For example, the pluripotent stem cells may be contacted with one compound on days 1-3 and with a second compound from days 4-6.

Differentiation of Pluripotent Stem Cells into Satellite Cells or Satellite-Like Cells Pluripotent stem cells may be cultured in a differentiation medium that contains one or more chemical compounds that induce the cells to differentiate into satellite cells or satellite-like cells. In general, the differentiation medium is a myogenic induction medium. In some cases myogenic induction medium may contain serum-free M2 medium and 5% horse serum and may be supplemented with compounds including, but not limited to the Wnt pathway activator CHIR99021 (LC Laboratories), Alk5 inhibitor (a TGF-βreceptor inhibitor) (Sapphire Bioscience), hr-EGF, insulin, dexamethasone (Sigma-Aldrich), Y27632 (a Rho-associated kinase inhibitor) and ascorbic acid. In a preferred embodiment myogenic induction medium may contain 3 µM CHIR99021, 2 µM Alk5 inhibitor, 10 ng/ml hr-EGF, 10 µg/ml insulin, 0.4 g/ml dexamethasone, 10 µM Y27632 and 200 µM ascorbic acid.

In some cases, a compound or set of compounds within a myogenic induction medium provided herein may be able to directly induce the differentiation of satellite cells or satellite-like cells from one or more pluripotent stem cells. For example, in some cases, a Wnt pathway activator and a TGF-β receptor inhibitor may, together, be capable of causing the generation of satellite cells or satellite-like cells from pluripotent stem cells without the addition of an additional differentiation agent.

In some cases, myogenic induction medium used to differentiate pluripotent stem cells into satellite cells or satellite-like cells may include a medium comprising: a basal medium, a Wnt activator, and a TGF-β receptor inhibitor. In some cases, the skeletal muscle induction medium may include a ROCK inhibitor, a serum component, or a combination thereof. In some cases, the myogenic induction medium may include a LRRK2 inhibitor. Often, the myogenic induction medium provided herein is growth factor free.

The basal medium that is used in examples of the myogenic induction medium may vary, but generally comprises a nutrient-replete medium. Examples of basal media that may be used include, but are not limited to: MCDB 120, Skeletal Muscle Cell Basal Medium (manufactured by Promocell), SkBM Basal Medium (manufactured by Lonza), SkBM-2 Basal Medium (manufactured by Lonza), Stem Cell Technologies 'APEL Medium' (manufactured by Stem Cell Technologies), or DMEM/F12.

According to the methods provided herein, satellite cells or satellite-like cells may be differentiated in vitro from pluripotent stem cells incubated in myogenic induction medium. The satellite or satellite-like cells may be differentiated by incubating pluripotent stem cells in myogenic induction medium in a 37° C., 5% $CO_2$ incubator for at least about 7 days, 8 days, 9 days, or 10 days. During differentiation to satellite cells or satellite-like cells myogenic induction medium may be replaced on the pluripotent stem cells every day or every other day.

Differentiation of Satellite Cells or Satellite-Like Cells into Myoblast or Myoblast-Like Cells Satellite cells and satellite-like cells are myoblast precursors. Satellite cells or satellite-like cells may be obtained from any method known in the art. In some cases, satellite cells or satellite-like cells may be produced in vitro by differentiating pluripotent stem cells. In some cases the satellite cells or satellite-like cells may be primary cells obtained directly from mammalian subjects or cadavers.

As used herein, the term "satellite-like cell" refers to any cell that possesses structural or functional features associated with a naturally-occurring satellite cell (e.g., satellite cell within an organism such as a human) but yet also possesses at least one structural or functional feature distinguishing the satellite-like cell from a naturally-occurring satellite cell. In preferred embodiments, a satellite-like cell is a cell that is (a) produced in vitro from a pluripotent stem cell (e.g., Embryonic stem cell (ES cell) or induced pluripotent stem cell (iPS cell) or (b) derived from a satellite-like cell, such as cells resulting from proliferation of a satellite-like cell. As used herein, the term "satellite cell" refers to a cell that possesses the structural and functional features exhibited by a naturally-occurring satellite cell, and may or may not possess at least one structural or functional feature that distinguishes it.

After satellite cells or satellite-like cells have been produced or obtained they may be seeded for culturing in vitro. The satellite or satellite-like cells may be seeded at a density of about $5 \times 10^3$ cells/$cm^2$. In some examples, the cells may be seeded at a density of from about $1.5 \times 10^3$ cells/$cm^2$ to about $10^4$ cells/$cm^2$; from about $2 \times 10^3$ cells/$cm^2$ to about $10^4$ cells/$cm^2$; from about $3 \times 10^3$ cells/$cm^2$ out $10^4$ cells/$cm^2$ from about $4 \times 10^3$ cells/$cm^2$ to about $10^4$ cells/$cm^2$; or from about $10^3$ cells/$cm^2$ to about $9 \times 10^3$ cells/$cm^2$.

Satellite cells or satellite-like cells may be cultured directly on tissue culture-grade plastic as a substrate. In some cases, satellite cells or satellite-like cells may be cultured on a coated substrate (e.g., substrate coated with fibronectin, extracellular matrix, collagen, lamin, gelatin, matrigel, geltrex or combinations thereof). In some cases, satellite cells or satellite-like cells may be cultured on a substrate coated with collagen type I.

Satellite cells or satellite-like cells may be grown in cultures in a 37° C., 5% $CO_2$ incubator at an oxygen level equal to that of the atmosphere. In some cases, satellite cells or satellite-like cells may be grown in cultures in a 37° C., 5% $CO_2$/5% $O_2$ incubator (e.g., under hypoxic conditions). Satellite cells or satellite-like cells may be grown in cultures for at least about 1 day, 2 days, 3 days, 4 days, 5 days, 6 days, 7 days, 8 days, 9 days, 10 days, 11 days, 12 days, 13 days, or 14 days. In a preferred embodiment, satellite cells or satellite-like cells are grown in culture until the cells are approximately 80% confluent. In some cases the satellite cells or satellite-like cells may be grown until the cells are approximately 60%, 65%, 70%, 75%, 80%, 85%, 90%, 95% or greater than 95% confluent.

Satellite cells or satellite-like cells may be grown in myoblast differentiation medium (e.g., Genea Biocells Myoblast Medium). Myoblast medium may contain serum-free M2 medium (Genea Biocells). Myoblast medium may contain 5% horse serum. In some cases, myotube medium may be supplemented with other factors, including, but not limited to: insulin, human recombinant epidermal growth factor (hr-EGF), human recombinant hepatocyte growth factor (hr-HGF) (Peprotech), human recombinant platelet-derived growth factor (hr-PDGF) (Peprotech), human recombinant basic fibroblast growth factor (hr-bFGF) (Miltenyi Biotec), oncostatin (Miltenyi Biotec), insulin-like growth factor 1 (Miltenyi Biotec), SB431542 (Miltenyi Biotec) and ascorbic acid. In a preferred embodiment, myoblast medium may contain serum-free M2 medium with 5% horse serum, 10 µg/ml insulin, 10 ng/ml hr-EGF, 20 ng/ml hr-HGF, 10 ng/ml hr-PDGF, 20 ng/ml hr-bFGF, 20 µg/ml oncostatin, 10 ng/ml insulin-like growth factor 1, 2 µM SB431542, and 200 µM ascorbic acid.

Differentiation of Myoblast or Myoblast-Like Cells into Myotubes and Skeletal Muscle Cells The myoblasts or myoblast-like cells used to generate the myotubes or skeletal muscle cells provided herein may be obtained by any method known in the art. In some cases, myoblasts or myoblast-like cells may be grown in cultures in a 37° C., 5% $CO_2$/5% $O_2$ incubator (e.g., under hypoxic conditions). Myoblasts or myoblast-like cells may be grown in cultures for at least about 1 day, 2 days, 3 days, 4 days, 5 days, 6 days, 7 days, 8 days, 9 days, 10 days, 11 days, 12 days, 13 days, 14 days, 3 weeks, 4, weeks, 5 weeks, or even longer.

Myoblasts or myoblast-like cells may be grown in myotube medium (e.g., Genea Biocells Myotube Medium). In some cases, myotube medium may be serum-free. For example, the myotube medium may contain DMEM, MCDB or RPMI 1640 medium.

In some cases, the myotube medium may comprise serum. For example, the serum may be horse serum, bovine serum, calf serum, or other serum known in the art. In some cases, the myotube medium may contain at least 0.5%, 1%, 2%, 3%, 5%, 7%, 10%, 15%, or 20% serum (e.g., horse serum). In some cases, the myotube medium may contain less than 0.5%, 1%, 2%, 3%, 5%, 7%, 10%, 15%, or 20% serum, e.g., the myotube medium may contain 0.5%-8% serum (e.g., horse serum). In some particular cases, myotube medium may contain 5% horse serum (Thermo Fisher Scientific Life Sciences).

In some cases, myotube medium may be supplemented with other factors, including, but not limited to, insulin, oncostatin, necrosulfonamide and/or ascorbic acid. In some cases, myotube medium may contain insulin in a concentration of at least about 1 µg/ml, 2 µg/ml, 3 µg/ml, 4 µg/ml, 5 µg/ml, 6 µg/ml, 7 µg/ml, 8 µg/ml, 9 µg/ml, 10 µg/ml, 11 µg/ml, 12 µg/ml, 13 µg/ml, 14 µg/ml, 15 µg/ml, 16 µg/ml, 12 µg/ml, 18 µg/ml, 19 µg/ml, or 20 µg/ml. In some cases, myotube medium may contain oncostatin in a concentration of at least about 5 µg/ml, 6 µg/ml, 7 µg/ml, 8 µg/ml, 9 µg/ml, 10 µg/ml, 11 µg/ml, 12 µg/ml, 13 µg/ml, 14 µg/ml, 15 µg/ml, 16 µg/ml, 17 µg/ml, 18 µg/ml, 19 µg/ml, 20 µg/ml, 21 µg/ml, 22 µg/ml, 23 µg/ml, 24 µg/ml, 25 µg/ml, 26 µg/ml, 27 µg/ml, 28 µg/ml, 29 µg/ml, or 30 µg/ml. In some cases myotube medium may contain necrosulfonamide at a concentration of at least about 5 nM, 10 nM, 15 nM, 20 nM, 25 nM, 30 nM, 35 nM, 40 nM, 45 nM, 50 nM, 55 nM, 60 nM, 65 nM, 70 nM, 75 nM, 80 nM, 85 nM, 90 nM, 95 nM, or 100 nM. In some cases, myotube medium may contain ascorbic acid in a concentration of at least about 10 µM, 25 µM, 50 µM, 75 µM, 100 µM, 125 µM, 150 µM, 175 µM, 200 µM, 225 µM, 250 µM, 275 µM, 300 µM, 325 µM, 350 µM, 375 µM, or 400 µM.

The myoblasts may be cultured in the same myotube medium over time, often with medium changes. In some cases, the myotube medium may be changed or added to daily. In some cases, the myotube medium may be changed or added to every other day, twice-a-week, once-a-week, every two weeks, every three weeks or longer.

Introducing genetic modifications into FSHD-affected skeletal muscle cells according to the methods provided herein may create useful tools for developing both cell and drug therapies to treat subjects that have FSHD or other muscular deficiencies. For example, skeletal muscle cells may be genetically modified to correct a mutation associated with FSHD and then transplanted into a subject that has or is suspected of having FSHD in order to ameliorate the subject's symptoms. In some cases, skeletal muscle cells may be genetically modified to have a mutation that is known or suspected to cause a genetic muscle disease. Such genetically modified skeletal muscle cells may function as a platform for drug screening drugs that may reverse or reduced the symptoms of the disease or for identifying candidate agents that modulate DUX4 expression.

The genetic modification may be introduced by any method known in the art, e.g., transfection, transduction, CRISPR-mediated. In some cases, the genetic modification may involve introducing a wild-type or mutated gene into the skeletal muscle cells or skeletal muscle precursor cells. In some cases, the genetic modification may involve deleting or mutating a wild-type or mutated gene in the skeletal muscle cells or skeletal muscle precursor cells.

A mutation or mutations that are known to cause genetic disease may be introduced into healthy stem cell lines that are subsequently differentiated into skeletal muscle cells according to the methods provided herein. For example, the dystrophin gene or part of the dystrophin gene, or one or more exons may be deleted in order to cause a frame-shift mutation or otherwise render the gene non-functional. Mutations may be heterozygous or homozygous, in male or female stem cell lines. The modified stem cell lines may be differentiated to myogenic precursor cells (e.g., satellite cells or satellite-like cells, myoblasts) and skeletal muscle cells. The resulting myogenic precursor cells and skeletal muscle cells may show disease-associated phenotypes caused by the introduced mutation(s). The genetically unmodified stem cell line may serve as an isogenic control which may be useful for drug screening, disease modeling, and disease research.

The methods described herein may comprise obtaining skeletal muscle cells or skeletal muscle precursor cells (e.g., myoblasts, satellite cells) directly from a subject with a genetic disease or disorder affecting the subject's muscle tissue. The skeletal muscle cells or skeletal muscle precursor cells may be genetically modified to correct the mutation. The genetically modified skeletal muscle precursor cells may be differentiated into skeletal muscle cells in vitro. In some cases the genetically modified skeletal muscle precursor cells may be introduced into the subject and may differentiate into skeletal muscle cells in vivo. In some cases the subject treated with genetically modified skeletal muscle precursor cells or genetically modified skeletal muscle cells may experience a reduction in symptoms associated with the genetic disease or disorder. In some cases the subject treated with genetically modified skeletal muscle precursor cells or genetically modified skeletal muscle cells may no longer experience symptoms associated with the genetic disease or disorder. In some cases, the subject treated with genetically modified skeletal muscle precursor cells or genetically modified skeletal muscle cells may experience a temporary reduction in symptoms associated with the genetic disease or disorder.

Cells other than skeletal muscle precursor cells (e.g., blood cells, skin cells) may be obtained from a subject with a genetic disease or disorder and may be subjected to conditions that enable them to become pluripotent stem cells. In some cases, cells may be obtained from a subject with a genetic disease or disorder affecting the subject's muscle tissue (e.g., FSHD). The cells may be subjected to conditions enabling them to become pluripotent stem cells. For example, the cells may undergo de-differentiation and become induced pluripotent stem cells, particularly an induced pluripotent stem cell line. The pluripotent stem cells (or cell line) may be genetically modified to correct the mutation. For example, the subject may have one or more mutations in the dystrophin SMCHD1 gene and stem cells derived from the subject may be genetically modified to correct such mutations, or a portion of such mutations. The modified pluripotent stem cells may be differentiated into skeletal muscle cells or skeletal muscle precursor cells using the methods described herein. The modified skeletal muscle cells or skeletal muscle precursor cells may then be introduced into the subject with the genetic disease or disorder, in order to treat or ameliorate one or more aspects of the disorder.

Healthy skeletal muscle cells used according to the methods provided herein may be generated by treating FSHD-affected skeletal muscle cells with one or more compounds or agents to reduce or eliminate the FSHD phenotype.

According to methods disclosed herein, skeletal muscle cells may be treated with compounds or agents that include, but are not limited to, small molecules, organic compounds, peptides, peptoids, protein nucleic acids, antisense oligonucleotides, RNAs, and aptamers. Skeletal muscle cells may be treated with compounds or agents that target molecules that are known or suspected to be involved in epigenetic signaling. In some cases, skeletal muscle cells may be treated with compounds including, but not limited to, methyltransferase inhibitors. In some cases, skeletal muscle cells may be treated with histone methyltransferase inhibitors. In some cases, skeletal muscle cells may be treated with histone methyltransferase inhibitors, including, but not limited to, GSK126, EPZ5676, EPZ005687, GSK343, EI-1, CPI-360, CPI-169, UNC1999, GSK503, tazemetostat, BIX01294, a compound of Table 1, or a compound of any one of Formulas (I), (II), or (III).

Skeletal muscle cells of the present disclosure may be injected at a number of locations in the body of a subject. For example, the skeletal muscle cells may be injected at locations to access muscle formation, e.g. arm muscles such as coracobrachialis, biceps brachii, and brachialis, leg muscles such as tibialis anterior; extensor hallucis longus; extensor digitorum; and fibularis tertius, or other muscle locations.

In some examples, the skeletal muscle cells may be introduced to a subject via any of the following routes: parenteral, intravenous, intraarterial, intramuscular, subcutaneous, transdermal, intraperitoneal, or into spinal fluid. In particular, the cells may be introduced to the subject via direct injection of the cells into skeletal muscle of the subject.

In some cases, skeletal muscles may be introduced to a subject in combination with one or more compounds that reduce or eliminate the FSHD phenotype. In some cases, skeletal muscle cells may be introduced to a subject in combination with one or more methyltransferase inhibitors. In some cases, skeletal muscle cells may be introduced to a subject in combination with one or more histone methyltransferase inhibitors, including, but not limited to: GSK126, EPZ5676, EPZ005687, GSK343, EI-1, CPI-360, CPI-169, UNC1999, GSK503, tazemetostat, BIX01294, a compound of Table 1, or a compound of any one of Formulas (I), (II), or (III).

The methods provided herein involve the use of skeletal muscle cells that emulate or rescue the phenotype of FSHD-affected skeletal muscle cells. In some cases, the cells may be produced by the differentiation of pluripotent stem cells that are derived from various sources, including, but not limited to induced pluripotent stem cells and embryonic stem cells.

The methods provided herein include generating skeletal muscle cells or myogenic precursor cells that, when transplanted into a subject, rescue the phenotype of FSHD-affected skeletal muscle cells. Skeletal muscle cells or myogenic precursor cells that rescue the phenotype of FSHD-affected skeletal muscle cells may exhibit morphological characteristics similar to normal skeletal muscle cells. In some cases the skeletal muscle cells that rescue the phenotype of FSHD-affected skeletal muscle cells may have myotubes with diameters similar in size to the myotubes of normal skeletal muscle cells. In some instances, the skeletal muscle cells or myogenic precursor cells may have myotubes with maximal diameters of at least about 13 µm, 13.1 µm, 13.2 µm, 13.3 µm, 13.4 µm, 13.5 µm, 13.6 µm, 13.7 µm, 13.8 µm, 13.9 µm, 14.0 µm, 14.1 µm, 14.2 µm, 14.3 µm, 14.4 µm, 14.5 µm, 14.6 µm, 14.7 µm, 14.8 µm, 14.9 µm, 15.0 µm, 15.1 µm, 15.2 µm, 15.3 µm, 15.4 µm, 15.5 µm, or larger. In some instances the skeletal muscle cells that rescue the phenotype of FSHD-affected skeletal muscle cells may have myotubes that are similar in length to the myotubes of normal skeletal muscle cells. In some instances, the skeletal muscle cells may have myotubes that have a length of at least about 400 µm, 405 µm, 410 µm, 415 µm, 420 µm, 425 µm, 430 µm, 435 µm, 440 µm, 445 µm, 450 µm, 455 µm, 460 µm, 465 µm, 470 µm, 475 µm, 480 µm, 485 µm, 490 µm, 495 µm, 500 µm, 505 µm, 510 µm, 515 µm, 520 µm, 525 µm, 530 µm, 535 µm, 540 µm, 545 µm, 550 µm, 555 µm, 560 µm, 565 µm, 570 µm, 575 µm, 580 µm, 585 µm, 590 µm, 595 µm, 600 µm, 605 µm, 610 µm, 615 µm, 620 µm, 625 µm, 630 µm, or longer. In some instances, the skeletal muscle cells that rescue the phenotype of FSHD-affected skeletal muscle cells may have the same number of nuclei per myotube as normal skeletal muscle cells. In some instances the skeletal muscle cells may have at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more nuclei per myotube.

In some cases, the transcription profile of skeletal muscle cells that, when transplanted into a subject, rescue the phenotype of FSHD-affected skeletal muscle cells may be different from the transcription profile of FSHD-affected skeletal muscle cells. In some cases, expression of specific genes is downregulated in skeletal muscle cells that rescue the phenotype of FSHD-affected skeletal muscle cells compared to expression of specific genes in FSHD-affected skeletal muscle cells. In some cases, expression of specific genes is downregulated in skeletal muscle cells that rescue the phenotype of FSHD-affected skeletal muscle cells compared to expression of specific genes in FSHD-affected skeletal muscle cells. In some cases, expression of DUX4 is downregulated in skeletal muscle cells that rescue the phenotype of FSHD-affected skeletal muscle cells compared to expression of DUX4 in FSHD-affected skeletal muscle cells.

The number of administrations of cell therapy treatment to a subject may vary. Introducing the skeletal muscle cells into the subject may be a one-time event; but in certain situations, such treatment may elicit improvement for a limited period of time and require an on-going series of repeated treatments. In other situations, multiple administrations of the cells may be required before an effect is observed. The exact protocols depend upon the disease or condition, the stage of the disease, and parameters of the individual subject being treated.

The dosage of skeletal muscle cells that may be transplanted into a subject may differ based on the disease or injury of the subject, the progression of the disease or injury of the subject, and the degree of severity of the disease or injury of the subject. Additionally, the number of treatments provided to a subject may vary. A single treatment may be administered to the subject or multiple treatments may be given to the subject. In some cases, the subject may be treated about 1, 2, 3, 4, 5, 6, 7, 8, 9, 10, 11, 12, 13, 14, 15, 20, 25 or more times with the cells provided herein. In some cases, the subject may be treated less than 1, 2, 3, 4, 5, 6, 7, 8, 9, 10, 15 or 20 times within a year period. The treatments themselves may also vary in the number of sites that are provided with skeletal muscle cells. In examples, a single treatment of skeletal muscle cell transplantation may include 1, 2, 3, 4, 5, 6, 7, 8, 9, 10, 20, 50 or 100 or more injection sites for the direct skeletal muscle injection of skeletal muscle cells. In some cases, a single dose of cells comprises about $10^1$, about 50, about $10^2$, about $5 \times 10^2$, about $10^3$, about $5 \times 10^3$, about $10^4$, about $5 \times 10^4$, $10^5$, about $5 \times 10^5$, about $10^6$, about $5 \times 10^6$, about $10^7$, about $5 \times 10^7$, about $10^8$, about $5 \times 10^8$, about $10^9$, about $5 \times 10^9$, about $10^{10}$, about $5 \times 10^{10}$, about $10^{11}$, about $5 \times 10^{11}$, or more cells. In some cases, a single dose of cells comprises at most $10^2$, at most $5 \times 10^2$, at most $10^3$, at most $5 \times 10^3$, at most $10^4$, at most $5 \times 10^4$, at most $10^5$, at most $5 \times 10^5$, at most $10^6$, at most $5 \times 10^6$, at most $10^7$, at most $5 \times 10^7$, at most $10^8$, at most $5 \times 10^8$, at most $10^9$, at most $5 \times 10^9$, at most $10^{10}$, at most $5 \times 10^{10}$, at most $10^{11}$, or at most $5 \times 10^{11}$ cells.

During transplantation of the skeletal muscle cells, drugs may be given to the subject during the same period of time. For example, drugs may be administered prior to, during, or subsequent to transplantation of skeletal muscle cells. Examples of drugs that may be administered to the subject include but are not limited to: drugs to treat the disease or injury to the subject, immunosuppressant drugs, or one or more compounds described herein that promote differentiation of myoblasts into mature mytubes. Exemplary immunosuppressive drugs include calcineurin inhibitors, such as cyclosporine or tacrolimus, mTOR inhibitors, such as sirolimus or everolimus, purine synthesis inhibitors or purine analogues, such as mycophenolate mofetil or azathioprine, or steroids, such as prednisone. In some cases, the drugs administered to the subject do not include an immunosuppressant drug, particularly when the subject is unlikely to reject the cell therapy (e.g., when the cells are derived from the subject's own cells).

Skeletal muscle cells may be administered using a variety of instruments, such as syringes. Skeletal muscle cells may also be injected with a buffer, such as saline, phosphate-buffered saline or serum. Skeletal muscle cells may be administered with antibiotics, such as vancomycin or levofloxacin.

Skeletal muscle cells may be administered alone or in combination with one or more compounds or agents. In some cases, skeletal muscle cells may be administered with one or more compounds or agents that may target molecules involved in epigenetic signaling. In some cases, skeletal muscle cells may be administered with one or more compounds or agents that are methyltransferase inhibitors. In some cases, skeletal muscle cells may be administered with one or more compounds that are histone methyltransferase inhibitors. For example, skeletal muscle cells may be administered with one or more compounds that are methyltransferase inhibitors, including, but not limited to, GSK126, EPZ5676, EPZ005687, GSK343, EI-1, CPI-360, CPI-169, UNC1999, GSK503, tazemetostat, BIX01294, a compound of Table 1, or a compound of any one of Formulas (I), (II), or (III).

V. Drug Screening

In addition to use in cell therapies, skeletal muscle cells that emulate the phenotype of FSHD-affected skeletal muscle cells (or other cell types) may be used as a platform for drug screening. In particular, drugs may be assayed to test effects on the phenotype of FSHD-affected skeletal muscle cells, including, but not limited to, effects on cell morphology, marker expression, nuclei number, and proliferation. In some cases, the phenotype is associated with muscle function. The skeletal muscle cells provided herein thus may also be useful for disease modeling and disease research. In some cases, the assays provided herein involve contacting muscle lineage cells (or other cell type) with an agent that induces DUX4 expression (e.g., decitabine, chaetocin) and then screening for candidate agents that reduce or eliminate the induction of DUX4 expression. In some cases, the assays provided herein involve contacting muscle lineage cells or other cell type with candidate agents in order to identify agents that enhance DUX4 expression. Such agents may be used in disease models of diseases or disorders associated with upregulated DUX4 expression, including FSHD.

FIG. 1 provides an overview of some steps in a drug screening assay. The steps may be performed in any combination and in any order that is useful; steps may be omitted or additional steps may be interspersed between the depicted steps. In some cases, cells that are screened are normal skeletal muscle cells 130 differentiated from a healthy stem cell line 100, 110, 120, 130 or obtained from a healthy subject. In some cases, cells that are screened are diseased skeletal muscle cells (e.g., FSHD skeletal muscle cells) 130 or cells differentiated from a diseased stem cell line 100, 110, 120, 130. Diseased skeletal muscle cells may include skeletal muscle cells that have particular genetic mutations associated with genetic diseases, such as FSHD. In some cases, the diseased skeletal muscle cells may be derived from a subject carrying a genetic mutation associated with a muscular degenerative disease or disorder. In some cases, the diseased skeletal muscle cells are genetically engineered to carry a mutation or mutations that cause or are associated with a muscular degenerative disease or disorder. The mutation may be identical to a mutation carried by a subject (e.g., a human subject), or may be substantially similar to such a mutation. The diseased skeletal muscle cells may be tested for phenotypes of disease. Effects of disease may be characterized at a cellular and tissue level and other assessments may be performed on the diseased skeletal muscle cells. Characterizing the effects of the disease may include, but not be limited to, assessing function and morphology of the skeletal muscle cells, assessing marker expression of the skeletal muscle cells, assessing proliferation of the skeletal muscle cells, assessing the number of nuclei per myotube, and assessing myotube length and diameter.

The screening assays may involve contacting cells with a library of compounds in order to identify candidates that induce DUX4 expression 140. In some cases a compound known to induce DUX4 expression (e.g., decitabine, chaetocin) is used to induce expression of DUX4 140. In the absence of such compound, the cells likely do not express significant amounts of DUX4 150. After DUX4 expression is detected, candidate compounds may be added to the cells, which are then analyzed for DUX4 expression. A reduction in DUX4 expression 170 (particularly when compared to a control 180) may indicate that the candidate compound has potential as a therapeutic for a muscular dystrophy (e.g., FSHD).

The libraries of compounds used in the disclosed screening assays may contain any number of agents, as well as any type of agent. In some cases, the library of compounds contains agents that target epigenetic signaling. In some cases, the compounds may include, without limitation, small molecules, peptides, peptoids, antisense oligonucleotides, RNA (e.g., siRNA), DNA, and aptamers.

According to the methods provided herein, small molecules that are known or suspected to target networks and pathways related to FSHD may be used for drug screening assays. The small molecules may have known or suspected targets that are involved in epigenetic signaling, including, but not limited to: DNA methyltransferases, histone acetyltransferases (e.g., GCNS/PCAF, GNAT related, Myst family, CBP/p300, TAF250 family, Src family), histone methyltransferases (e.g., KMT1A-KMT1F, MLL, DOT1, KMT3A-KMT3C, KMT5A, KMT5B, KMT6/EZH2, EZH1, KMT7/SET7&9, KMT8/RIZ1), kinases (e.g., Raf, MEK, ERK, Wee1, MST, AMPK, Haspin, VRK, Aurora A-C, PLK1-3, Chk1/2, PKCa/b/d/theta/epsilon/iota, MSK1/2, JNK1-3), MeCP2, MBD1-4, BET BRDs (e.g., BRD2, BRD3, BRD4, Bdf, Brg), Chromo-domain proteins (HP-1 like, polycomb-like, CHD-like), Tudor domain proteins (e.g., SMN), PHD finger proteins (e.g., CBD, ING2, DNMT3L, PHF6), 14-3-3 proteins, MBD2, TET, histone deacteylases (HDAC) Classes I-IV (e.g., HDAC1/2/3/8, HDAC4/5/7/9, HDAC6/10, Sirt1, Sirt2, Sirt3, Sirt4, Sirt5, Sirt6, Sirt7, HDAC11), lysine demethylases (e.g., LSD1/KDM1, JHMD/Jumonji (e.g., JHDM1A/B, JHMD2A/B, JHMD3A-D, JARID1A-D, UTX), protein phosphatases (e.g., PPP2CA, PPP2CB, PPP1C, PP1D, EYA1, EYA2, EYA3), poly (ADP-ribose) polymerase (PARP), hypoxia-inducible factor (HIF), Pim kinases, and Aurora kinases.

According to the methods provided herein, small molecules that are known or suspected to target networks and pathways related to FSHD may be used for drug screening assays. The small molecules may have known or suspected targets that are genes, including, but not limited to DUX4. The small molecules may have known or suspected targets that are involved in Wnt/Fz/beta-catenin signaling, telomere structure and telomerase activity and/or kinome signaling.

According to the methods provided herein, small molecules that are known or suspected to target networks and pathways related to FSHD may be used for drug screening assays. The small molecules may have known or suspected targets that are involved in cytoskeleton structure and/or JAK/STAT signaling, including, but not limited to: IGF 1R/InR, PI3K, Akt, mTOR, PKCs, Srk, FAK, Raf, MEK, ERK, ROCK kinases, integrins, NMDA/Ca2+, Tyk, JAK, p38, Pim1, Bcl-2, c-Myc, Cdks.

According to the methods provided herein, small molecules that are known or suspected to target networks and pathways related to FSHD may be used for drug screening assays. The small molecules may have known or suspected targets that are involved in cell cycle signaling, including, but not limited to: TGFb/Smad, GSK3b, Cdkl-7, Myc, Wee1, Aurora A, Plkl, Chk1/2, p53/Mdm2, ATM/ATR, Topol/II, Raf, c-Abl.

According to the methods provided herein, small molecules that are known or suspected to target networks and pathways related to FSHD may be used for drug screening assays. The small molecules may have known or suspected targets that are involved in apoptosis, including, but not limited to: TNF-a, IKKa/b, NFkB, Survivin, cIAP, Caspases 3/8/9, p53/Mdm2, JAK/STAT, PKC, Ras, Raf, ERK1/2, JNK, Bcl-2, Bcl-xL PI3K, Akt, DNA-PK, mTOR, p70S6K, ATM.

According to the methods provided herein, small molecules that are known or suspected to target networks and pathways related to FSHD may be used for drug screening assays. The small molecules may have known or suspected targets that are involved in metabolic signaling, including, but not limited to: PPAR, p450, Hsp, PDE, Hydroxylases, DHFR, Dehydrogenase, Phospholipase, carbonic Anhydrase, HMG-CoA Reductases, AhR, CK1/2, NAMPT, MAO, FAAH, CETP, IDO, RAR/RXR, FXR, LXR, ER, AR.

According to the methods provided herein, small molecules that are known or suspected to target networks and pathways related to FSHD may be used for drug screening assays. The small molecules may have known or suspected targets that are involved in ubiquitin signaling, including, but not limited to: proteasome, DUB, E1 activating, E2 conjugating, E3-ligases, p97.

The cells screened in such screening assays (and thus contacted with a candidate compound or agent) may be any type of cell known in the art, including primary cells and immortalized cells (e.g., cell lines). Often, the cells are muscle cells including, but not limited to: muscle precursor cells, satellite cells, skeletal muscle cells, myoblasts, and/or myotubes. The muscle cells may be healthy cells, while in other cases the cells are diseased or carry a mutation associated with a disease. Often the cells are derived from a subject with a muscle disease, such as FSHD. In particular cases, the cells are generated by differentiating a pluripotent stem cell (e.g., embryonic stem cell, induced pluripotent stem cell) into a satellite-cell, or other muscle precursor cell. Often, the satellite cells have the ability to give rise to other satellite cells or satellite-like cells or to differentiate into skeletal muscle cells to form functional skeletal muscle. In some cases, the cells are differentiated from the satellite cells or satellite-like cells to myoblasts or myotubes. The cells contacted with the candidate agent may be cells at any stage of differentiation. For example, the cells may be myoblast cells that have just entered the myoblast stage; in some cases, the cells are late-stage myoblast cells.

The assays provided herein may identify compounds based on their ability to modulate DUX4 expression, such as the ability to induce or inhibit expression of DUX4. The screening assays provided herein may have any of a number endpoints or read-outs. A common read-out used in the assays provided herein is DUX4 expression level (e.g., protein expression, mRNA expression). In some cases, the FSHD-affected cells are treated with a candidate compound and the expression of DUX4 is assessed (e.g., by immunostaining, video microscopy). In some cases, expression (particularly RNA) is assessed by an amplification reaction (e.g., Polymerase chain reaction (PCR), reverse-transcriptase PCR, real-time PCR, quantitative PCR). In some cases, the RNA level is detected by sequencing using any sequencing device known in the art.

In some cases, compounds may be identified based on their ability to modulate DUX4 expression in cells that contain a stably integrated DUX4 reporter gene. The DUX4 reporter gene may be stably integrated into cells using any method known in the art, including, but not limited to transfection with plasmid DNA and transduction with lentivirus. In some cases the DUX4 reporter gene may be stably integrated into pluripotent stem cells that may be differentiated into myogenic precursor cells (e.g., myoblasts, myotubes). The DUX4 reporter gene may, in some cases, encode a protein that may be easily detected when the reporter gene is expressed. In some cases the DUX4 reporter gene may encode a fluorescent protein (e.g., GFP, YFP, BFP, NeonGreen).

The methods provided herein include generating skeletal muscle cells or myogenic precursor cells that emulate the phenotype of FSHD-affected skeletal muscle cells. Such cells may be used, for example, in a drug screening assay described herein. Skeletal muscle cells or myogenic precursor cells that emulate the phenotype of FSHD-affected skeletal muscle cells may exhibit morphological defects compared to normal skeletal muscle cells. In some instances, the skeletal muscle cells that emulate the phenotype of FSHD-affected skeletal muscle cells may have myotubes with smaller diameters compared to the myotubes of normal skeletal muscle cells. In some instances, the skeletal muscle cells that emulate the phenotype of FSHD-affected skeletal muscle cells may have myotubes with maximal diameters of at most about 13.5 µm, 13.4 µm, 13.3 µm, 13.2 µm, 13.1 µm, 13 µm, 12.9 µm, 12.8 µm, 12.7 µm, 12.6 µm, 12.5 µm, 12.4 µm, 12.3 µm, 12.2 µm, 12.1 µm, 12 µm, 11.9 µm, 11.8 µm, 11.7 µm, 11.6 µm, 11.5 µm, 11.4 µm, 11.3 µm, 11.2 µm, 11.1 µm, 11 µm, 10.9 µm, 10.8 µm, 10.7 µm, 10.6 µm, 10.5 µm, 10.4 µm, 10.3 µm, 10.2 µm, 10.1 µm, 10 µm, or smaller. In some instances, the skeletal muscle cells that emulate the phenotype of FSHD-affected skeletal muscle cells may have shorter myotubes compared to the myotubes of normal skeletal muscle cells. In some instances, the skeletal muscle cells that emulate the phenotype of FSHD-affected skeletal muscle cells may have myotubes that have a length of at least about 400 µm, 395 µm, 390 µm, 385 µm, 380 µm, 375 µm, 370 µm, 365 µm, 360 µm, 355 µm, 350 µm, 345 µm, 340 µm, 335 µm, 330 µm, 325 µm, 320 µm, 315 µm, 310 µm, 305 µm, 300 µm, 295 µm, 290 µm, 285 µm, 280 µm, 275 µm, 270 µm, 265 µm, 260 µm, 255 µm, 250 µm, 245 µm, 240 µm, 235 µm, 230 µm, 225 µm, 220 µm, 215 µm, 210 µm, 205 µm, 200 µm, 195 µm, 190 µm, 185 µm, 180 µm, 175 µm, 170 µm, 165 µm, 160 µm, 155 µm, 150 µm, or shorter. In some instances, the skeletal muscle cells that emulate the phenotype of FSHD-affected skeletal muscle cells may have fewer nuclei per myotube than normal skeletal muscle cells. In some instances, the skeletal muscle cells that emulate the phenotype of FSHD-affected skeletal muscle cells may have at least about 1, 2, or 3 nuclei per myotube. In some instances, the skeletal muscle cells that emulate the phenotype of FSHD-affected skeletal muscle cells may have at most about 1, 2, 3 or 5 nuclei per myotube.

The methods provided herein include identifying compounds that rescue the phenotype of FSHD-affected skeletal muscle cells. In some cases the compounds that rescue the phenotype of FSHD-affected skeletal muscle cells may result in the cells having myotubes with diameters similar in size to the myotubes of normal skeletal muscle cells. In some instances, the skeletal muscle cells or myogenic precursor cells may have myotubes with maximal diameters of at least about 13 µm, 13.1 µm, 13.2 µm, 13.3 µm, 13.4 µm, 13.5 µm, 13.6 µm, 13.7 µm, 13.8 µm, 13.9 µm, 14.0 µm, 14.1 µm, 14.2 µm, 14.3 µm, 14.4 µm, 14.5 µm, 14.6 µm, 14.7 µm, 14.8 m, 14.9 µm, 15.0 µm, 15.1 µm, 15.2 µm, 15.3 µm, 15.4 µm, 15.5 µm, or larger. In some instances the compounds that rescue the phenotype of FSHD-affected skeletal muscle cells may result in myotubes that are similar in length to the myotubes of normal skeletal muscle cells. In some instances, the skeletal muscle cells with rescued phenotypes may have myotubes that have a length of at least about 400 µm, 405 µm, 410 µm, 415 µm, 420 µm, 425 µm, 430 µm, 435 µm, 440 µm, 445 µm, 450 µm, 455 µm, 460 µm, 465 µm, 470 µm, 475 µm, 480 µm, 485 µm, 490 µm, 495 µm, 500 µm, 505 µm, 510 µm, 515 µm, 520 µm, 525 µm, 530 µm, 535 µm, 540 µm, 545 µm, 550 µm, 555 µm, 560 µm, 565 µm, 570 µm, 575 µm, 580 µm, 585 µm, 590 µm, 595 µm, 600 µm, 605 µm, 610 µm, 615 µm, 620 µm, 625 µm, 630 µm, or longer. In some instances, the skeletal muscle cells with rescued phenotypes may have the same number of nuclei per myotube as normal skeletal muscle cells. In some instances the skeletal muscle cells may have at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more nuclei per myotube.

In some cases, the transcription profile of skeletal muscle cells that rescue the phenotype of FSHD-affected skeletal muscle cells may be different from the transcription profile of FSHD-affected skeletal muscle cells. In some cases, expression of specific genes is downregulated in skeletal muscle cells that rescue the phenotype of FSHD-affected skeletal muscle cells compared to expression of specific genes in FSHD-affected skeletal muscle cells. In some cases, expression of specific genes is downregulated in skeletal muscle cells that rescue the phenotype of FSHD-affected skeletal muscle cells compared to expression of specific genes in FSHD-affected skeletal muscle cells. In some cases, expression of DUX4 is downregulated in skeletal muscle cells that rescue the phenotype of FSHD-affected skeletal muscle cells compared to expression of DUX4 in FSHD-affected skeletal muscle cells.

The methods provided herein involve the use of skeletal muscle cells that emulate or rescue the phenotype of FSHD-affected skeletal muscle cells. In some cases, the cells may be produced by the differentiation of pluripotent stem cells that are derived from various sources, including, but not limited to induced pluripotent stem cells and embryonic stem cells.

The compounds or agents of this disclosure may be selected for use in methods of cell therapy, drug therapy and/or drug screening provided further herein. The compounds or agents may be selected for use in cell therapy, drug therapy, and/or drug screening by selecting compounds or agents that result in a reduction in DUX4 expression in cells contacted with the compound or agent. The compounds or agents may be assessed for ability to reduce DUX4 expression using gene expression data, immunofluorescence, or other methods known in the art.

Agents that Induce DUX4 Expression

This disclosure provides compounds or agents that induce DUX4 expression in muscle lineage cells (e.g., skeletal muscle cells, myotubes, myoblasts, satellite cells). Compounds or agents that induce DUX4 expression may include DNA methyltransferase inhibitors. Particular examples of such compounds or agents include decitabine (also referred to herein as "ASK10") and compounds that are structurally related to decitabine, including, but not limited to compounds shown in Table 2.

TABLE 2

Representative compounds that induce DUX4 expression

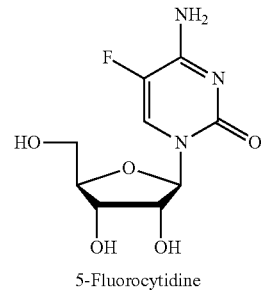

5-Fluorocytidine

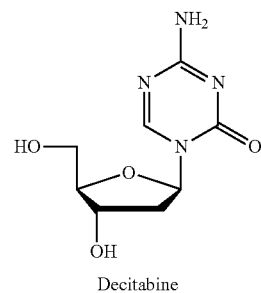

Decitabine

TABLE 2-continued
Representative compounds that induce DUX4 expression
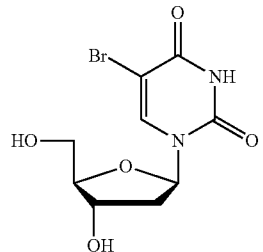
5-Bromo-2'-deoxyuridine
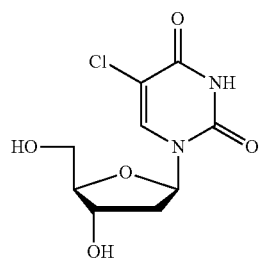
5-Chloro-2'-deoxyuridine
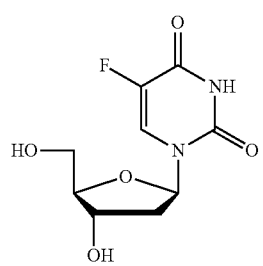
Floxuridine
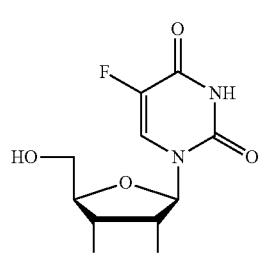
5-Fluorouridine
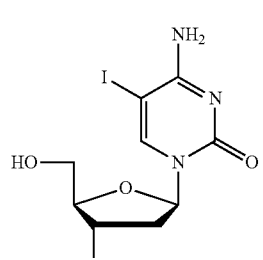
5-Iodo-2'-deoxycytidine
TABLE 2-continued
Representative compounds that induce DUX4 expression
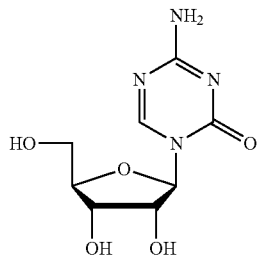
Azacitidine
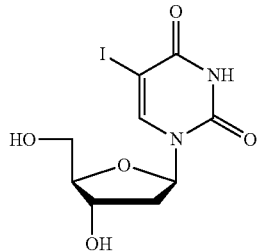
5-Iodo-2'-deoxyuridine
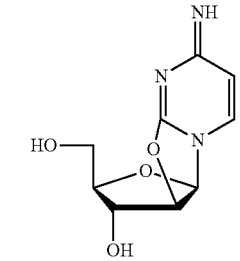
Ancitabine
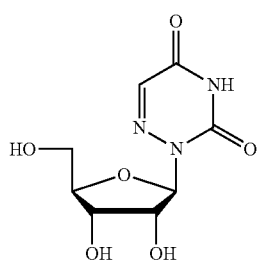
6-Azauridine
2'-Deoxy-thioguanosine TABLE 2-continued
Representative compounds that induce DUX4 expression
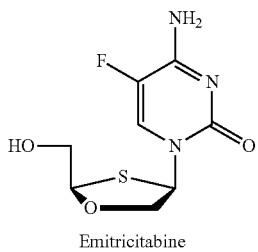
Emtricitabine
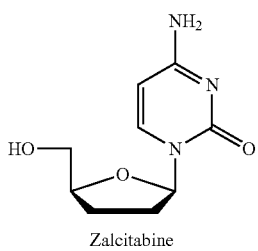
Zalcitabine
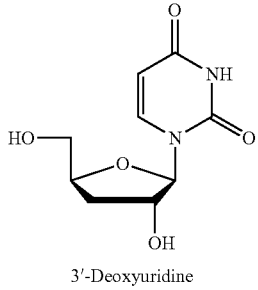 [SMILES: O=c1ccn([C@@H]2O[C@H](CO)C[C@@H]2O)c(=O)[nH]1]
3'-Deoxyuridine
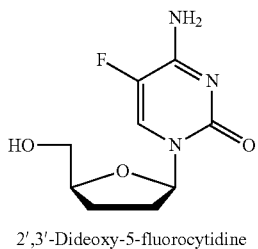
2',3'-Dideoxy-5-fluorocytidine
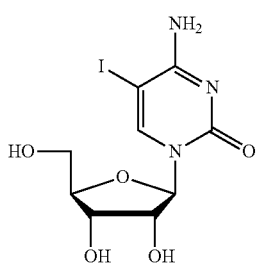
5-Iodocytidine
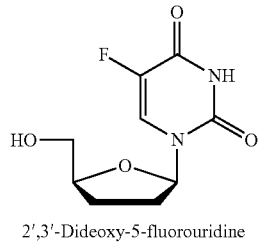
2',3'-Dideoxy-5-fluorouridine
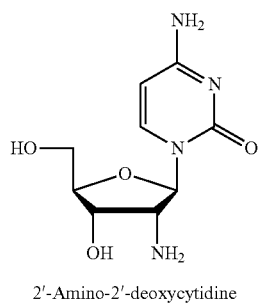
2'-Amino-2'-deoxycytidine
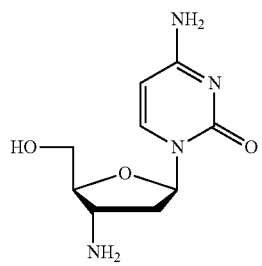
3'-Amino-2',3'-dideoxycytidine
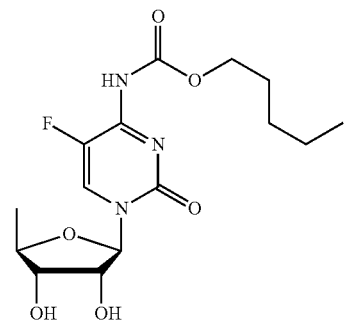
Capecitabine
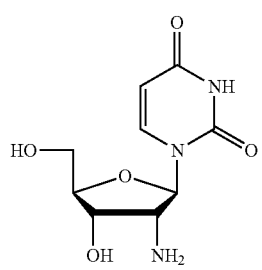
2'-Amino-2'-deoxyuridine TABLE 2-continued
Representative compounds that induce DUX4 expression
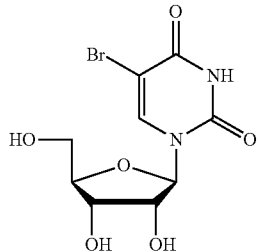
5-Bromouridine
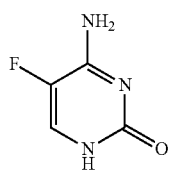
Flucytosine
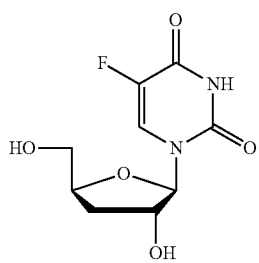
3'-Deoxy-5-Fluorouridine
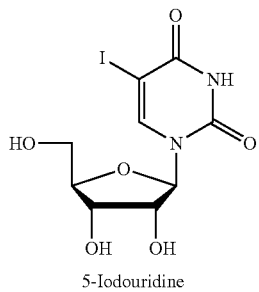
5-Iodouridine
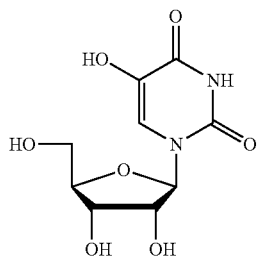
5-Hydroxyuridine
TABLE 2-continued
Representative compounds that induce DUX4 expression
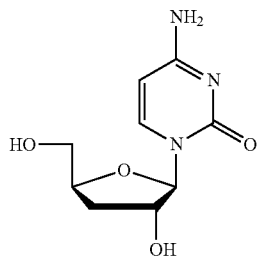
3'-Deoxycytidine
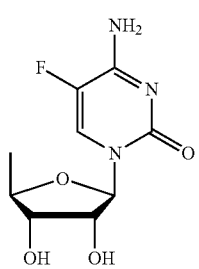
5'-Deoxy-5-fluorocytidine
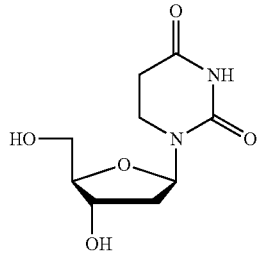
2'-Deoxy-5,6-dihydrouridine
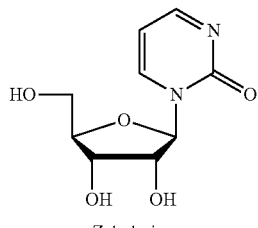
Zebularine
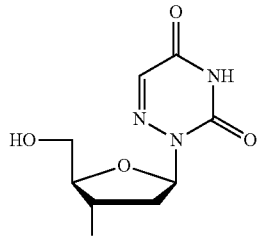
2'-Deoxy-6-azauridine TABLE 2-continued
Representative compounds that induce DUX4 expression
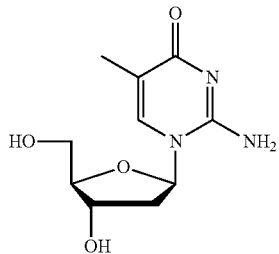
2'-Deoxy-5-methylisocytidine
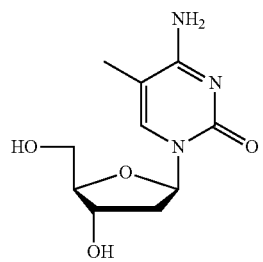
5-Methyl-2'-deoxycytidine
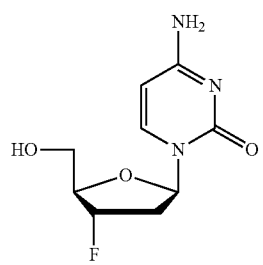
2',3'-Dideoxy-3'-fluorocytidine
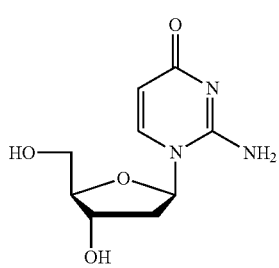
2'-Deoxyisocytidine
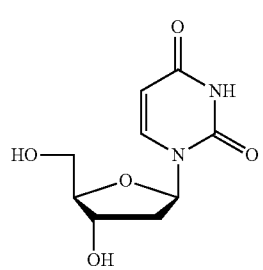
2'-Deoxyuridine
TABLE 2-continued
Representative compounds that induce DUX4 expression
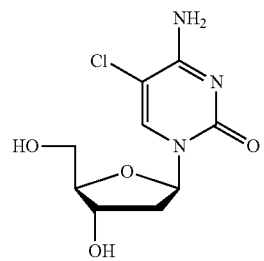
5-Chloro-2'-deoxycytidine
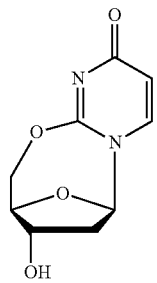
2,5'-Anhydro-2'-deoxyuridine
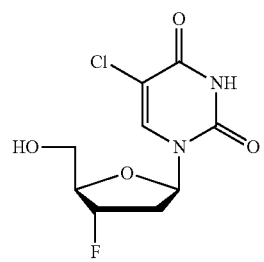
Raluridine
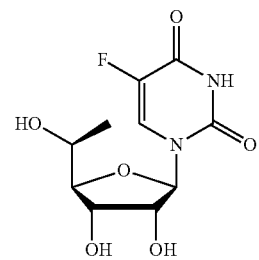
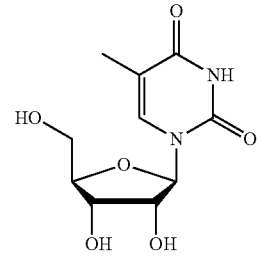

TABLE 2-continued
Representative compounds that induce DUX4 expression
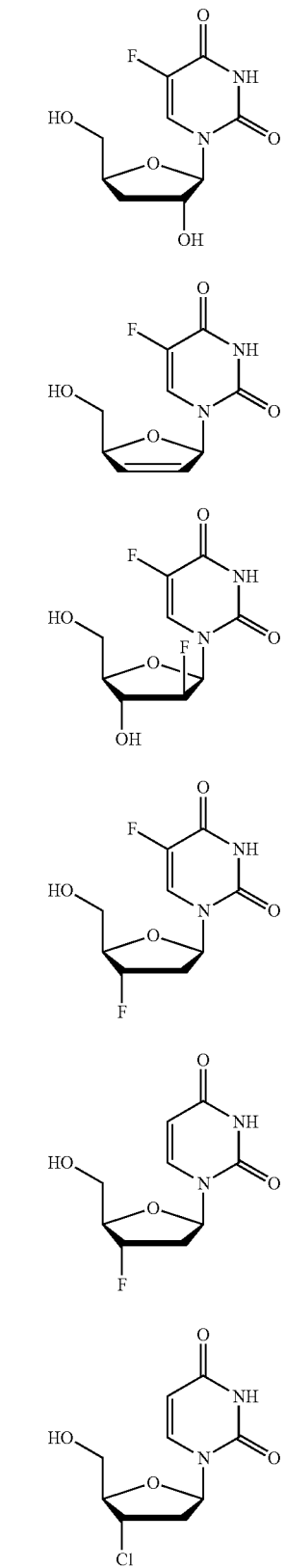
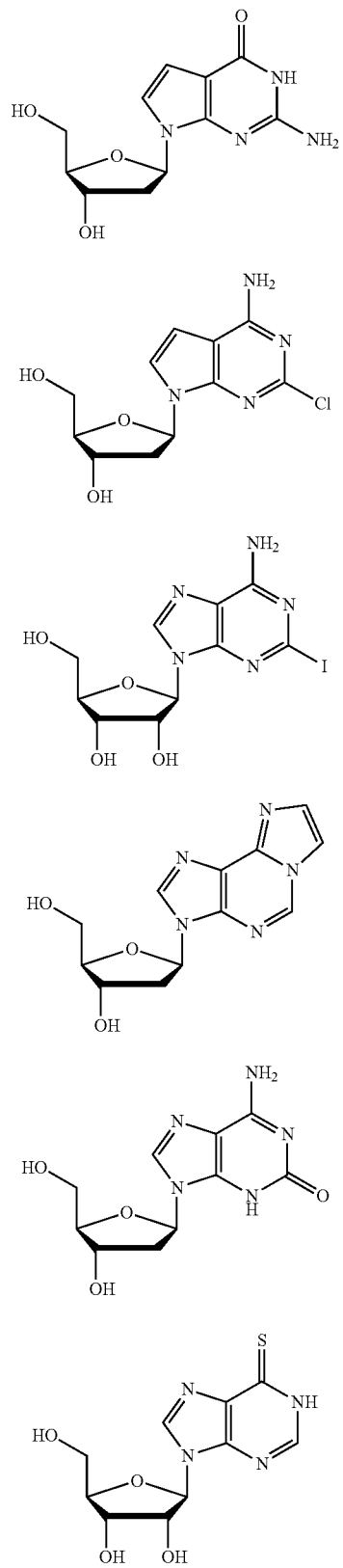

TABLE 2-continued

Representative compounds that induce DUX4 expression

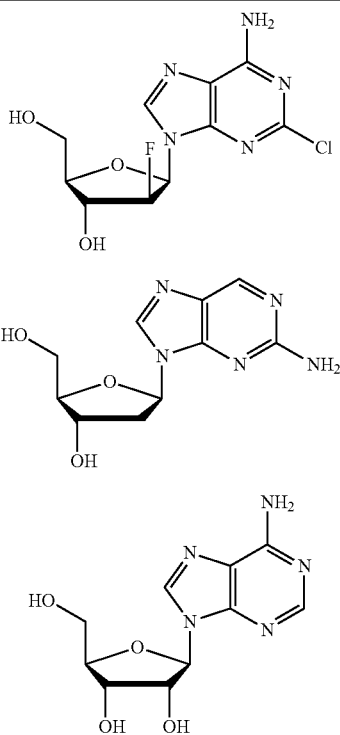

The DUX4 expression induced by the compounds or agents provided herein may resemble or mimic the expression of DUX4 that occurs in certain muscular deficiency disorders such as FSHD. In some cases, the expression level of DUX4 is greater than 1-fold, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 25-fold, 30-fold, or 40-fold increase over the level of DUX4 expression in a healthy muscle cell. In some cases, the DUX4 expression level is tuned to model FSHD at certain stages of disease. For example, the DUX4 expression may be at a level that is 0.25×, 0.5×, 0.75×, 0.9×, or about 1.0× the level of DUX4 typically expressed by a FSHD-afflicted muscle cell at height (or maximum point) of disease.

According to the methods provided herein, the compounds or agents may have a half maximal effective concentration ($EC_{50}$) of less than 5 μM. In some examples, the compound or compounds may have an $EC_{50}$ of less than about 5 μM, less than about 4 μM, less than about 3 μM, less than about 2 μM, less than about 1 μM, less than about 500 nM, or less than about 100 nM. In a preferred embodiment, the compound or compounds have an $EC_{50}$ of less than about 5 μM.

The compounds or agents of this disclosure may be selected for use in methods of cell therapy, drug therapy and/or drug screening provided further herein. The compounds or agents may be selected for use in cell therapy and/or drug screening by selecting compounds or agents that result in an increase in DUX4 expression in cells contacted with the compound or agent. The compounds or agents may be assessed for ability to induce DUX4 expression by gene expression data, immunofluorescence, or other methods known in the art.

In some cases, the compound is a DNA methyltransferase inhibitor. In some cases, the DNA methyltransferase inhibitor is a nucleoside analogue. In some cases, the nucleoside analogue is a ribonucleoside analogue. In some cases, the nucleoside analogue is a deoxyribonucleoside analogue. In some cases, the nucleoside analogue is an adenosine or deoxyadenosine analogue. In some cases, the nucleoside analogue is a guanosine or deoxyguanosine analogue. In some cases, the nucleoside analogue is a uridine or thymidine analogue. In some cases, the nucleoside analogue is a cytidine or deoxycytidine analogue. In some cases, the nucleoside analogue is decitabine or azacitidine. In some cases, the nucleoside analogue is selected from Table 2.

In another aspect, a method is provided for identifying specific methyltransferase family members that, upon inhibition, may result in blocking the induction of DUX4 and its targets. In some cases, a combination of RNAi knockdowns and forced expression may be used. In some cases, the expression of several suspect methyltransferase genes at the mRNA and protein levels in both normal and FSHD myoblasts in undifferentiated cells and during the course of differentiation can be detected. This information alone may provide sufficient detail for further refinement. For example, increased expression of one of the methyltransferase proteins during the course of differentiation may correlate with DUX4 de-repression and indicate that the methyltransferase protein is a candidate target.

As used herein, the terms "treat," "ameliorate," "treatment," and "treating" are used interchangeably. These terms refer to an approach for obtaining beneficial or desired results including, but are not limited to, therapeutic benefit and/or a prophylactic benefit. Therapeutic benefit means eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient can still be afflicted with the underlying disorder. For prophylactic benefit, treatment may be administered to a patient at risk of developing a particular disease, or to a patient reporting one or more of the physiological symptoms of a disease, even though a diagnosis of this disease may not have been made.

The term "about," as used herein and throughout the disclosure, generally refers to a range that may be 15% greater than or 15% less than the stated numerical value within the context of the particular usage. For example, "about 10" would include a range from 8.5 to 11.5.

The term "or" as used herein and throughout the disclosure, generally means "and/or" unless the context dictates otherwise.

VI. Examples

Example 1: Stem Cell-Based Disease Model and Compound Screening Strategy

A library of compounds was assembled targeting known or suspected epigenetic modifying enzymes as well as many additional targets, pathways and networks including but not limited to the kinome, Wnt/Fz/b-catenin, apoptosis, cytoskeletal signaling, the cell cycle. Lead-like compounds were obtained from several commercial providers including Med-Chem Express, Tocris and Selieck Chemicals. Together they represent about 5,000 modulators of known epigenetic "writer", "reader" and "eraser" proteins and other targets relevant to DUX4 toxicity or neuromuscular biology (Table 3).

Differentiation of FSHD myoblasts and a concomitant increase in FSHD-related biomarkers and phenoypes may represent a model of DUX4 de-repression that is amenable to screening compounds. Human embryonic stem cell lines listed in Table 4 were differentiated in a 3-step process to satellite-like cells, myoblasts and myotubes as described in PCT/AU2016/000144 and Caron, L. et al., Stem Cells Translational Medicine 2016; 5:1-17, which are hereby incorporated by reference in their entirety for all purposes.

Briefly, stem cell lines were cultured in commercially available media, mTeSR (Stem Cell Technologies) or M2 (Genea Biocells) and dissociated into single cells using Passaging Solution (Genea Biocells). Cells were plated in Myogenic Induction Medium to induce myogenic differentiation and incubated at 37° C. and 5% $CO_2$ for 7 to 10 days while performing media changes every other day. Once confluent, cells were dissociated into single cells using Passaging Solution and replated in Myoblast Medium (Genea Biocells) while performing media changes every other day. After 7-10 days the medium was switched to Myotube Medium (Genea Biocells) without any further media changes. After 4-7 days many multi-nucleated myotubes were observed and the cells were analyzed using a suitable assay.

Compounds (Table 3) were screened at concentrations of 1 µM and 300 or 100 nM and at different stages (FIG. 2): (1) compounds were added after the switch to Myoblast Medium and washed off after 24 hours by changing the culture medium to fresh Myoblast Medium; (2) compounds were added after the switch to Myoblast Medium and kept on the cells to the end of the differentiation process by performing all further media changes with media containing the compounds; (3) compounds were added after the switch to Myotube Medium and washed off after 24 hours by changing the culture medium to fresh Myotube Medium; and (4) compounds were added after the switch to Myotube Medium and no further media changes are performed.

Figure 2:
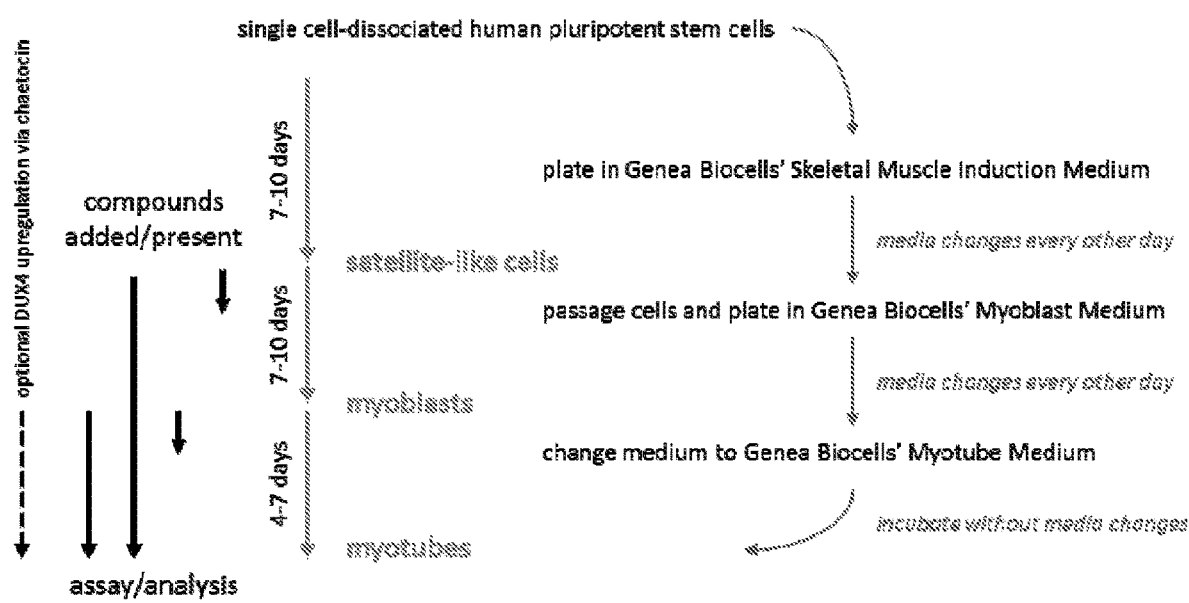
FIG. 2 is an overview depicting methods of differentiating human pluripotent stem cells to skeletal muscle.
Figure 3:
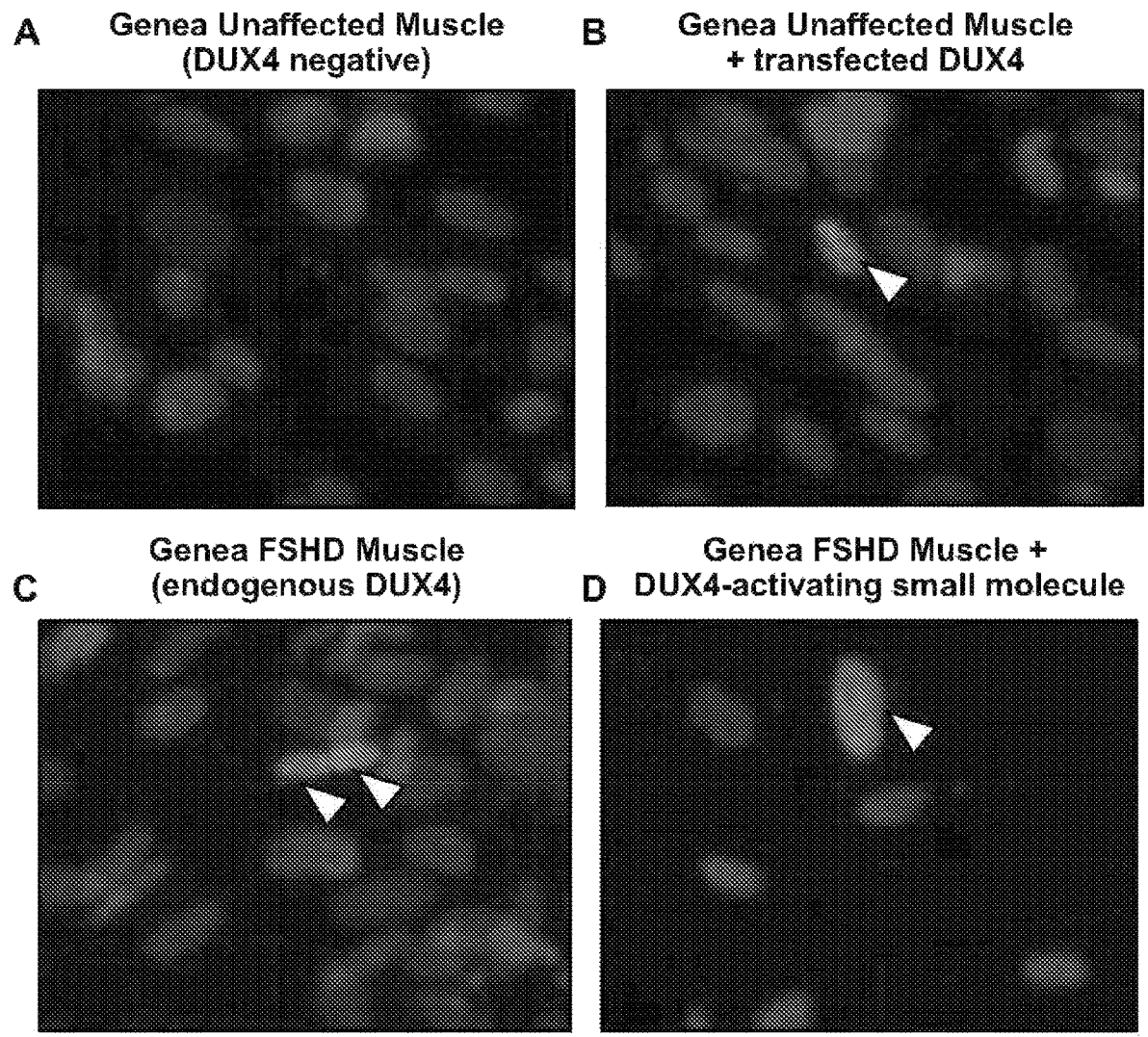
FIGS. 3A-D show the expression of DUX4 in nuclei of stem cell-derived myotubes by immunofluorescence staining in normal, DUX4-myotubes 3A; normal myotubes transfected with a DUX4 expression vector 3B; FSHD myotubes with endogenous DUX4 expression 3C; and FSHD myotubes exposed to a DUX4-activating small molecule 3D.
Figure 4A:
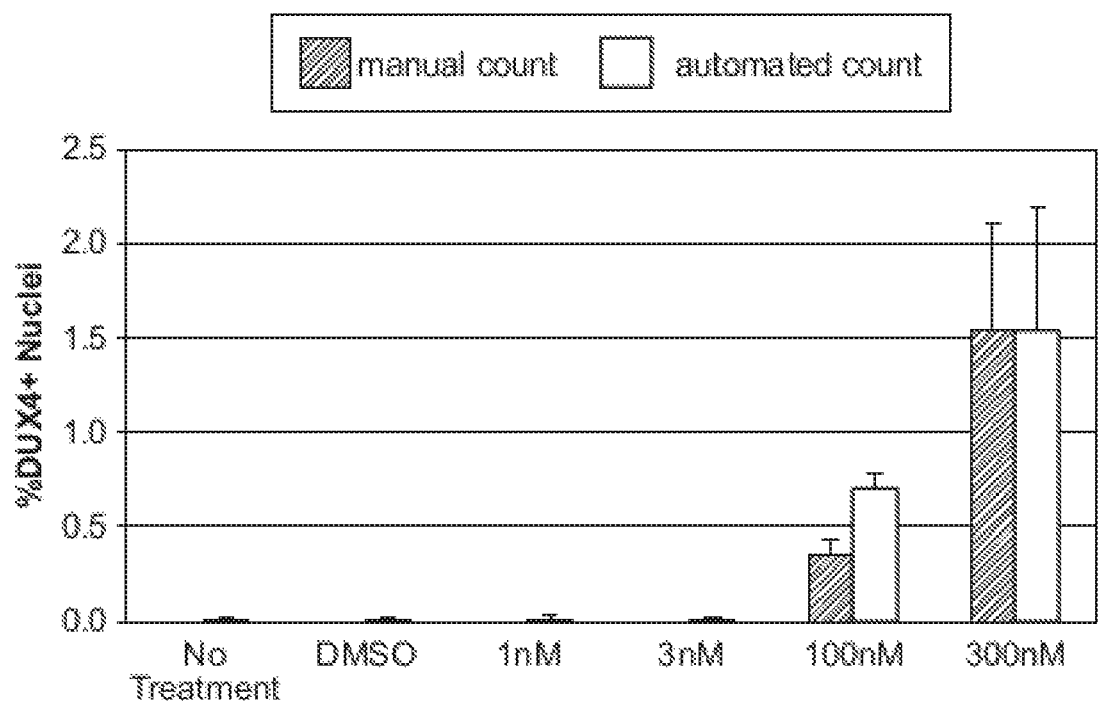
FIGS. 4A-B show the up-regulation of DUX4 expression in response to the chemical compound chaetocin; 4A depicts increases in the percentage of DUX4+ nuclei following exposure to chaetocin; 4B depicts the total nuclei count in the respective samples.
Figure 4B:
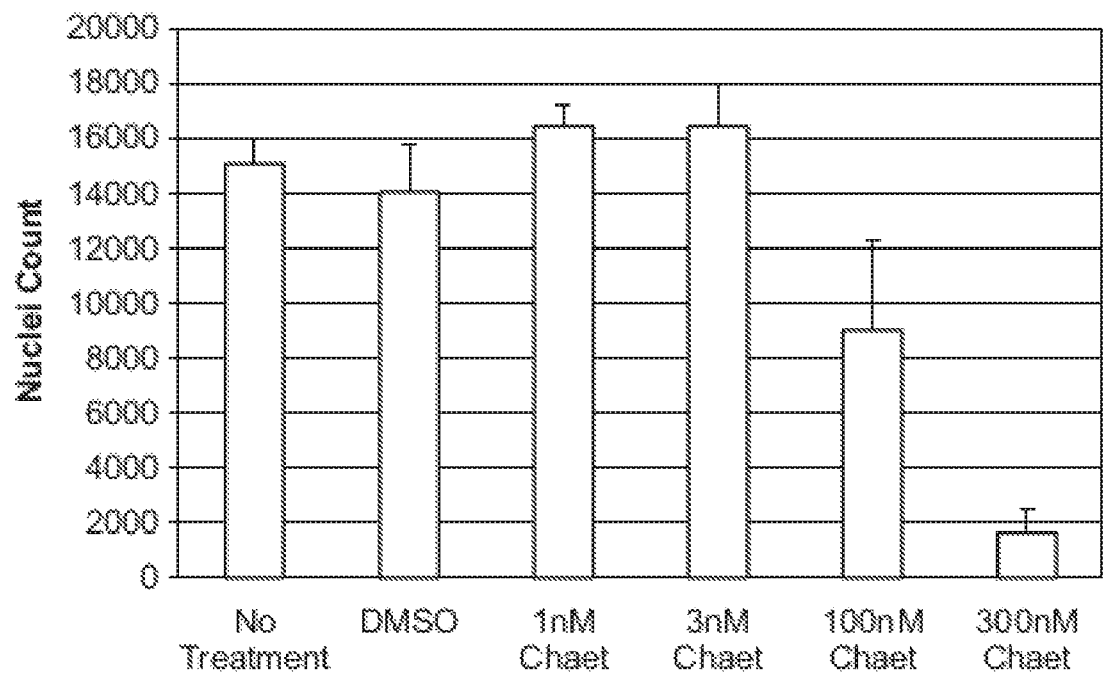

In myotubes from FSHD-affected cell lines DUX4 expression was observed by immunofluorescence staining using DUX4 E5-5 antibody, either spontaneously or by transfecting cells with a DUX4 expression vector (FIG. 3). In some cases, the expression of DUX4 in myogenic cells may be a rare event. Thus, to increase the assay window and sensitivity, chaetocin was used to increase the number of cells expressing DUX4 (FIG. 4A). A chaetocin concentration of 50-100 nM was found to induce DUX4 expression with only mild toxicity. In some examples, compounds may be screened in the presence of 50-200 nM chaetocin, a compound described to result in elevated levels of DUX4 expression in human myoblast cultures (FIG. 2).

TABLE 3

Partial list of compounds used in screen

| BioDiverse Set | | Epigenetics Set | |
|---|---|---|---|
| COMPOUND | TARGET | COMPOUND | TARGET |
| Dasatinib | Src | GSK J4 | JMJD3 and UTX |
| PD173074 | FGFR1/3 | GSK J1 | JMJD3 (KDM6B) and UTX (KDM6A) |
| RO4929097 | Notch | OG-L002 | LSD1 |
| Thiazovivin (TAV) | ROCK | IOX1 | IOX1 |
| Tacrolimus | PP2B | GSK-LSD1 | LSD1 |
| Amiodarone | IC blocker | ML324 | JMJD2 |
| Forskolin | PKA Act | Anacardic Acid | p300/CBP |
| TTNPB | RAR | Decitabine | DNA methylation |
| LDE225 Diphosphate | Hh | Azacitidine | DNA methylation |
| MLNM4924 | NAE | RG108 | DNA methyltransferase |
| 17-AAG | HSP90 | Thioguanine | DNMT1 |
| KY02111 | Wnt | Zebularine | DNA methylation |
| CHIR-99021 | GSK3b | Lomeguatrib | $O^6$-alkylguanine-DNA-alkyltransferase |
| PD98059 | MEK | Procainamide | DNA methyltransferase inhibitor |
| GW788388 | Alk5 | EPZ5676 | DOT1L |
| AR-42 | Epi | EPZ005687 | EZH2 |
| EPZ-6438 | Epi | GSK343 | EZH2 |
| Indomethacin | Notch | BIX 01294 | G9a histone methyltransferase |
| IOX2 | HIF-1a | EPZ-6438 | EZH2 |
| PluriSln1 | SCD1 (desaturase) inhibitor | CPI-360 | EZH1 |
| (R)-Rolipram | PDE4 | GSK503 | EZH2 |
| Lenalidomide | TNFa | CPI-169 | EZH2 |
| GSK429286A | ROCKI | EPZ015666 | PRMT5 |
| 1-Azakenpaullone | GSK3b | GSK126 | EZH2 |
| Sorafenib | Raf | El1 | EZH2 |
| Dinaciclib | CDKs | UNC0631 | histone methyltransferase G9a |
| GSK1059615 | PI3Ka | MI-2 | menin-MLL interaction |
| SR-3677 | ROCK | PFI-2 | SETD7 |
| PP1 | Src | 3-Deazaneplanocin A | S-adenosylhomocysteine hydrolase |
| Dexamethasone | Glucocorticoid Receptors | UNC1999 | EZH2 and EZH1 |
| TTP 22 | CK2 | SGC0946 | DOT1L |
| LH846 | CK1d | EPZ004777 | DOT1L |
| BIBR 1532 | Telomerase | I-BET151 | BRD2, BRD3 and BRD4 |

TABLE 3-continued

Partial list of compounds used in screen

| BioDiverse Set | | Epigenetics Set | |
|---|---|---|---|
| COMPOUND | TARGET | COMPOUND | TARGET |
| Decitabine | Epi | PFI-1 | BRD4 |
| EX 527 | Epi | I-BET-762 | BET proteins |
| OAC1 | Oct4 act | RVX-208 | BD2 |
| Rapamycin | mTOR Ant, BMP/Smad mod | OF-1 | BRPF1B and BRPF2 bromodomain |
| TSU-68 | PDGFR, FGFR, VEGFR | GSK1324726A | BRD2, BRD3, and BRD4 |
| LDN193189 (Hydrochloride) | BMP | PFI-3 | SMARCA2, SMARCA4 and PB1(5) |
| GSK126 | EZH2 | SGC-CBP30 | CREBBP/EP300 |
| PR-619 (DUBi) | Deubiquitinase DUB | Bromosporine | BRD2, BRD4, BRD9 and CECR2 |
| Reversine | MEK | UNC1215 | MBT (malignant brain tumor) |
| Pifithrin-a | p53 inh | OTX015 | BRD2, BRD3, and BRD4 |
| OTX-015 | Epi | CPI-203 | BET bromodomain inhibitor |
| Rosiglitasone (BRL 49653) | PPAR | EX527 | SIRT1 |
| Disulfiram | Aldehyde dehydrogenase | Nicotinamide | active component of coenzymes NAD and NADP |
| TWS119 | GSK3b | SRT2104 | SIRT1 |
| IOX1 | Epi | Roxadustat | HIF α prolyl hydroxylase inhibitor |
| Vorinostat | Epi | 2-Methoxyestradiol | HIF-1α |
| Gatifloxacin | DNA Gyrase | IOX2 | IHIF-1α prolyl hydroxylase-2 (PHD2) |
| 3-Deazaneplanocin | EZH2 | BAY 87-2243 | HIF-1 |
| GSK343 | Epi | Olaparib | PARP1/2 |
| KY02111 | Wnt | \veliparib | PARP1 and PARP2 |
| StemRegenin 1 | AhR | Rucaparib | PARP |
| JANEX-1 | JAK3 | Talazoparib | PARP |
| GNE-617 | NAMPT | G007-LK | TNKS1/2 |
| A-769662 | AMPK | AG-14361 | PARP1 |
| Sodium butyrate | Epi | INO-1001 | PARP |
| Pifithrin-u | p53/Bcl PPI | A-966492 | PARP1 and PARP2 |
| AZ191 | Dyrk1B | PJ34 | PARP |
| Bortezomib | Proteasome | Panobinostat | HDAC |
| Y-27632 (dihydrochloride) | ROCK | Mocetinostat | HDAC1 |
| IBMX | PDEs | CUDC-101 | HDAC, EGFR and HER2 |
| SB-505124 | Alk4, 5, 7 | Quisinostat | HDAC1, HDACs 2, 4, 10, and 11 |
| IWP-2 | Wnt | Tubastatin | HDAC6 |
| Purmorphamine | Hh | PCI-34051 | HDAC8i |
| EPZ005687 | Epi | RGFP966 | HDAC6 |
| IWP-L6 | Wnt | AR-42 | HDAC |
| KU-0063794 | mTOR | Rocilinostat | HDAC6 |
| Niclosamide | Wnt | BRD73954 | HDAC |
| Tranylcypromine | Epi | CAY10603 | HDAC6 |
| CYCLOHEXAMIDE | Epi | LMK-235 | HDAC4 and HDAC5 |
| PD0325901 | MEK | Nexturastat A | HDAC6 |
| BIX-01294 | Epi | TMP269 | THDAC4, HDAC5, HDAC7 and HDAC9 |
| GSK1838705A | Alk5/IGF1R | HPOB | HDAC6 |
| Etoposide | TopoII | Ruxolitinib | JAK1/2 |
| GSK1324726A | Epi | Tofacitinib | JAK3 |
| XAV-939 | Wnt | AZD1480 | JAK2 |
| EI1 | Epi | AT9283 | JAK2/3 |
| AMD 3465 (hexahydrobromide) | CXCR4 | Tofacitinib | JAK3 |
| CX-4945 | CK2 | Gandotinib | JAK2 |
| Taxifolin | EGFR, PI3K | NVP-BSK805 | JAK2 |
| Noscapine | Autophagy Ag | Cerdulatinib | JAK1/JAK2/JAK3/TYK2 and Syk |
| Cardionogen | Wnt | CEP-33779 | JAK2 |
| SB203580 | MAPK | Alisertib | Aurora A |
| LRRK-IN-1 | LRRK2 | VX-680 | Aurora A |
| GSK525768A | Epi | Barasertib | Aurora B |
| RG108 | Epi | Danusertib | Aurora A/B/C |
| BMS-378806 | gp120-CD4 | SNS-314 | Aurora A, Aurora B and Aurora C |
| MEK162 | MEK | PF-0381473 | Aurora A/B |
| UNC199 | EZH1/2 | MK-5108 | Aurora A |
| Kartogenin | Pheno | SGI-1776 | Pim1 |
| FK866 | NMPRT | STF-118804 | NAMPT |
| Vismodegib | Hh | FK866 | nicotinamide phosphoribosyltransferase (NMPRTase) |

TABLE 3-continued

Partial list of compounds used in screen

| BioDiverse Set | | Epigenetics Set | |
|---|---|---|---|
| COMPOUND | TARGET | COMPOUND | TARGET |
| Cilengitide | Integrin aVb3 | Tipifarnib | farnesyltransferase (FTase) |
| IQ1S | JNK3 | LB42708 | farnesyltransferase (FTase) |

TABLE 4

Human embryonic stem cell lines

| Cell Line | Karyotype | D4Z4 repeats |
|---|---|---|
| GENEA049 | 46, XX | 5 |
| GENEA050 | 46, XY | 5 |
| GENEA096 | 46, XX | 6 |
| GENEA019 | 46, XX | non-affected |
| GENEA002 | 46, XY | non-affected |
| GENEA015 | 46, XY | non-affected |

Example 2: Compound Screening Based on Phenotypic Markers

In one example, experiments are set up according to Example 1 with cells being cultured in collagen 1-coated optical bottom 96-well plates. At the end of the culture period cells are fixed with 4% formalin and immunofluorescence stained for DUX4, Ki67, MyoD and/or MF20 or MHC. FSHD myotube cultures are shown to contain more DUX4-positive, proliferating (Ki67-positive) cells, developmentally delayed (MyoD-positive) cells and forming thinner myotubes compared to normal controls. Staining with MF20 or MHC is used to visualize myotube morphology. High-content screening is performed to quantitatively measure the proportion of DUX4, Ki67 and MyoD-positive cells as well as myotube diameter and the number of nuclei per myotube. Hits are defined as compounds that significantly modulate FSHD-related phenotypic markers towards parameters observed in normal control cells.

In one example, methyltransferase inhibitors block DUX4 expression in undifferentiated FSHD myoblasts suggesting that specific inhibitors of methyltransferases can be used in a variety of different screening and therapeutic settings. Assays are performed up to 14 days after the cells are treated with the hi stone methyltransferase (HMT) inhibitors and DNA methyltransferase (DNMT) inhibitors for only 24 hours, thereby demonstrating that this effect is sustained, requiring longer than 7 days to recover after removal of the molecule from the cultures. This data may suggest that HMT inhibitors have therapeutic value in FSHD.

Continuous exposure of FSHD myoblasts and myotubes in culture to HMT inhibitors blocked expression of DUX4 and therefore results in decreased expression of DUX4 target genes. To determine the exposure-response relationship between HMT inhibitors and DUX4 expression (pharmacodynamics) in vitro, experiments are performed in both undifferentiated FSHD myoblasts and differentiated FSHD myotubes. To determine if continuous exposure for the entire culture period was required, FSHD1 myoblasts are treated with compounds for various lengths of time. DUX4 expression is sustained even when the compound is removed after 24 hours exposure (FIG. 2). This is surprising in that the drug treatment effect is sustained after removal of compound. Myoblast lineage genes (MYF5, MYOD1) are minimally affected by drug treatment. This unanticipated result is surprising and of importance because HMT inhibitors have not previously been demonstrated to have long lasting pharmacodynamic effects. Instead, they have been dosed daily in published studies, indicating a requirement for chronic exposure to compounds for sustained effects in animal models. Thus, in some cases, HMT inhibitors may be supplied for a pulse window (e.g., of 24 hours or less) and then withdrawn for a period of time longer than the pulse window (e.g., 7 days or longer). This may be explained by the infrequent and stochastic nature of DUX4 expression, which is detected in only a fraction of cells in culture at any given time (e.g., 1 in 1,000 cells). The results described herein may suggest that a 24 hour long pulse of HMT inhibition disrupts ongoing DUX4 expression that cannot resume after drug withdrawal. New DUX4 expression may be governed by the infrequent initiation that occurs due to mutations causing FSHD.

Normal cell lines (Genea 002 and Genea 015) and an FSHD-affected cell line (Genea 096) were cultured and differentiated according to Example 1. Compounds were added for 24 hours either at the beginning of the myoblast stage or at the end of the myoblast stage. Cells were further differentiated to myotubes and analyzed 7 days later at the end of the myotube stage (see FIG. 2) by immunofluorescence staining for MyoD, Ki67 and MF20. A DNA methyltransferase inhibitor, ASK10 (Compound #1) was highly toxic at higher doses but surprisingly less so for FSHD-affected cells (FIGS. 8A-8E). An analogue of Compound #1, Compound #1A1, was tested in a similar manner and was found to be much less toxic and nontoxic to FSHD-affected cells, even at the higher end of the tested dose range (FIGS. 9A-9E). Compound #1A1 also promoted myogenesis in a dose-dependent manner, particularly in FSHD-affected cells as measured by the proportion of cells expressing MF20 (FIGS. 9A-9E). A histone methyltransferase inhibitor, ASK19 (Compound #2) was not toxic but promoted myogenesis resulting in more MF20-positive cells and longer myotubes in all cell lines tested (FIGS. 10A-10E).

Example 3: Representative Active Compounds that Induce DUX4 Expression

In one example, experiments are set up according to Example 2 and cells are assessed for DUX4 expression. Representative active compounds that induce DUX4 expression by more than twice control at a half maximal effective concentration ($EC_{50}$) of less than 5 µM are shown in Table 2.

Example 4: Representative Active Compounds that Eliminate or Reduce DUX4 Induction In one example, experiments are set up according to Example 2 and cells are assessed for reduction of DUX4 induction. Representative active compounds that eliminate or reduce DUX4 induction at a half maximal effective concentration ($EC_{50}$) of less than 5 µM are shown in Table 1.

Example 5: Compound Screening by Targeted RNASeq or Other Relevant Technologies

Experiments are set up according to Example 1 with cells being cultured in collagen I-coated 96-well plates. At the end of the culture period, total RNA is extracted from each well. The concentration and integrity of each RNA sample is confirmed by measuring the absorbance at 260 nm and 280 nm and capillary electrophoresis (Bioanalyzer, Agilent Technologies). RNA samples are then analyzed by targeted RNASeq using the TruSeq system (Illumina) for a custom panel of genes (Table 5). Results are normalized to housekeeping genes (Table 5) and relative gene expression levels and statistical significance are calculated. Hits are defined as compounds that do not alter the expression pattern of muscle and myogenesis-related genes but modulate disease-associated genes, e.g. down-regulation of DUX4 target genes.

TABLE 5

Panel of myogenic and muscular dystrophy-associated biomarker genes selected for screening by targeted RNAseq

| | | |
|---|---|---|
| TBX6 | CHRNA1 | CAPN2 |
| Mesogenine | CHRNA3 | CASP3 |
| Pax3 | CDC42 | FBXO32 |
| Pax7 | CDCA8 | FOXO3 |
| Myf5 | CDKN1B | NOS2 |
| MyoD | CDKN2B | PPARGC1A |
| MyoG | CDK5R1 | PPARGC1B |
| MRF4 | FOXM1 | RPS6KB1 |
| MYH8 | CCND1 | TRIM63 |
| ACTA2 | NOTCH1 | AKT1 |
| ARHGEF6 | Dll1 | AKT2 |
| PFN2 | WNT2 | MAPK8 (JNK1) |
| LBP | WNT5A | MMP9 |
| NFIX | FRZB | NFKB1 |
| ERBB3 | TGFB | UTRN |
| MSTN | BMP4 | Pax 6 |
| BDNF | Col2A1 | nestin |
| BCL2 | Col19A1 | Alpha feto protein |
| CAV1 | Col1A1 | sox 17 |
| MEF2c | Col5A2 | nanog |
| IGF1 | Col6A1 | Oct-3/4 |
| TGM2 | Col6A2 | DMPK |
| NTM | Col6A3 | MBNL-1 |
| CILP | Col11A1 | MBNL-2 |
| PODXL | Col14A1 | LAP2 |
| AGTPBP1 | Col15Al | lamin B receptor |
| MBD3L2 | FBN1 | LMNA |
| TRIM43 | CAMK2G | SYNE2 gene |
| ZSCAN4 | CAPN3 | EDMD |
| COL2A1 | CAV3 | ACTA1 |
| ZNF296 | DAG1 | NEB |
| MEG3 | DMD | TPM2 |
| SPRYD5 | DYSF | TPM3 |
| EGFL6 | LMNA | TNNT1 |
| GSTT1 | MAPK1 (ERK2) | KBTBD13 |
| PRAMEF2 | SGCA | CFL2 |
| KHDC1L | MYH1 | KLHL40 |
| RYR1 | TNNC1 | KLHL41 |
| RYR3 | SLC2A4 (Glut4) | LAMA2 |
| SMCHD1 | GLUT1 | GLUT4 |
| | Housekeeping genes: | |
| GUSB | REEP5 | C1orf43 |
| VCP | GPI | |

Example 6: Compound Characterization Using DUX4 Reporters and Video Microscopy

Figure 5:
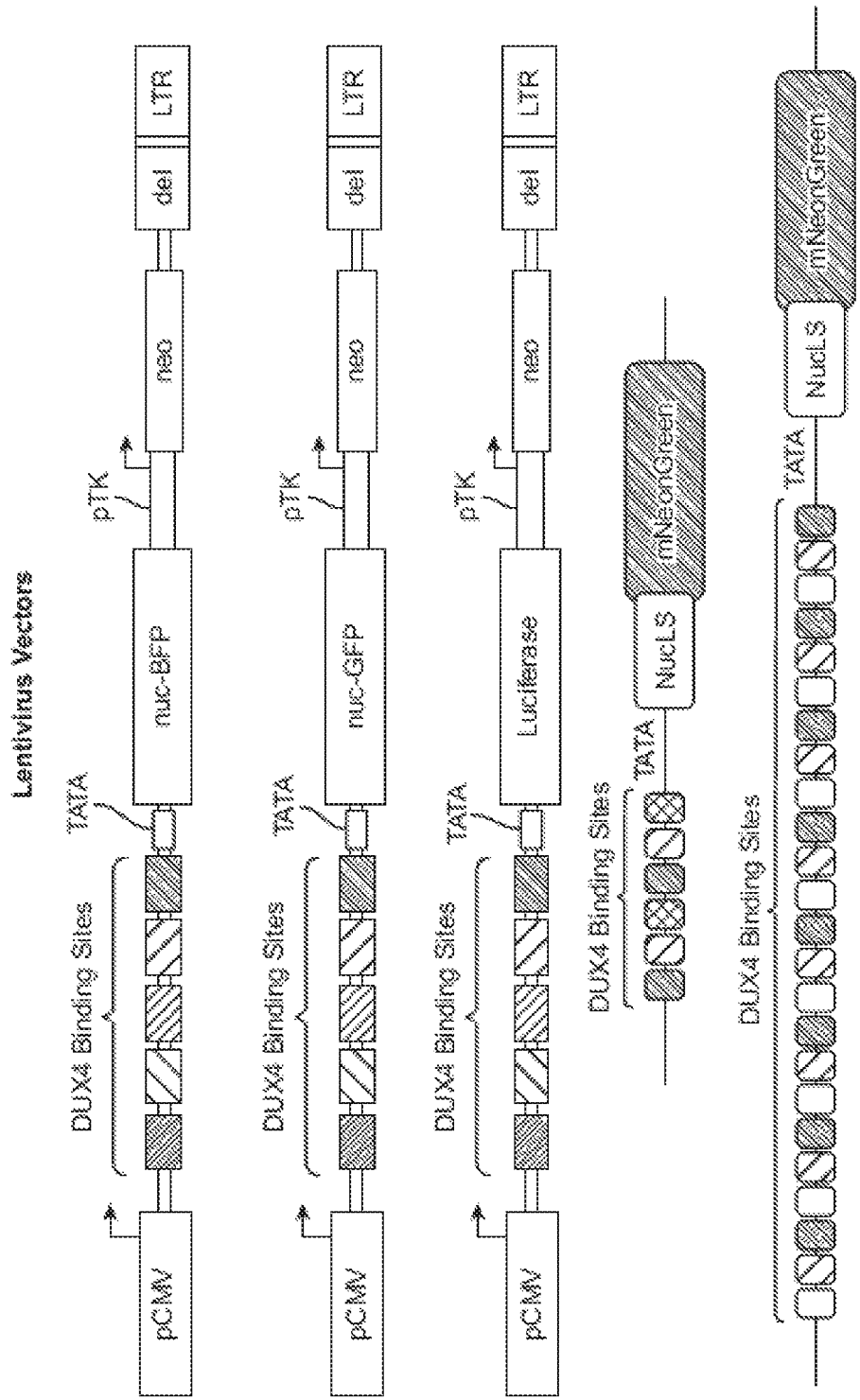
FIG. 5 shows lentivirus-based DUX4 reporter constructs that express BFP, GFP, luciferase, and NeonGreen.

Lentivirus constructs were used to stably integrate a DUX4 reporter into human embryonic stem cell lines (FIG. 5). Cells were plated in collagen I-coated 12-well plates (Corning BIOCOAT™-Cat #354500) in M2 hESC maintenance medium (Genea Biocells). Since cell lines grow at different rates and may optimally transduce at distinct cell densities, each line was plated at four different cell densities and transduced for 2 hours using a vector preparations diluted at 1:20 (50 ul/ml) in M2 medium containing 8 ug/ml polybrene. A pilot "kill curve" was established using the same non-transfected cell lines to help define the baseline antibiotic concentration required during the selection process. Based on the results, all transduced cells were selected with 300 ug/ml of G418 for at least 10 days. The antibiotic selected cells were further expanded in M2 (2× T175 flasks for each cell line) and samples were cryopreserved as stocks of 0.5 to 1×10$^6$ cells/vial.

Figure 6B:
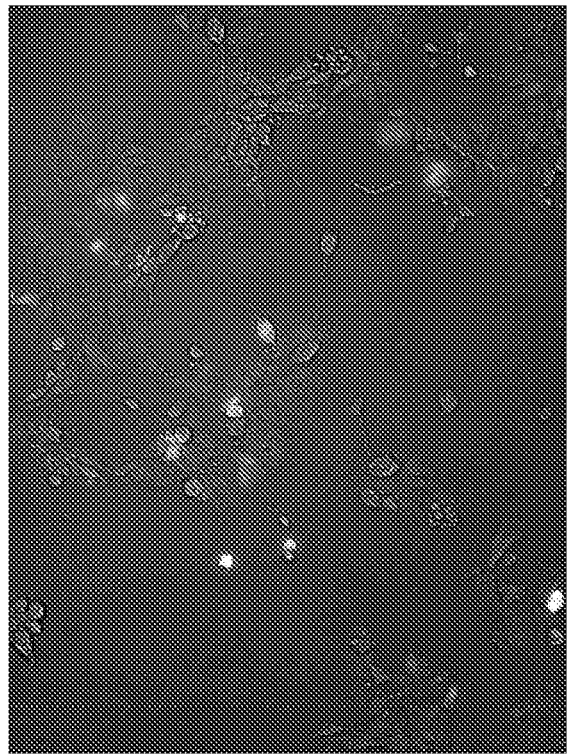
FIGS. 6A-B show human embryonic stem cell lines (6A, GENEA050 and 6B, GENEA049) stably selected for integration of the lentivirus reporter constructs; transient transfection with a DUX4-expression vector resulted in expression of the GFP reporter.
Figure 6A:
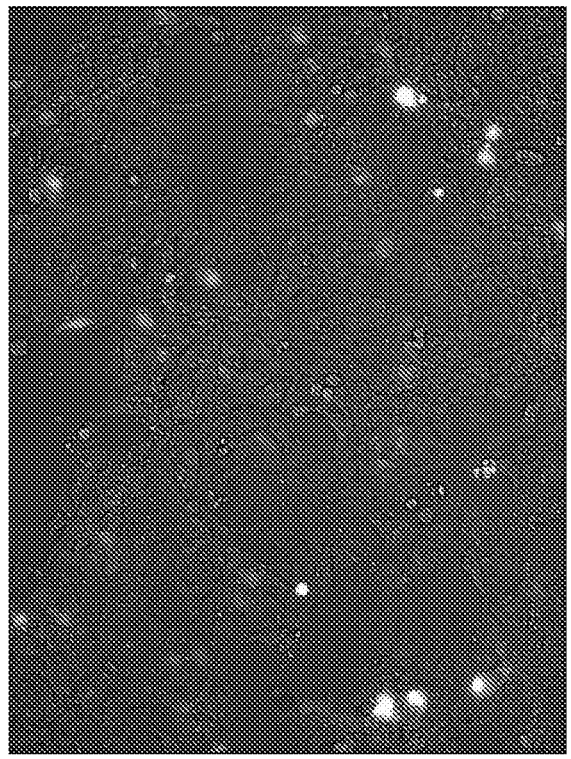
Figure 8A:
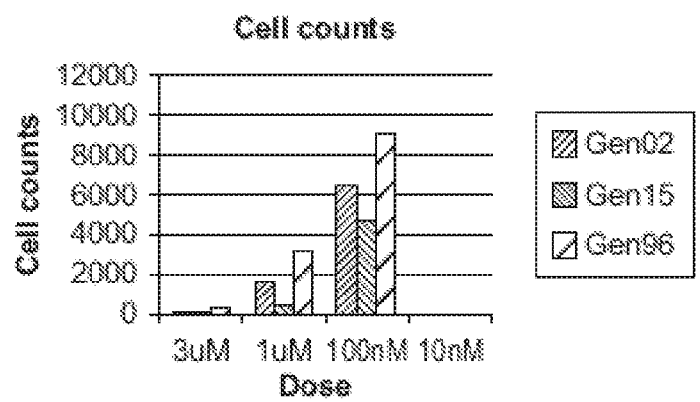
FIGS. 8A-8E illustrate the effects of a DNA methyltransferase inhibitor, ASK10 (Compound #1) on cell count 8A; MyoD expression 8B; MyoD expression in Ki67+ cells 8C and MF20+ cells 8D; and myotube length 8E in cells treated with Compound #1 for 24 hours at the beginning of the myoblast stage.
Figure 8B:
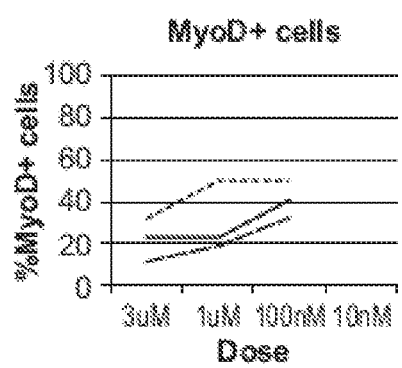
Figure 8C:
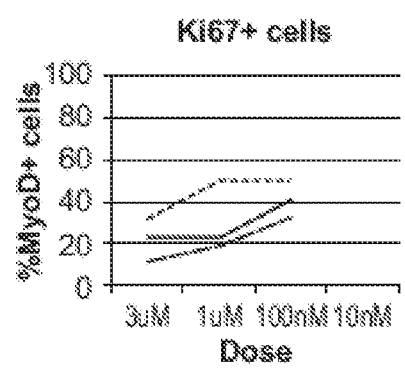
Figure 8D:
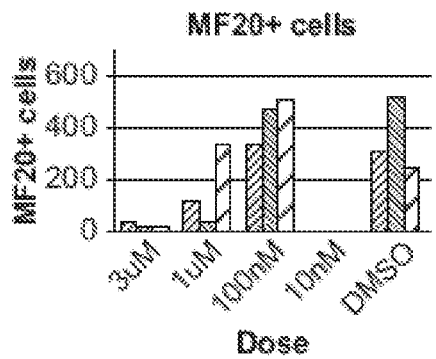
Figure 8E:
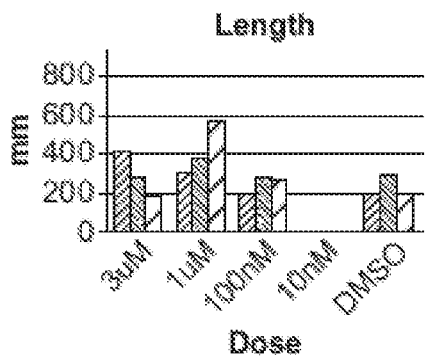

To validate the GFP reporter constructs, the pluripotent lines were initially transfected with a DUX4 expression vector4 (pCS2-mkgDUX4, see Snider L., et al., (2009) Hum Mol Genet. 18(13):2414-30, which is herein incorporated by reference in its entirety). As the overexpression of DUX4 was expected to be toxic, a titration of the DUX4 expression vector was carried out to allow the detection of fluorescence before cell death. GFP fluorescence was observed in isolated cells transfected with low titers of DUX4 plasmid (FIGS. 6A and 6B). An elevated level of DUX4 was visibly toxic to cells within a few hours post transfection. All transfected lines showed observable GFP expression.

The reporter cell lines were then differentiated to satellite-like cells using Myogenic Induction Medium (Genea Biocells). In FSHD-affected cells rare events of GFP-positive cells were observed and most of the green cells detected appeared to be dead or dying as was expected (FIG. 7).

In another example, experiments are set up according to Example 1 with FSHD-affected DUX4 reporter cells being cultured in collagen I-coated 96-well plates. Compounds that showed effects in previous examples are added in a dose range of 10 nM to 1 µM and at 3-8 different concentrations. The cells are continuously observed by time-lapse video microscopy (IncuCyte Zoom, Essen Bioscience) and the number of GFP-positive (DUX4-expressing) nuclei are detected and quantified throughout the culture period. Compounds show a dose-dependent effect in reducing the number of DUX4-expressing nuclei.

Figure 11A:
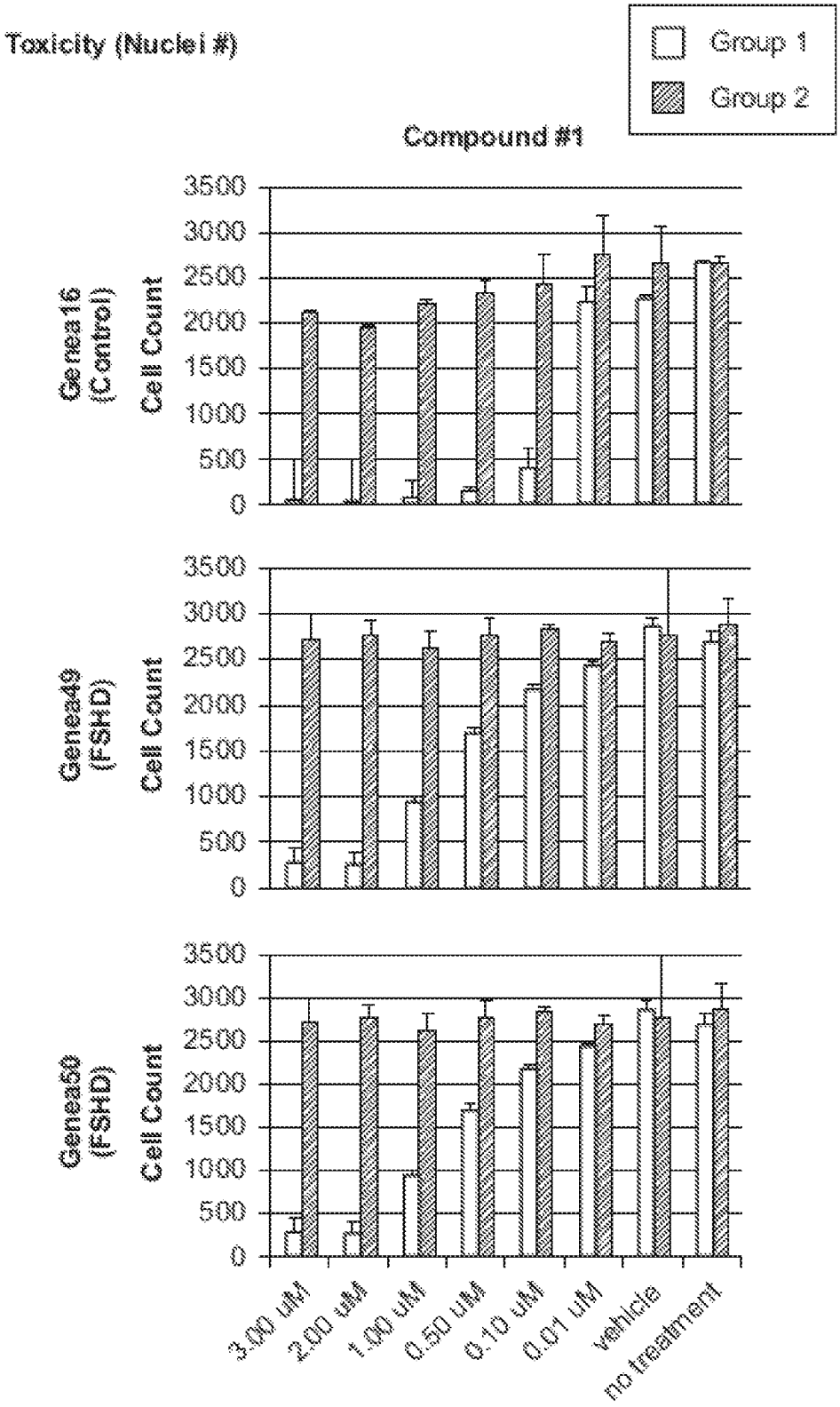
FIGS. 11A-11B show the effect on cell counts of the timing of cell contact with ASK10 (compound #1) 11A; and ASK19 (compound #2) 11B; cells in Group 1 were treated with compounds for 24 hours at the beginning of the myoblast stage; cells in Group 2 were treated with compounds for 24 hours at the end of the myoblast stage.
Figure 11B:
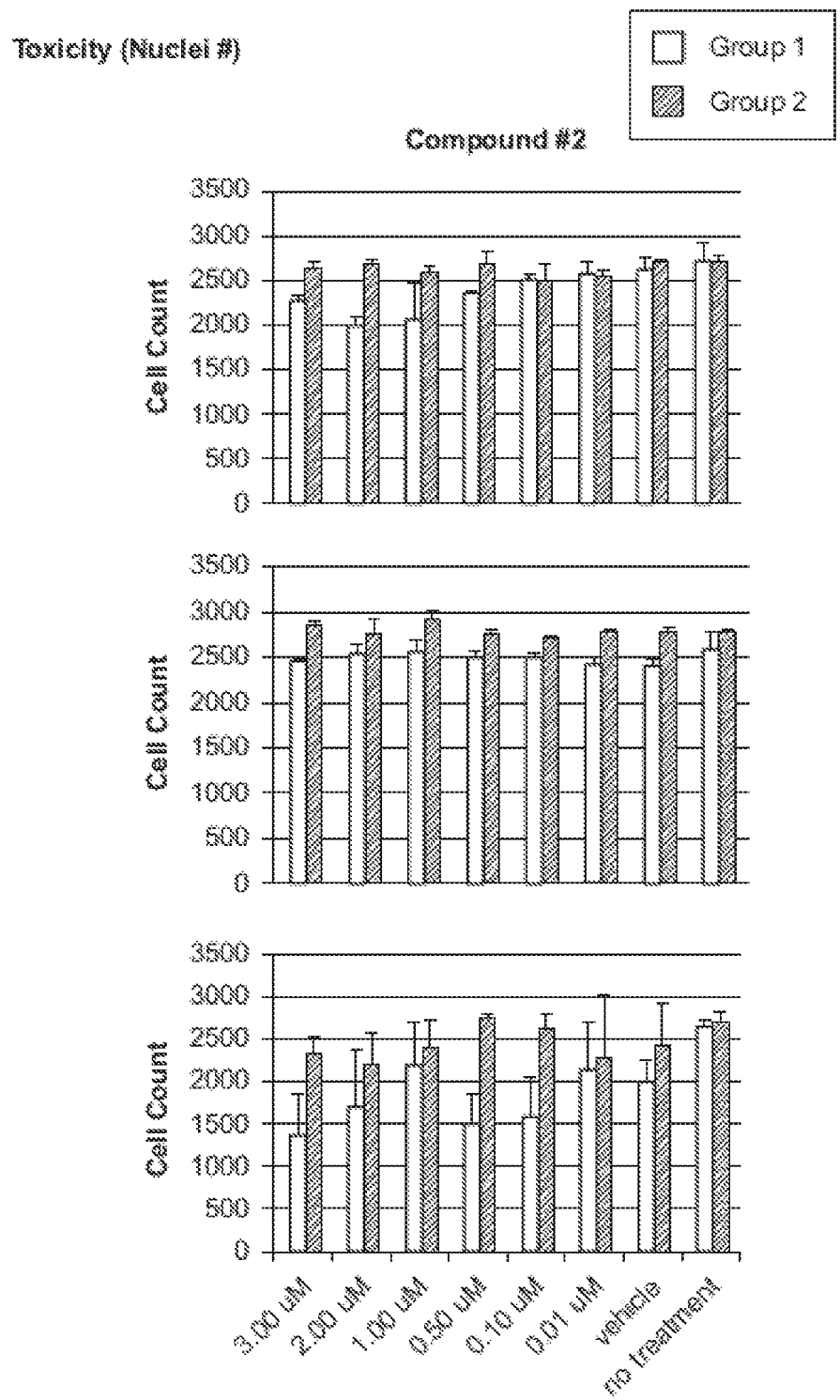
Figure 12A:
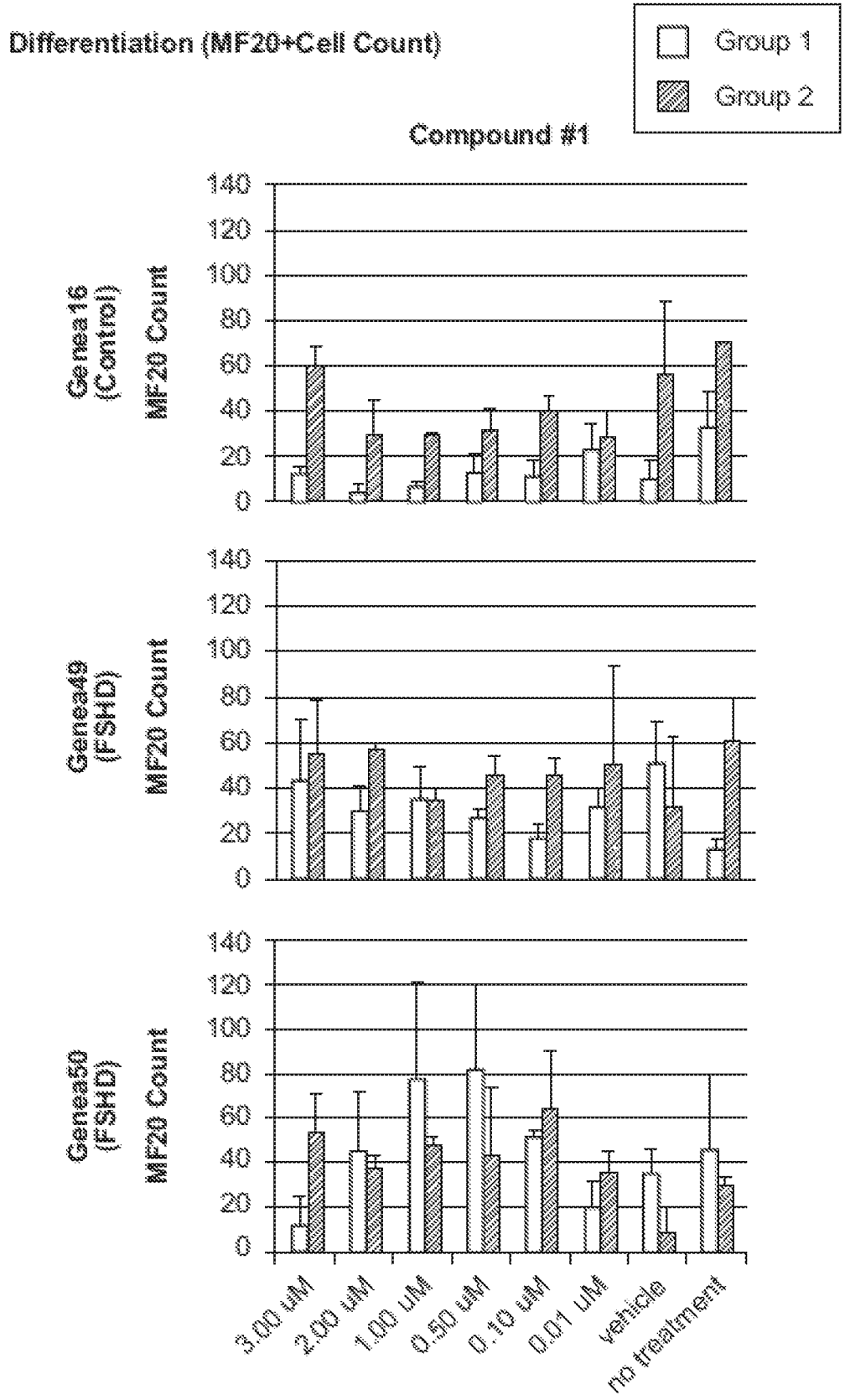
FIGS. 12A-12B show the effect on the number of MF20-positive myotubes observed of the timing of contact with ASK 10 (compound #1) 12A, and ASK 19 (compound #2) 12B; cells in Group 1 were treated with compounds for 24 hours at the beginning of the myoblast stage; cells in Group 2 were treated with compounds for 24 hours at the end of the myoblast stage.
Figure 12B:
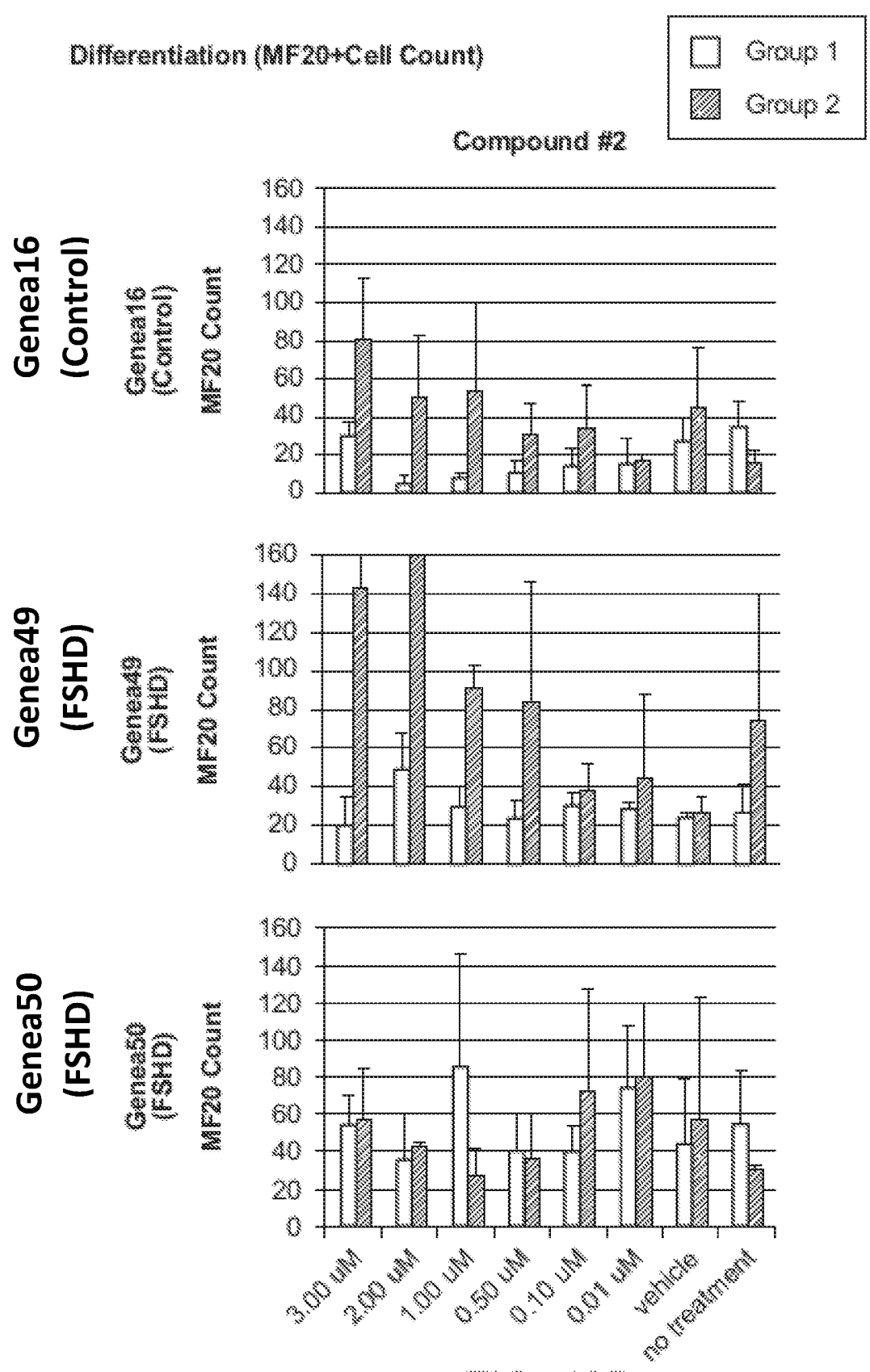

In another example, normal (Genea016) and FSHD-affected (Genea049 and Genea050) cell lines were differentiated according to Example 1. A DNA methyltransferase inhibitor (Compound #1) (ASK10) or a histone methyltransferase inhibitor (Compound #2) (ASK19) was added for 24 hours either at the beginning of the myoblast stage (Group 1) or at the end of the myoblast stage (Group 2). Cells were further differentiated to myotubes and analyzed 7 days later at the end of the myotube stage (see FIG. 2). Effects on cell counts (FIGS. 11A and 11B) and MF20-positive myotubes (FIGS. 12A and 12B) were assessed. Compound #1 showed significant toxicity at higher doses when added at the beginning of the myoblast stage (FIG. 11A). There were several surprising observations: (1) Compound #1 was much more toxic for normal myoblasts than for FSHD-affected myoblasts, and (2) Compound #1 was only mildly toxic (normal) or not toxic (FSHD) when added at the end of the myoblast stage. Compound #2 was not toxic to any of the cell lines under any treatment regimen (FIG. 11B) but interestingly promoted myogenesis as evidenced by the dose-dependent increase in MF20-positive myotubes (FIG. 12B).

Figure 13A:
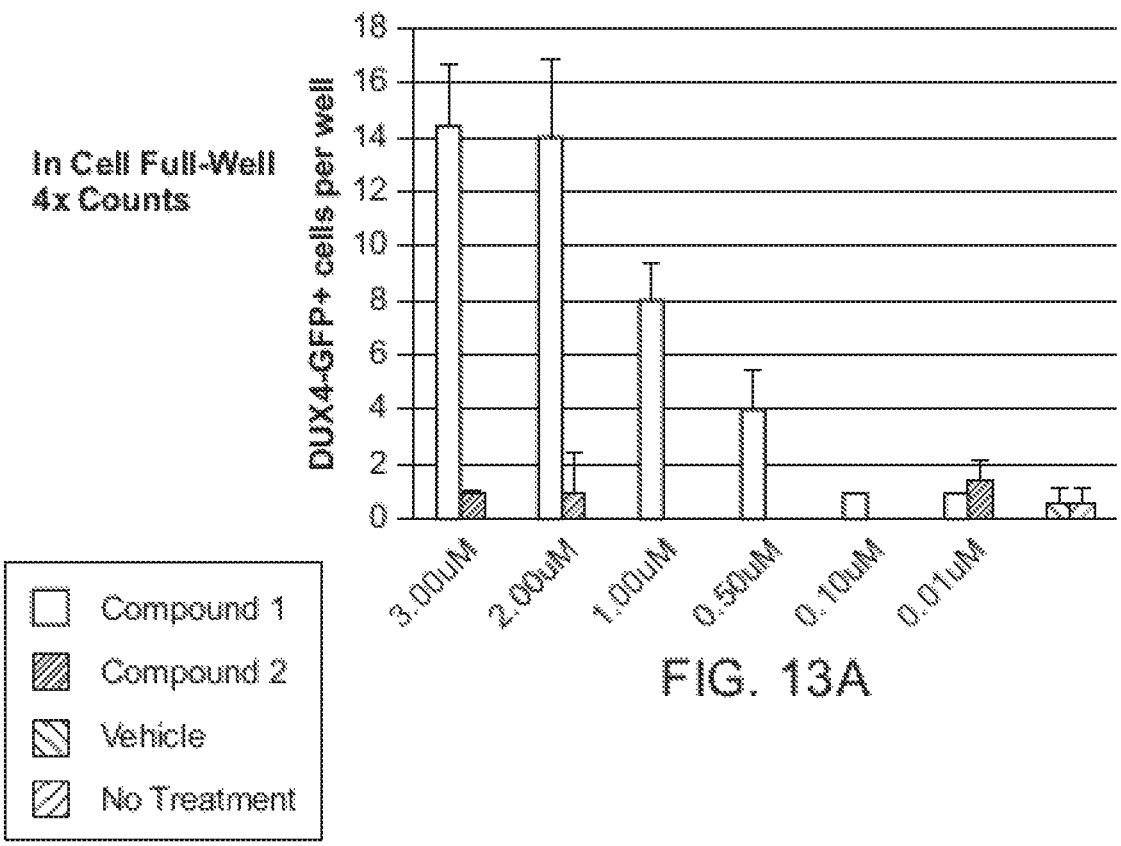
FIGS. 13A-13B illustrate the effect of a DNA methyltransferase inhibitor (Compound #1) or a histone methyltransferase inhibitor (Compound #2) on the number of DUX4-positive cells 13A; and overall cell numbers 13B in cells treated with the compounds for 24 hours at the end of the myoblast stage.
Figure 13B:
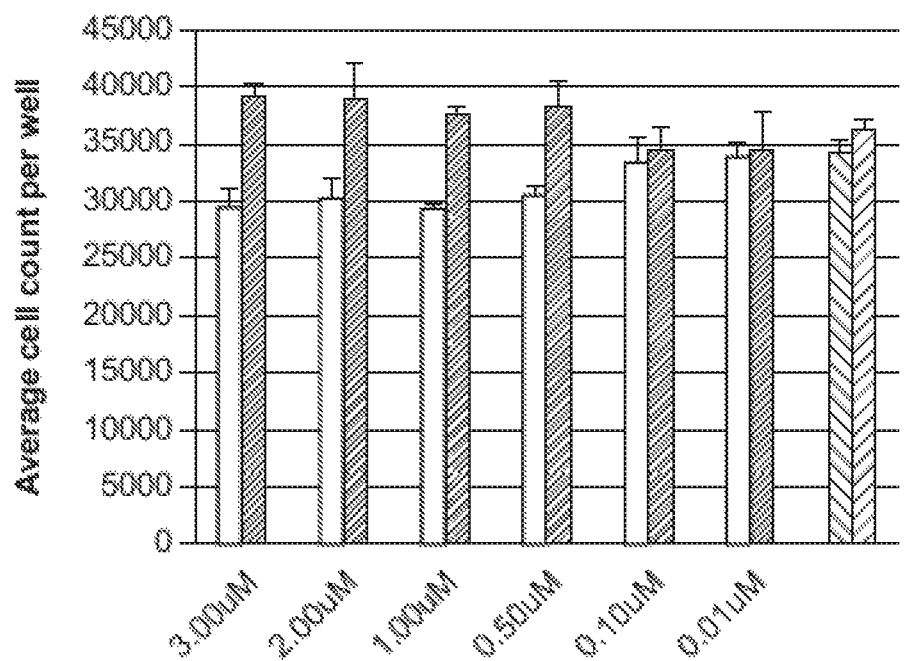

In another example, Genea049 reporter cell line was differentiated according to Example 1 and the compounds were added for 24 hours at the end of the myoblast stage. Cells were further differentiated to myotubes and analyzed 7 days later at the end of the myotube stage (see FIG. 2) by fixation, counterstaining nuclei with Hoechst and visualizing nuclei and the reporter by high-content imaging. An analysis of the DUX4 reporter in the FSHD-affected Genea049 reporter cell line surprisingly showed Compound #1 (ASK10) resulting in a significant increase in DUX4-positive cells in a dose-dependent manner while Compound #2 (ASK19) had no effect (FIGS. 13A and 13B).

Figure 14A:
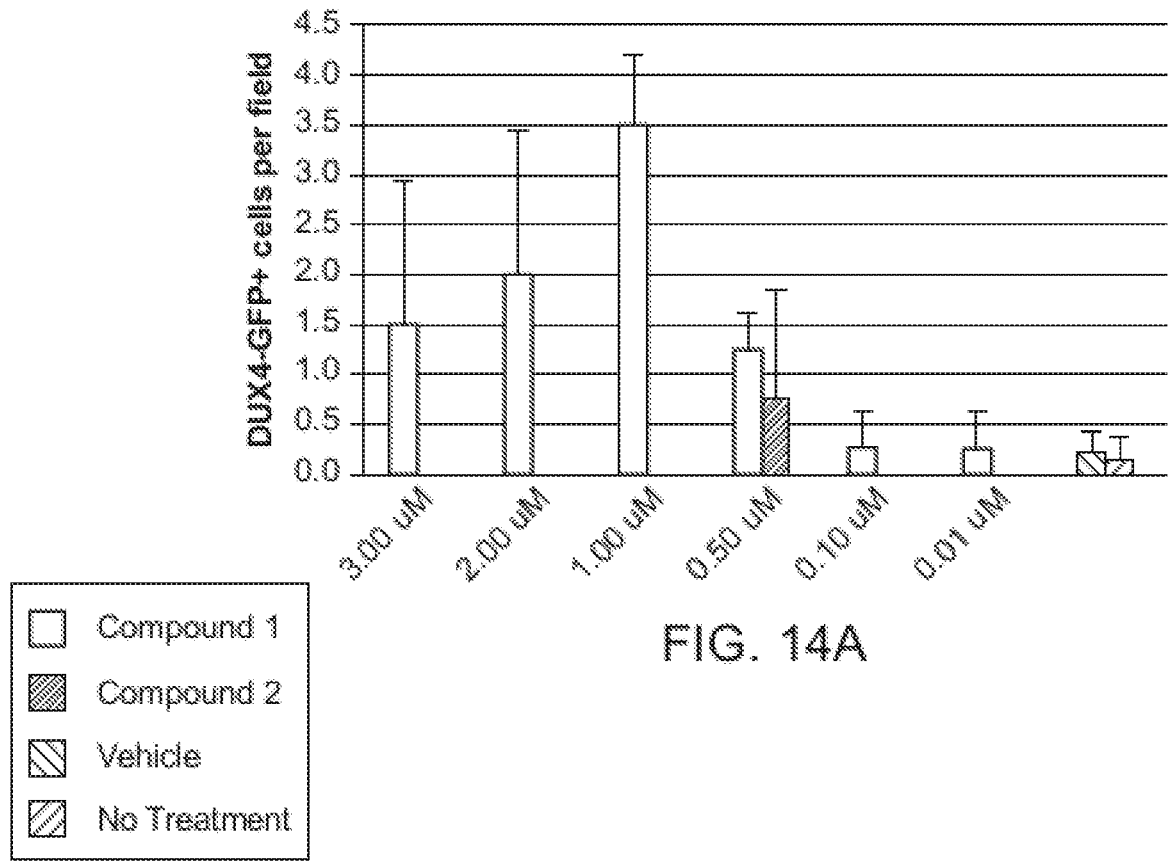
FIGS. 14A-14B illustrate the effect of a DNA methyltransferase inhibitor (Compound #1) or a histone methyltransferase inhibitor (Compound #2) on the number of DUX4-positive cells 14A; and overall cell numbers 14B as measured by video microscopy of cells treated with the compounds for 24 hours at the beginning of the myoblast stage.
Figure 14B:
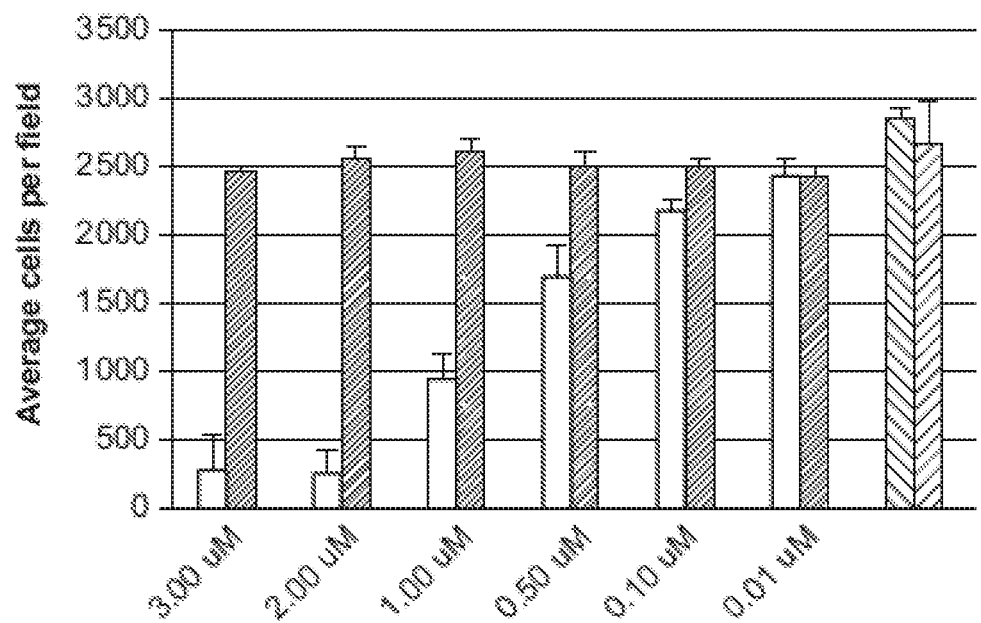

In another example, Genea049 reporter cell line was differentiated according to Example 1 and the compounds were added for 24 hours at the beginning of the myoblast stage. Cells were further differentiated to myotubes (see FIG. 2) and analyzed continuously by video fluorescence microscopy using an Incucyte Zoom instrument (Essen Bioscience). An analysis of the DUX4 reporter in the FSHD-affected Genea049 reporter cell line shows again that Compound #1 (ASK10) resulted in a significant increase in DUX4-positive cells in a dose-dependent manner while surprisingly, Compound #2 (ASK19) suppressed DUX4 expression and/or function (FIGS. 14A and 14B). Also surprisingly, cell death induced by Compound #1 occurred 6-7 days after the compound had been removed demonstrating the long-term effects that short pulses of compound incubation have on the cells.

Figure 17A:
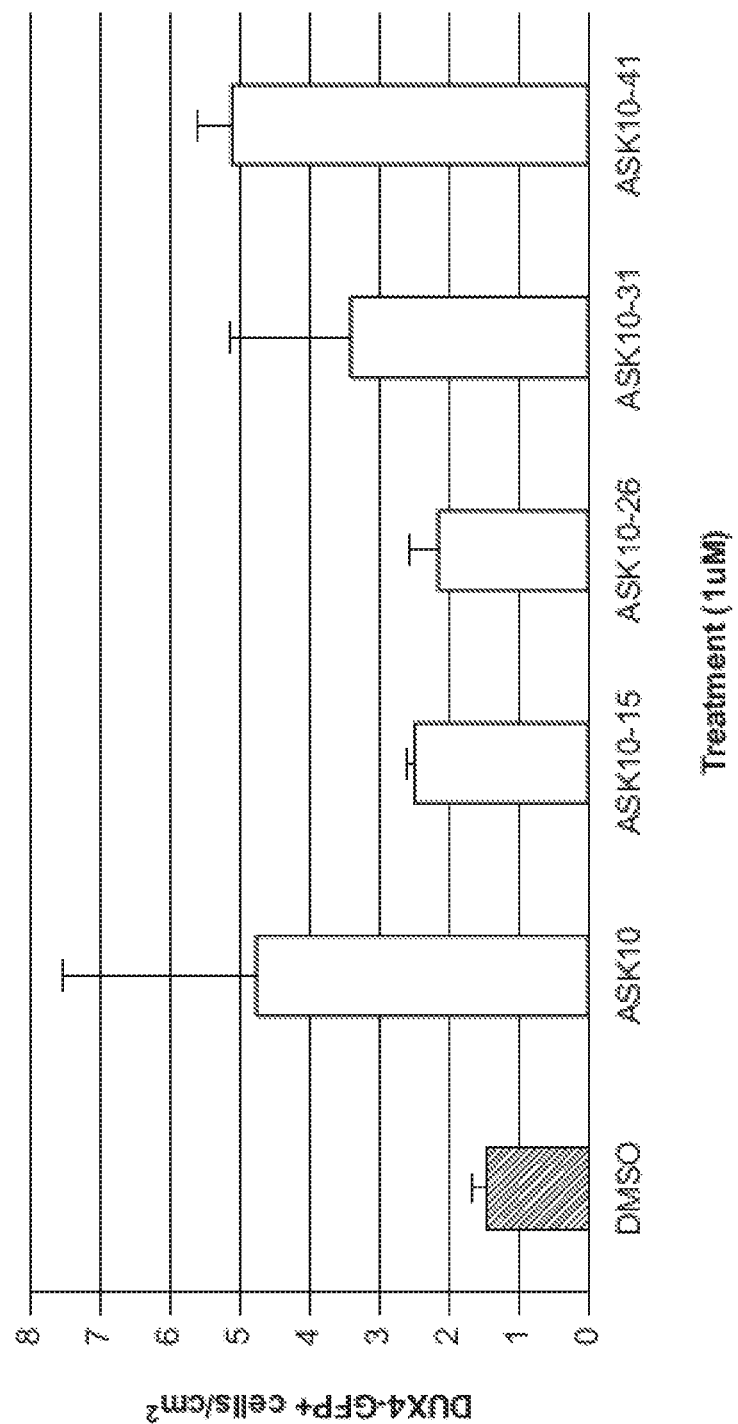
FIGS. 17A-17B show that multiple chemically diverse analogs of ASK10 (exemplified by ASK10-15, ASK10-16, ASK10-2, ASK10-28, ASK10-31, ASK10-41) activate DUX4 expression in cells treated with 1 µm of the compound 17A; multiple chemically diverse analogs of ASK10 also activate DUX4 expression in cells treated with 100 nm of the compound 17B.
Figure 17B:
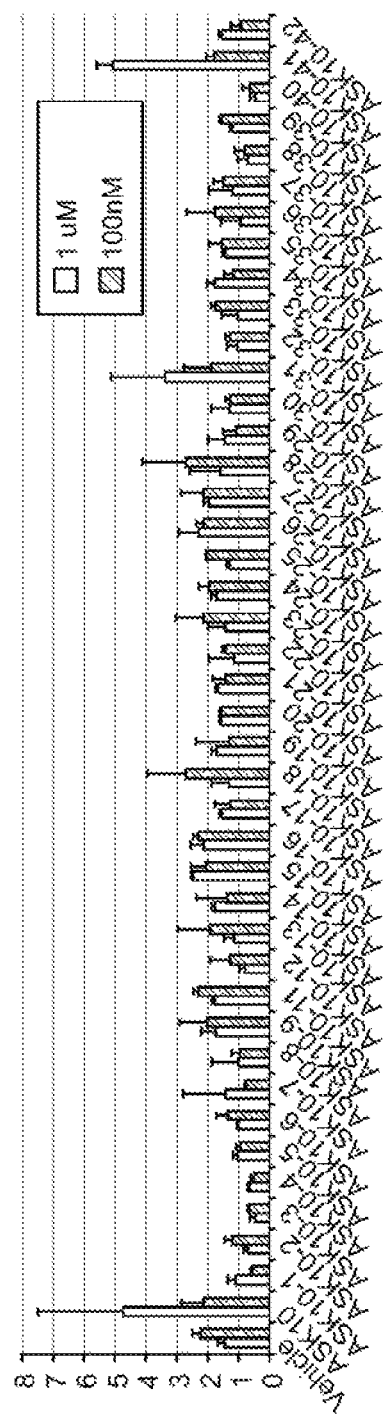
Figure 18:
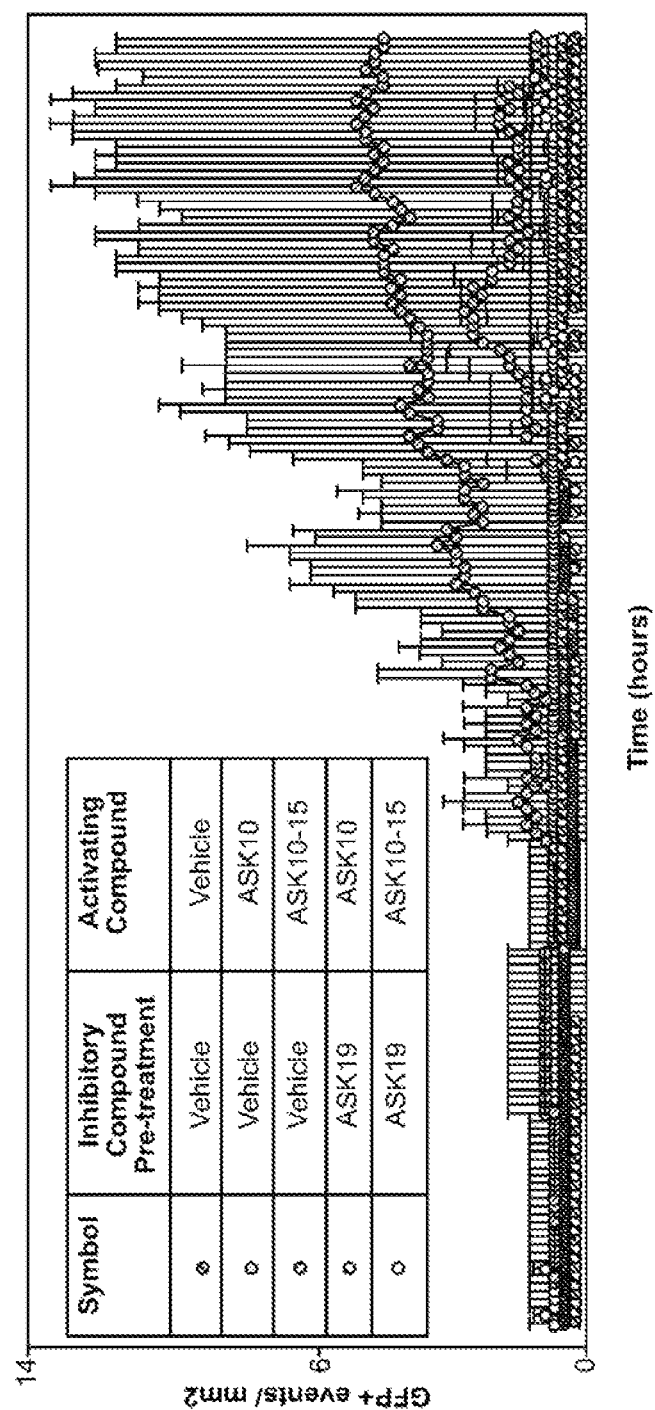
FIG. 18 shows that pre-treatment with ASK19 rescues ASK10- and ASK10 analog-induced DUX4 activation.

In another example, epigenetic modulator ASK10 may activate DUX4 expression by about 12-15 fold greater versus vehicle control in a dose- and exposure time-dependent manner about 48 hours post-exposure. ASK10-mediated DUX4 induction may plateau at about 120 hours post-exposure. The most significant DUX4 expression induction has been detected at $EC_{50}$ equal or >1 uM, as measured by the DUX4-GFP cell number per well. In addition, ASK10 did not display any noticeable cytotoxicity (FIG. 11A). Screening a diverse panel of lead-like analogues of ASK10 (42 compounds) yielded multiple hits showing robust induction of DUX4-GFP at about 2-4 fold greater compared to control, A few representative examples including the comparator molecule ASK10 and respective analogues ASK10-15, ASK10-26, ASK10-31 and ASK10-41 are summarized in FIGS. 17A-17B. Screening a set of biologically diverse chemical series (Table 3) with specific emphasis on epigenetic modulators resulted in identification of ASK19. This active molecule rescued ASK10 and ASK10-15 (active ASK10 analogue)—induced DUX4-GFP production in a dose-dependent manner with tentative $EC_{50}$ of about 0.25-0.5 uM (FIG. 18). The observed 'rescue' effect of ASK19 further validates the chemically-induced DUX4-GFP screening model and demonstrates that it may be used to test additional small molecule modulators of DUX4 toxicity to both model FSHD and to develop/optimize the respective therapeutic agent that reduces/attenuates DUX4 expression in vivo. [FIG. 18 depicts five different curves representing five different treatment conditions. The vehicle/vehicle curve extends along the bottom of the graph, as do the ASK19/ASK10 curve and the ASK19/ASK10-15 curves. In contrast, the vehicle/ASK10 curve increases for a period of time before decreasing; and the vehicle/ASK10-15 curve increases fairly consistently over time and reaches the highest number of GFP+ events as compared to the four other treatment conditions.]

Example 7: Mechanisms of Action

While not intending to be limited by any theory of operation, blocking induction of FSHD-related biomarkers may occur by one of several mechanisms: i) blocking de-repression of DUX4, ii) interfering with DUX4 activity subsequent to its de-repression and iii) via a DUX4-independent mechanism. Levels of DUX4 mRNA by qRT-PCR in the samples from compound treatment are measured. To ensure that HMT inhibitors did not interfere with DUX4 activity, a co-transfection experiment is performed in which myoblasts from normal DUX4 reporter cell lines are transfected with a DUX4 expression plasmid. Three hours after transfection is started. HMT inhibitor is added at concentrations up to twenty fold higher than needed to completely block DUX4 de-repression in the differentiation model. DUX4 reporter activity is assessed 24 hours after transfection. Even at a 10 μM concentration, HMT inhibitor has a marginal (not statistically significant) effect on DUX4 activity. Thus, HMT inhibitors may inhibit the expression of DUX4 rather than its activity.

Based on the above, there is about a 90-fold induction of DUX4 mRNA upon differentiation of FSHD myoblasts for 6 days. The HMT inhibitor appears to block this induction which is not due to indirectly blocking muscle cell differentiation since HMT inhibitors do not alter the expression levels of muscle-related/myogenic genes in Example 4.

HMT inhibitors inhibit the activity of a specific HMT. However, inhibition of additional HMT proteins may yield a positive effect on FSHD. In some cases, general inhibition of HMT can be a useful treatment for FSHD and any HMT inhibitor can be used. However, it is known that broad spectrum HMT inhibitors often produce undesirable effects. Because of the above concerns, while one embodiment of the present invention provides that a broad spectrum HMT inhibitor may be used to treat the effects of FSHD, it is desirable to identify additional selective alternatives. In one example, this can be accomplished through the use of a selective HMT inhibitor which targets only a subset of the relevant HMT, ideally only one or two. Further, it may alternatively or additionally be desirable to be able to administer HMT inhibitor in a limited dose and then remove it so long as the DUX4 expression remains inhibited. Such a 'pulsatile' treatment plan can reduce general immunosuppressive effects allowing a patient's system to recover between treatments.

While it is believed that general inhibition is suitable, in another example, a combination of RNAi knockdowns and forced expression may be used to determine the specific HMT inhibitor family members whose inhibition results in blocking induction of DUX4 and its targets. Improved targeting of compounds may lead to reduction of side effects. Initially, determining the expression of several suspect HMT genes at the mRNA and protein levels in both normal and FSHD myoblasts in undifferentiated cells and during the course of differentiation can be accomplished. This information alone may provide sufficient detail for further refinement. For example, if the expression of one of the HMT proteins increasing with differentiation can correlate with DUX4 de-repression.

In order to determine which gene targets of HMT are necessary for DUX4 expression, and are thus therapeutic targets in FSHD, experiments are performed to identify which of the possible genes are the most likely target(s) responsible for DUX4 expression. FSHD1 myoblasts are transfected with Silencer Select siRNAs (Ambion, Life Technologies) on Day 0. On day 3, samples are harvested for western analysis. On day 4, RNA is harvested for qRT-PCR analysis. Assays are performed on RNA samples in triplicate and on protein samples in singlets. BRD2 RNA and protein are both selectively depleted with the HMT1 siRNA, HMT2 siRNA and protein are selectively depleted using the HMT3 siRNA, and HMT4 RNA and protein are selectively depleted by either of the two HMT4 siRNAs as compared to the various controls.

Example 8: Experimental Protocols for DUX4 Induction and Rescue

Genea's FSHD-affected Gen049 human Embryonic Stem Cells (hESCs) were cultured on geltrex (Thermo Fisher) using the feeder-free mTeSR system (StemCell Technologies). Cells were transduced with a lentivirus coding for a synthetic DUX4-responsive promoter driving a nuclear turboGFP reporter gene (Rickard et al., 2015) and selected using G418 antibiotic (Thermo Fisher). Myogenic differentiation was induced using the Genea Biocells muscle differentiation protocol (Caron et al., 2016). Reporter stem cells were treated with Accutase (StemCell Technologies) and plated as single cells at 5200 cells/cm2, then changed to Stage 1 Myogenic Induction Medium (Genea Biocells). Media was changed every other day for 10 days. Myogenic precursors were then re-seeded by treatment with Passaging Solution (Genea Biocells) followed by Neutralizing Solution (Genea Biocells), were pelleted, and were plated at 2500 cells/cm2 in Stage 2 Myoblast Medium (Genea Biocells).

Figure 15A:
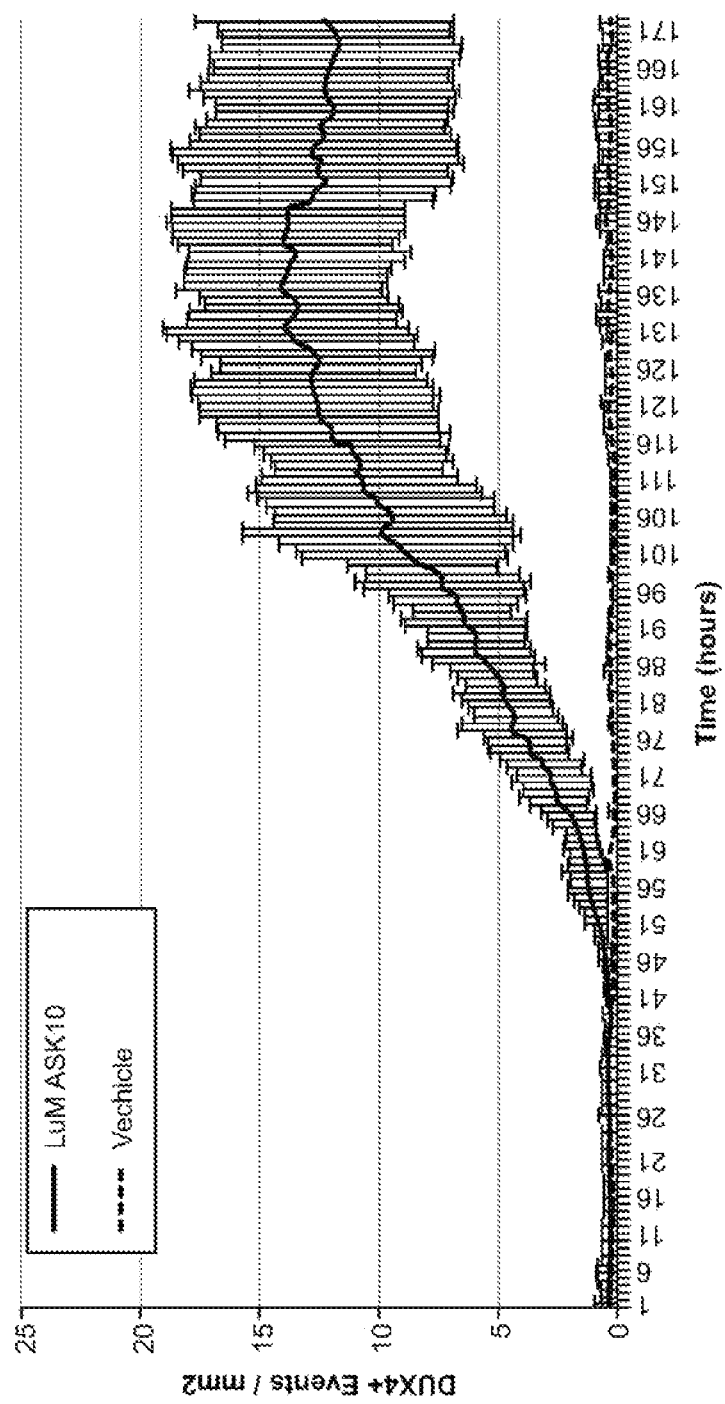
FIGS. 15A-15B show that ASK10 activates DUX4 expression in an exposure time-dependent manner, as shown by the increase in the number of DUX4-expressing cells following an increase in exposure time with ASK10 from approximately 1 to 120 hours 15A; and increase in the number of DUX4-expressing cells following an increase in exposure time with ASK 10 15B.
Figure 15B:
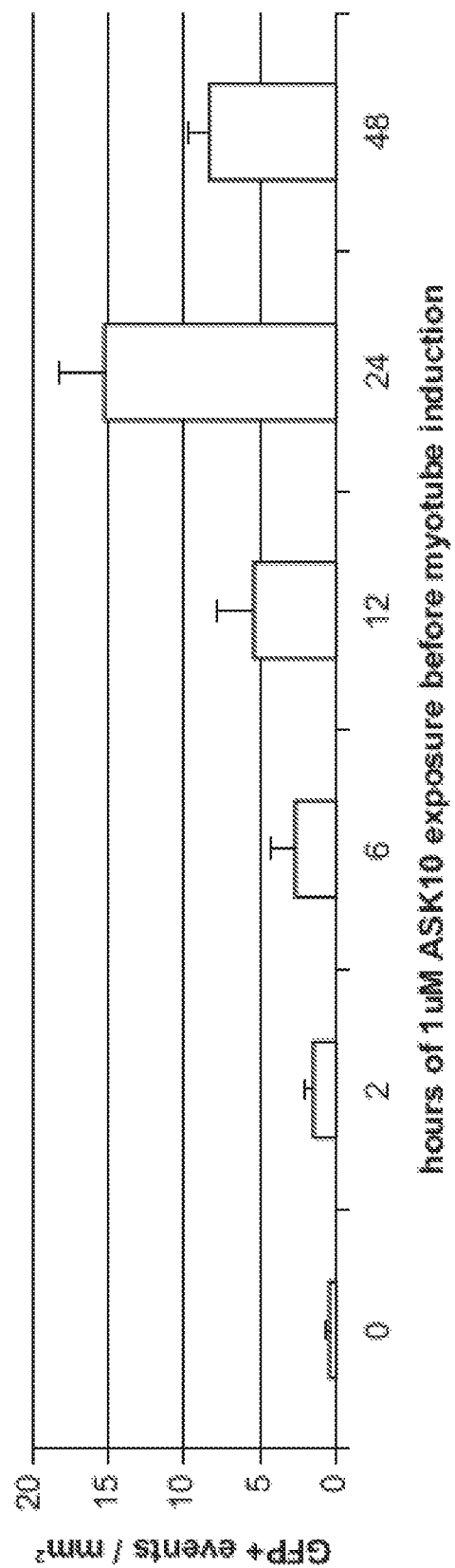

In rescue experiments, Stage 2 Day 1 cells were then treated with either 1 uM ASK19 or DMSO vehicle for 24 hours. Precursors were then converted to myoblasts by culture in Stage 2 Medium for 7 days with media changes every second day until confluence. Myoblasts were passaged and seeded at 9000 cells/cm2 in 96 well format, allowed to grow to confluence, and treated in Stage 2 Medium for indicated time (0-48 hours) with 0.01 uM-3 uM of ASK10, ASK10 analog, DMSO vehicle, or media only (FIGS. 15A-15B). After treatment, confluent myoblasts were switched to Stage 3 Myotube Medium (Genea Biocells). Cells were imaged hourly for phase and DUX4-GFP reporter fluorescence with the Incucyte live cell imaging system (Essen Bioscience) and Incucyte analysis software reported GFP+ events/mm2. After imaging, cells were fixed in 10% Formalin (Thermo Fisher) for 15 minutes and stained for 2 hours using PBS (Invitrogen) with 5% BSA (Thermo Fisher), 0.25% Triton-X (Thermo Fisher), and 1:5000 Hoechst (Thermo Fisher) DNA dye. Nuclei were quantified using the In Cell 6000 imaging and analysis suite.

Figure 16A:
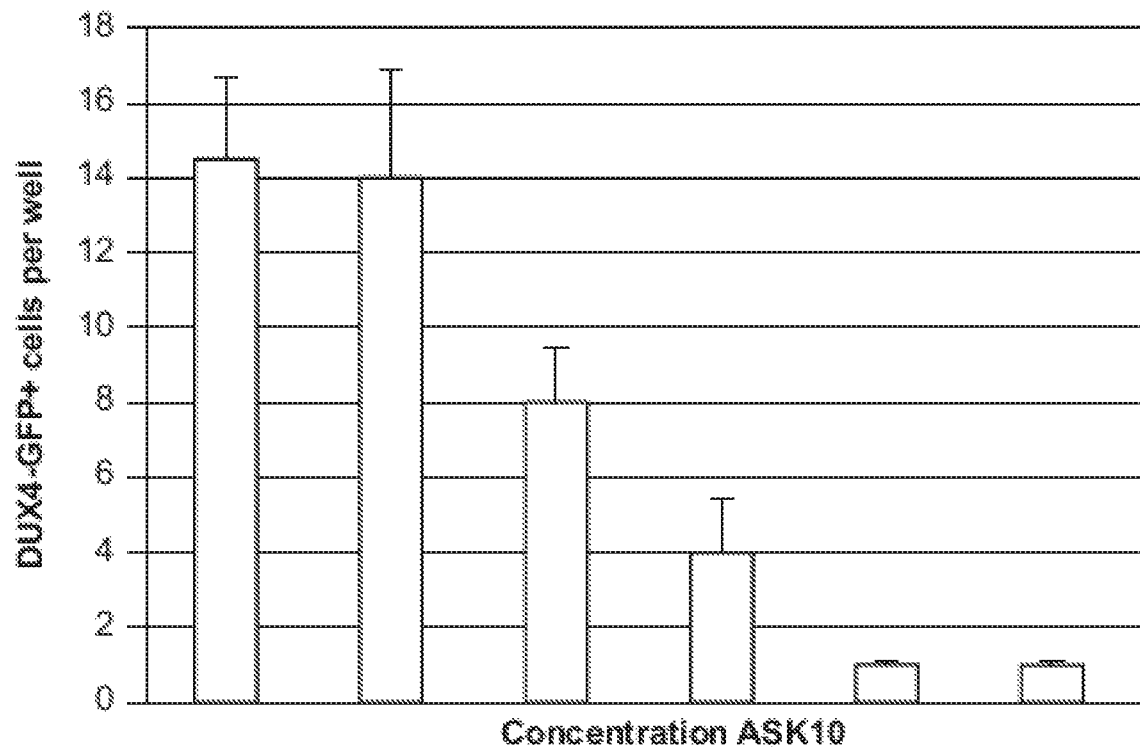
FIGS. 16A-16B show that ASK10 activates DUX4 expression in a dose-dependent manner, as shown by the number of DUX4-GFP positive cells per well in cells treated with various concentrations of ASK10 16A; and the average total cell number in wells treated with various concentrations of ASK10 16B.
Figure 16B:
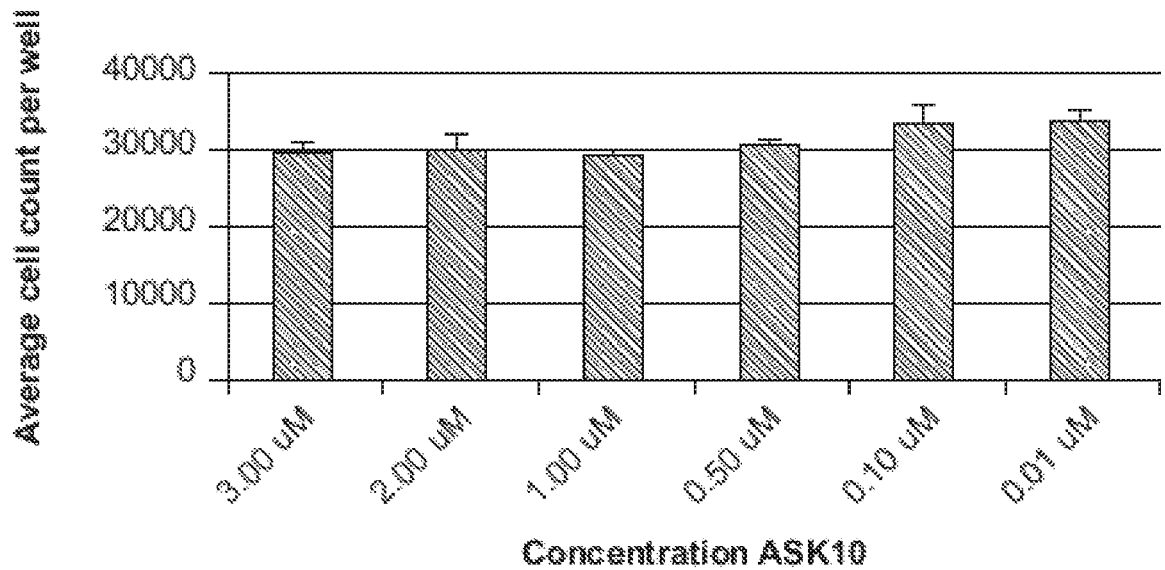
Figure 19:
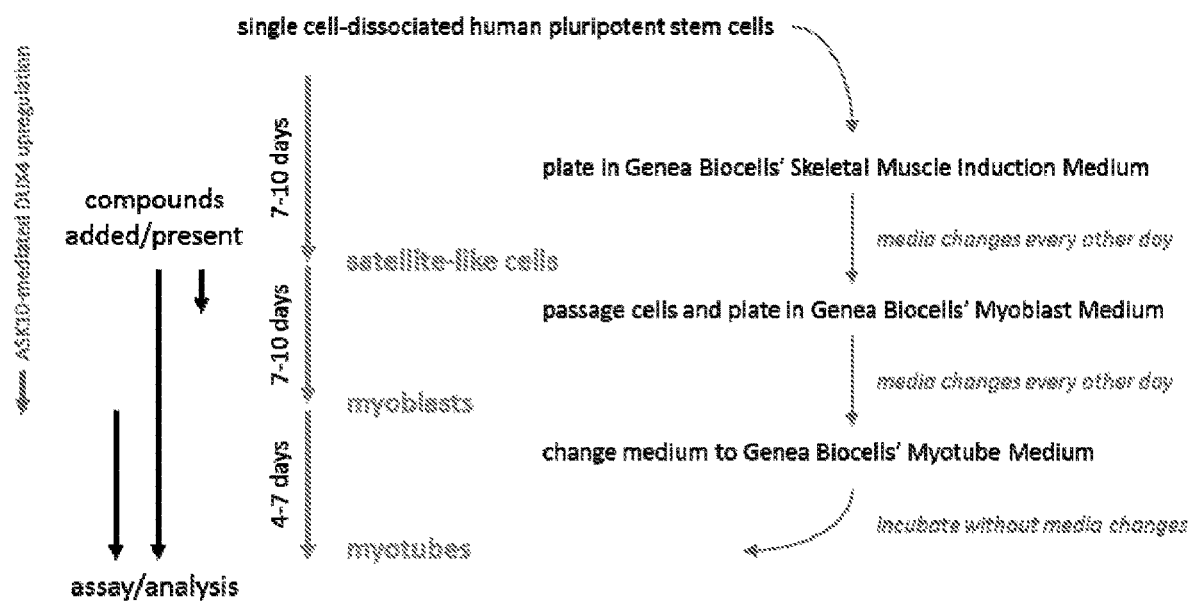
FIG. 19 is an overview depicting methods of differentiating human pluripotent stem cells to skeletal muscle using ASK10 or ASK10 analog-mediated increased expression of DUX4 for drug screening.

The system as described herein can be used as a sensitive low-, medium- or high-throughput screening assay to identify compounds that suppress DUX4 following an experimental procedure as outlined in FIG. 19. A 24 hour pulse of ASK10 or ASK10-like compounds is used at the end of differentiation stage 2 to increase the expression of DUX4 to more easily detectable levels and thereby increasing the assay sensitivity. Test compounds are added either at the beginning of differentiation stage 2 or stage 3 and may be present throughput the experiment. Ultimately, the number of DUX4 expression cells, total cells, and total number of myotubes formed can be assessed by high-content analysis (FIGS. 16A-16B).

Example 9: Treatment of Facioscapulohumeral Muscular Dystrophy (FSHD) with Histone Methyltransferase Inhibitor In this prophetic example, a patient is diagnosed with facioscapulohumeral muscular dystrophy (FSHD). The patient is treated with a therapeutically effective dose of a compound of Formula (I). The compound is given to the patient by oral, intravenous, or intramuscular administration. The compound causes a reduction in DUX4 expression. The patient is treated about once every month. After one month of treatment, six months of treatment, and one year of treatment, the patient is assessed for reduction in symptoms of FSHD.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of treating facioscapulohumeral muscular dystrophy (FSHD) in a subject in need thereof, the method comprising: administering to the subject in need thereof a therapeutically effective amount of a compound of Formula (II):

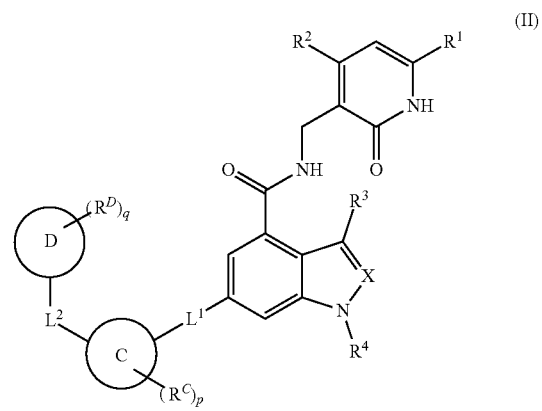

or a pharmaceutically acceptable salt thereof, wherein:
C comprises a bond, $C_{5-12}$ carbocycle, or 5- to 12-membered heterocycle;
D comprises a bond, $C_{5-12}$ carbocycle, or 5- to 12-membered heterocycle;
each of $L^1$ and $L^2$ independently comprises a bond, —O—, —S, —N($R^{51}$), —N($R^{51}$)CH$_2$—, —C(O), —C(O)O, —OC(O), —OC(O)O, —C(O)N($R^{51}$), —C(O)N($R^{51}$)C(O)—, —C(O)N($R^{51}$)C(O)N($R^{51}$), —N($R^{51}$)C(O), —N($R^{51}$)C(O)N($R^{51}$), —N($R^{51}$)C(O)O, —OC(O)N($R^{51}$), —C(N$R^{51}$), —N($R^{51}$)C(N$R^{51}$), —C(N$R^{51}$)N($R^{51}$), —N($R^{51}$)C(N$R^{51}$)N($R^{51}$), —S(O)$_2$, —OS(O), —S(O)O—, —S(O), —OS(O)$_2$, —S(O)$_2$O, —N($R^{51}$)S(O)$_2$, —S(O)$_2$N($R^{51}$), —N($R^{51}$)S(O), —S(O)N($R^{51}$), —N($R^{51}$)S(O)$_2$N($R^{51}$)—, or —N($R^{51}$)S(O)N($R^{51}$) or from alkylene, alkenylene, alkynylene, heteroalkylene, heteroalkenylene, or heteroalkynylene, each of which is optionally substituted with one or more $R^{50}$;
$R^{50}$ is, at each occurrence, independently comprises:
halogen, —NO$_2$, CN, —OR$^{52}$, —SR$^{52}$, —N(R$^{52}$)$_2$, —NR$^{53}$R$^{54}$, —S(═O)R$^{52}$, —S(═O)$_2$R$^{52}$, —S(═O)$_2$N(R$^{52}$)$_2$, —S(═O)$_2$NR$^{53}$R$^{54}$, —NR$^{52}$S(═O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, or =N(R$^{52}$);

C$_{1-10}$ alkyl, C$_{2-10}$ alkenyl, and C$_{2-10}$ alkynyl, each of which is independently optionally substituted at each occurrence with one or more substituents comprises halogen, —NO$_2$, CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$), C$_{3-12}$ carbocycle, or 3- to 12-membered heterocycle; or C$_{3-12}$ carbocycle and 3- to 12-membered heterocycle, wherein each C$_{3-12}$ carbocycle and 3- to 12-membered heterocycle in R$^{50}$ is independently optionally substituted with one or more substituents comprises halogen, —NO$_2$, CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$NR$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$—NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$), C$_{1-6}$ alkyl, C$_{1-6}$ haloalkyl, C$_{2-6}$ alkenyl, or C$_{2-6}$ alkynyl;

R$^{51}$, at each occurrence, independently comprises: hydrogen, —C(O)R$^{52}$, —C(O)OR$^{52}$, —C(O)N(R$^{52}$)$_2$, —C(O)NR$^{53}$R$^{54}$;

C$_{1-6}$ alkyl, C$_{2-6}$ alkenyl, and C$_{2-6}$ alkynyl, each of which is independently optionally substituted at each occurrence with one or more substituents comprising halogen, —NO$_2$, CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$), C$_{3-12}$ carbocycle or 3- to 12-membered heterocycle; or C$_{3-12}$ carbocycle and 3- to 12-membered heterocycle, wherein each C$_{3-12}$ carbocycle and 3- to 12-membered heterocycle in R$^{51}$ is independently optionally substituted with one or more substituents comprising halogen, —NO$_2$, CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$ N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$), C$_{1-6}$ alkyl, C$_{1-6}$ haloalkyl, C$_{2-6}$ alkenyl, or C$_{2-6}$ alkynyl;

R$^{52}$, at each occurrence, independently comprising hydrogen; and C$_{1-20}$ alkyl, C$_{2-20}$ alkenyl, C$_{2-20}$ alkynyl, 1- to 6-membered heteroalkyl, C$_{3-12}$ carbocycle, or 3- to 12-membered heterocycle, each of which is optionally substituted by halogen, —CN, —NO$_2$, —NH$_2$, —NHCH$_3$, —NHCH$_2$CH$_3$, =O, —OH, —OCH$_3$, —OCH$_2$CH$_3$, C$_{3-12}$ carbocycle, or 3- to 6-membered heterocycle;

R$^{53}$ and R$^{54}$ are taken together with the nitrogen atom to which they are attached to form a heterocycle, optionally substituted with one or more R$^{50}$;

each of R$^A$, R$^B$, and R$^c$ independently comprising R$^{50}$;

R$^D$ is, at each occurrence, independently comprising hydrogen or R$^{50}$; and each of m, n, p, and q is independently an integer from 0-12, X is C—R$^5$ or N;

each of R$^1$ and R2 is independently R$^{50}$;

R$^3$ comprises hydrogen or R$^{50}$;

R$^4$ is R$^{52}$; and

R$^5$ comprises hydrogen or R$^{50}$;

thereby treating facioscapulohumeral muscular dystrophy (FSHD) in the subject in need thereof.

2. The method of claim 1, wherein C comprises a bond, a 6-membered aryl, or a 6-membered heterocycle.

3. The method of claim 1, wherein C comprises pyridinylene, phenylene, tetrahydropyranylene, or piperidinylene.

4. The method of claim 1, wherein D comprises a bond and a 6-membered heterocycle.

5. The method of claim 1, wherein D comprises piperazinyl and morpholinyl.

6. The method of claim 1, wherein R$^3$ is H or —CH$_3$.

7. The method of claim 1, wherein R$^4$ is C$_{1-5}$ alkyl or C$_{1-5}$.

8. A method of treating facioscapulohumeral muscular dystrophy (FSHD) in a subject in need thereof, the method comprising: administering to the subject in need thereof a therapeutically effective amount of a compound of Formula (III):

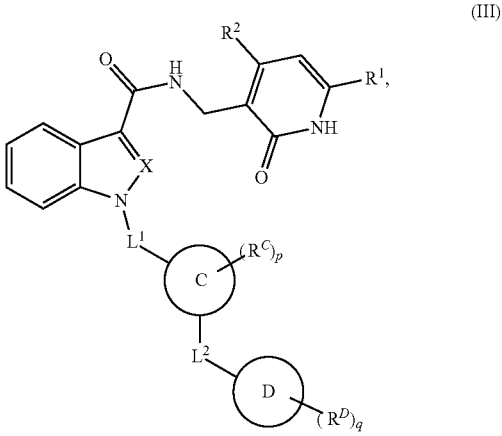

(III)

or a pharmaceutically acceptable salt thereof, wherein:

C comprises a bond, $C_{5-12}$ carbocycle, or 5- to 12-membered heterocycle:

D comprises a bond, $C_{5-12}$ carbocycle, or 5- to 12-membered heterocycle;

each of $L^1$ and $L^2$ independently comprises a bond, —O—, —S, —N($R^{51}$), —N($R^{51}$)$CH_2$—, —C(O), —C(O)O, —OC(O), —OC(O)O, —C(O)N($R^{51}$), —C(O)N($R^{51}$)C(O)—, —C(O)N($R^{51}$)C(O)N($R^{51}$), —N($R^{51}$)C(O), —N($R^{51}$)C(O)N($R^{51}$), —N($R^{51}$)C(O)O, —OC(O)N($R^{51}$), —C(N$R^{51}$), —N($R^{51}$)C(N$R^{51}$), —C(N$R^{51}$)N($R^{51}$), —N($R^{51}$)C(N$R^{51}$)N($R^{51}$), —S(O)$_2$, —OS(O), —S(O)O—, —S(O), —OS(O)$_2$, —S(O)$_2$O, —N($R^{51}$)S(O)$_2$, —S(O)$_2$N($R^{51}$), —N($R^{51}$)S(O), —S(O)N($R^{51}$), —N($R^{51}$)S(O)$_2$ N($R^{51}$)—, or —N($R^{51}$)S(O)N($R^{51}$) or from alkylene, alkenylene, alkynylene, heteroalkylene, heteroalkenylene, or heteroalkynylene, each of which is optionally substituted with one or more $R^{50}$;

$R^{50}$ is, at each occurrence, independently comprising: halogen, —NO$_2$, CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, C(O)N(R$^{52}$)$_2$, —C(O)NR$^{53}$R$^{54}$, —P(O)(OR$^{52}$)$_2$, —P(O)(R$^{52}$)$_2$, —P(O)(OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, or =N(R$^{52}$);

$C_{1-10}$ alkyl, $C_{2-10}$ alkenyl, and $C_{2-10}$ alkynyl, each of which is independently optionally substituted at each occurrence with one or more substituents comprising halogen, —NO$_2$, CN, —OR$^{52}$, —SR$^{52}$—N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O) OR$^{52}$, —OC(O)N(R$^{52}$)$_2$, —OC(O)NR$^{53}$R$^{54}$, —NR$^{52}$C (O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O) NR$^{53}$R$^{54}$, —P(O)(OR$^{52}$)$_2$, —P(O)(R$^{52}$)$_2$, —P(O) (OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$), $C_{3-12}$ carbocycle or 3- to 12-membered heterocycle; or $C_{3-12}$ carbocycle and 3- to 12-membered heterocycle, wherein each $C_{3-12}$ carbocycle and 3- to 12-membered heterocycle in $R^{50}$ is independently optionally substituted with one or more substituents comprising halogen, —NO$_2$, CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O) OR$^{52}$, —OC(O)N(R$^{52}$)$_2$, —OC(O)NR$^{53}$R$^{54}$, —NR$^{52}$C (O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O) NR$^{53}$R$^{54}$, —P(O)(OR$^{52}$)$_2$, —P(O)(R$^{52}$)$_2$, —P(O) (OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$), $C_{1-6}$ alkyl, $C_{1-6}$ haloalkyl, $C_{2-6}$ alkenyl, or $C_{2-6}$ alkynyl;

$R^{51}$, at each occurrence, independently comprising: hydrogen, —C(O)R$^{52}$, —C(O)OR$^{52}$, —C(O)N(R$^{52}$)$_2$, —C(O)NR$^{53}$R$^{54}$;

$C_{1-6}$ alkyl, $C_{2-6}$ alkenyl, and $C_{2-6}$ alkynyl, each of which is independently optionally substituted at each occurrence with one or more substituents comprising halogen, —NO$_2$, CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O) OR$^{52}$, —OC(O)N(R$^{52}$)$_2$, —OC(O)NR$^{53}$R$^{54}$, —NR$^{52}$C (O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O) NR$^{53}$R$^{54}$, —P(O)(OR$^{52}$)$_2$, —P(O)(R$^{52}$)$_2$, —P(O) (OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$), $C_{3-12}$ carbocycle, or 3- to 12-membered heterocycle; or $C_{3-12}$ carbocycle and 3- to 12-membered heterocycle, wherein each $C_{3-12}$ carbocycle and 3- to 12-membered heterocycle in $R^{51}$ is independently optionally substituted with one or more substituents comprising halogen, —NO$_2$, CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O) OR$^{52}$, —OC(O)N(R$^{52}$)$_2$, —OC(O)NR$^{53}$R$^{54}$, —NR$^{52}$C (O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O) NR$^{53}$R$^{54}$, —P(O)(OR$^{52}$)$_2$, —P(O)(R$^{52}$)$_2$, —P(O) (OR$^{52}$)(R$^{52}$), —P(O)(NR$^{52}$)(R$^{52}$), —NR$^{52}$P(O)(R$^{52}$), —P(O)(NR$^{52}$)(OR$^{52}$), —P(O)(NR$^{52}$)$_2$, =O, =S, =N(R$^{52}$), $C_{1-6}$ alkyl, $C_{1-6}$ haloalkyl, $C_{2-6}$ alkenyl, or $C_{2-6}$ alkynyl;

$R^{52}$, at each occurrence, independently comprising hydrogen; and $C_{1-20}$ alkyl, $C_{2-20}$ alkenyl, $C_{2-20}$ alkynyl, 1- to 6-membered heteroalkyl, $C_{3-12}$ carbocycle, or 3- to 12-membered heterocycle, each of which is optionally substituted by halogen, —CN, —NO$_2$, —NH$_2$, —NHCH$_3$, —NHCH$_2$CH$_3$, =O, —OH, —OCH$_3$, —OCH$_2$CH$_3$, $C_{3-12}$ carbocycle, or 3- to 6-membered heterocycle;

$R^{53}$ and $R^{54}$ are taken together with the nitrogen atom to which they are attached to form a heterocycle, optionally substituted with one or more $R^{50}$;

each of $R^A$, $R^B$, and $R^C$ independently comprising $R^{50}$;

$R^D$ is, at each occurrence, independently comprising hydrogen or $R^{50}$; and each of m, n, p, and q is independently an integer from 0-12, X is C—$R^5$ or N;

each of $R^1$ and $R^2$ is independently $R^{50}$; and $R^5$ comprises hydrogen or $R^{50}$.

9. The method of claim 8, wherein $L^1$ is

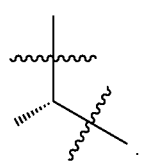

10. The method of claim 1, wherein the compound comprises any one of:

EPZ005687

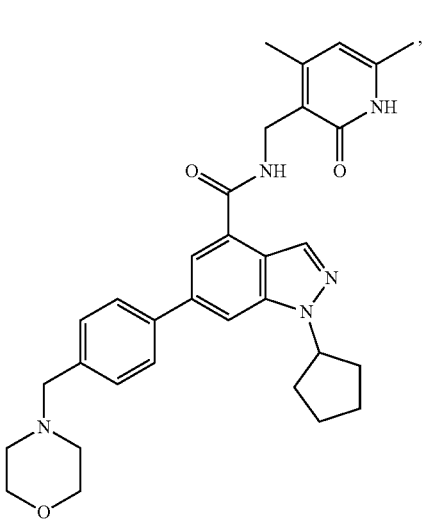

GSK343

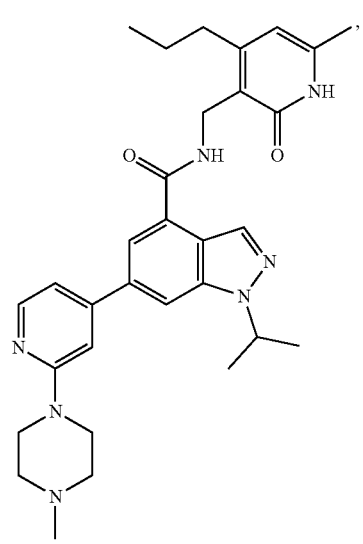

EI-1

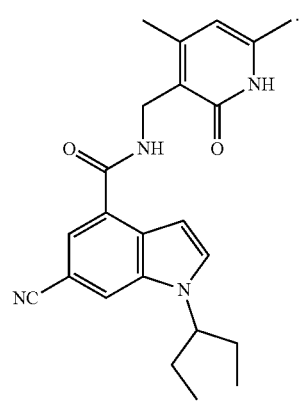

11. The method of claim 1, further comprising administering to the subject a second therapeutic agent.

12. The method of claim 1, further comprising administering to the subject a cell therapy.

13. The method of claim 1, wherein the subject is human.

14. The method of claim 1, wherein the compound is of the formula:

15. The method of claim 8, wherein the compound comprises any one of:

GSK126 (ASK19)

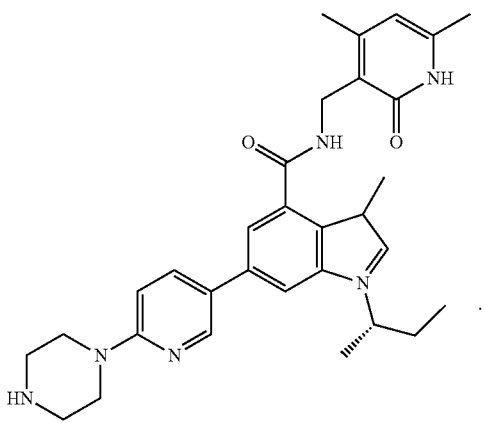

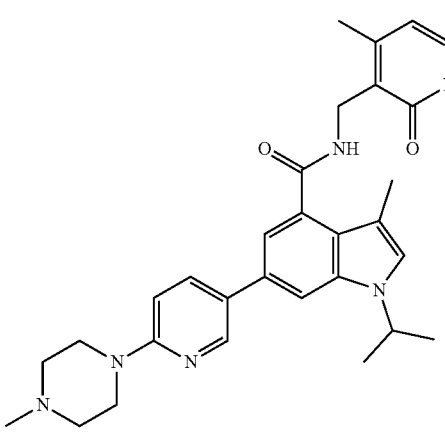

GSK503 and

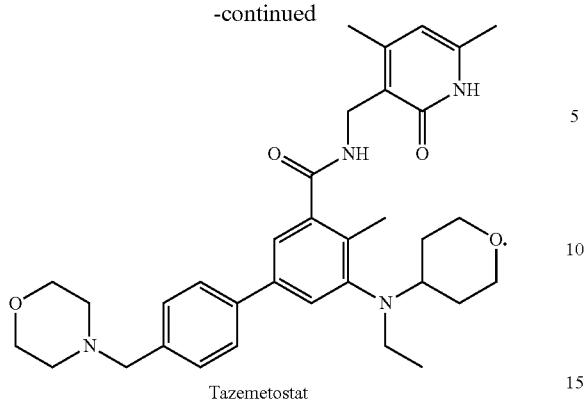
Tazemetostat